United States Patent
Thiele et al.

(10) Patent No.: US 12,098,117 B2
(45) Date of Patent: Sep. 24, 2024

(54) COMPOSITIONS AND METHODS FOR THE TREATMENT OF CANCER

(71) Applicant: DUKE UNIVERSITY, Durham, NC (US)

(72) Inventors: Dennis J. Thiele, Chapel Hill, NC (US); Bushu Dong, Durham, NC (US); Alexander M. Jaeger, Cambridge, MA (US); Philip F. Hughes, Chapel Hill, NC (US); Timothy Haystead, Durham, NC (US); Jiyong Hong, Durham, NC (US)

(73) Assignee: Duke University, Durham, NC (US)

( * ) Notice: Subject to any disclaimer, the term of this patent is extended or adjusted under 35 U.S.C. 154(b) by 311 days.

(21) Appl. No.: 17/312,858

(22) PCT Filed: Dec. 11, 2019

(86) PCT No.: PCT/US2019/065757
§ 371 (c)(1),
(2) Date: Jun. 10, 2021

(87) PCT Pub. No.: WO2020/123675
PCT Pub. Date: Jun. 18, 2020

(65) Prior Publication Data
US 2022/0106265 A1 Apr. 7, 2022

Related U.S. Application Data

(60) Provisional application No. 62/777,831, filed on Dec. 11, 2018.

(51) Int. Cl.
*C07C 275/30* (2006.01)
*A61P 35/00* (2006.01)
(Continued)

(52) U.S. Cl.
CPC ............ *C07C 275/30* (2013.01); *A61P 35/00* (2018.01); *C07C 211/40* (2013.01);
(Continued)

(58) Field of Classification Search
CPC ... C07C 275/30; C07C 211/40; C07C 255/60; C07C 275/28; C07C 275/34;
(Continued)

(56) References Cited

U.S. PATENT DOCUMENTS 6,589,950 B1 7/2003 Collingwood et al.
9,493,442 B2 11/2016 Wu et al.
(Continued)

FOREIGN PATENT DOCUMENTS

CN 103709097 A * 4/2014 .......... C07C 273/18
WO 200138306 A1 5/2001
(Continued)

OTHER PUBLICATIONS

Ha, Helen, et al. "Discovery of Novel CXCR2 Inhibitors Using Ligand-Based Pharmacophore Models." Journal of Chemical Information and Modeling, vol. 55, No. 8, Aug. 2015, pp. 1720-1738. DOI.org (Crossref), https://doi.org/10.1021/acs.jcim.5b00181. (Year: 2015).*

(Continued)

*Primary Examiner* — Clinton A Brooks
*Assistant Examiner* — Kyle Nottingham
(74) *Attorney, Agent, or Firm* — POLSINELLI PC

(57) ABSTRACT

This disclosure relates to compounds, pharmaceutical compositions comprising them, and methods of using the compounds and compositions for treating diseases related to Heat Shock Transcription Factor 1 (HSF1) activity and/or function. More particularly, this disclosure relates to methods of inhibiting HSF1 activity with these compounds and pharmaceutical compositions thereof, and methods of treat- (Continued)

ing diseases associated with HSF1 activity and/or function, such as cancer.

7 Claims, 6 Drawing Sheets

(51) Int. Cl.
| | |
|---|---|
| C07C 211/40 | (2006.01) |
| C07C 255/60 | (2006.01) |
| C07C 275/28 | (2006.01) |
| C07C 275/34 | (2006.01) |
| C07C 275/40 | (2006.01) |
| C07C 275/42 | (2006.01) |
| C07C 279/18 | (2006.01) |
| C07C 279/28 | (2006.01) |
| C07C 281/06 | (2006.01) |
| C07C 311/46 | (2006.01) |
| C07C 317/36 | (2006.01) |
| C07C 317/42 | (2006.01) |
| C07D 213/40 | (2006.01) |
| C07D 213/75 | (2006.01) |
| C07D 223/04 | (2006.01) |
| C07D 229/02 | (2006.01) |
| C07D 231/56 | (2006.01) |
| C07D 233/64 | (2006.01) |
| C07D 241/24 | (2006.01) |
| C07D 249/14 | (2006.01) |
| C07D 271/12 | (2006.01) |
| C07D 285/10 | (2006.01) |
| C07D 317/66 | (2006.01) |
| C07D 333/20 | (2006.01) |
| C07D 333/36 | (2006.01) |
| C07D 333/72 | (2006.01) |
| C07D 405/04 | (2006.01) |
| C07D 405/12 | (2006.01) |
| C07D 417/12 | (2006.01) |

(52) U.S. Cl.
CPC ......... *C07C 255/60* (2013.01); *C07C 275/28* (2013.01); *C07C 275/34* (2013.01); *C07C 275/40* (2013.01); *C07C 275/42* (2013.01); *C07C 279/18* (2013.01); *C07C 279/28* (2013.01); *C07C 281/06* (2013.01); *C07C 311/46* (2013.01); *C07C 317/36* (2013.01); *C07C 317/42* (2013.01); *C07D 213/40* (2013.01); *C07D 213/75* (2013.01); *C07D 223/04* (2013.01); *C07D 229/02* (2013.01); *C07D 231/56* (2013.01); *C07D 233/64* (2013.01); *C07D 241/24* (2013.01); *C07D 249/14* (2013.01); *C07D 271/12* (2013.01); *C07D 285/10* (2013.01); *C07D 317/66* (2013.01); *C07D 333/20* (2013.01); *C07D 333/36* (2013.01); *C07D 333/72* (2013.01); *C07D 405/04* (2013.01); *C07D 405/12* (2013.01); *C07D 417/12* (2013.01)

(58) Field of Classification Search
CPC ... C07C 275/40; C07C 275/42; C07C 279/18; C07C 279/28; C07C 281/06; C07C 311/46; C07C 317/36; C07C 317/42; A61P 35/00; A61P 31/00; C07D 213/40; C07D 213/75; C07D 223/04; C07D 229/02; C07D 231/56; C07D 233/64; C07D 241/24; C07D 249/14; C07D 271/12; C07D 285/10; C07D 317/66; C07D 333/20; C07D 333/36; C07D 333/72; C07D 405/04; C07D 405/12; C07D 417/12; C07D 215/38; C07D 277/42; C07D 309/14; C07D 311/20; C07D 333/44; C07D 409/12; C07D 271/08; A61K 31/17

See application file for complete search history.

(56) References Cited

U.S. PATENT DOCUMENTS

| | | | |
|---|---|---|---|
| 2003/0204085 A1* | 10/2003 | Taveras | C07D 207/08 564/339 |
| 2011/0112073 A1 | 5/2011 | Thiele et al. | |
| 2017/0273922 A1 | 9/2017 | Wu et al. | |

FOREIGN PATENT DOCUMENTS

| | | | |
|---|---|---|---|
| WO | WO2002076930 A2 * | 10/2002 | |
| WO | 2009114856 A2 | 9/2009 | |
| WO | 2011025167 A2 | 3/2011 | |
| WO | 2016156872 A1 | 10/2016 | |
| WO | 2018050656 A2 | 3/2018 | |
| WO | 2020257621 A1 | 12/2020 | |

OTHER PUBLICATIONS

Carpenter, Richard L., and Yesim Gökmen-Polar. "HSF1 as a Cancer Biomarker and Therapeutic Target." Current Cancer Drug Targets, vol. 19, No. 7, 2019, pp. 515-524. PubMed Central, https://doi.org/10.2174/1568009618666181018162117. (Year: 2019).*
Sharma, Chiranjeev, and Young Ho Seo. "Small Molecule Inhibitors of HSF1-Activated Pathways as Potential Next-Generation Anticancer Therapeutics." Molecules, vol. 23, No. 11, Oct. 2018, p. 2757. PubMed Central, https://doi.org/10.3390/molecules23112757. (Year: 2018).*
CN-103709097-A Machine Translation. Google Patents. Accessed Feb. 22, 2024 (Year: 2014).*
International Search Report and Written Opinion mailed Apr. 9, 2020 for corresponding International Patent Application No. PCT/US2019/065757, 6 pages.
Perveen, S. et al. (2014) Antiproliferative effects of novel urea derivatives against human prostate and lung cancer cells; and their inhibition of β-glucuronidase activity. Medicinal Chemistry Research. 23: 1099-1113.
Tarnow, P. et al. (2013) Effects of triclocarban on the transcription of estrogen, androgen and aryl hydrocarbon receptor responsive genes in human breast cancer cells. Toxicology in Vitro. 27(5): 1467-1475.
Papillon, J. et al. (2018) Discovery of Orally Active Inhibitors of Brahma Homolog (BRM)/SMARCA2 ATPase Activity for the Treatment of Brahma Related Gene 1 (BRG1)/SMARCA4-Mutant Cancers. Journal of Medical Chemistry. 61(22): 10155-10172.
Park, S.H. et al. (2019) Determinants of Ion-Transporter Cancer Cell Death. Chem. 5(8): 2079-2098.
Dong, B. et al. (2020) Targeting therapy-resistant prostate cancer via a direct inhibitor of the human heat shock transcription factor 1. Science Translational Medicine. 12(574): DOI: 10.1126/scitranslmed. abb5647.
Extended European Search Report for EP Application No. 19895895.1 mailed Jul. 21, 2022 (Applicant—Duke University) (46 Pages).

* cited by examiner

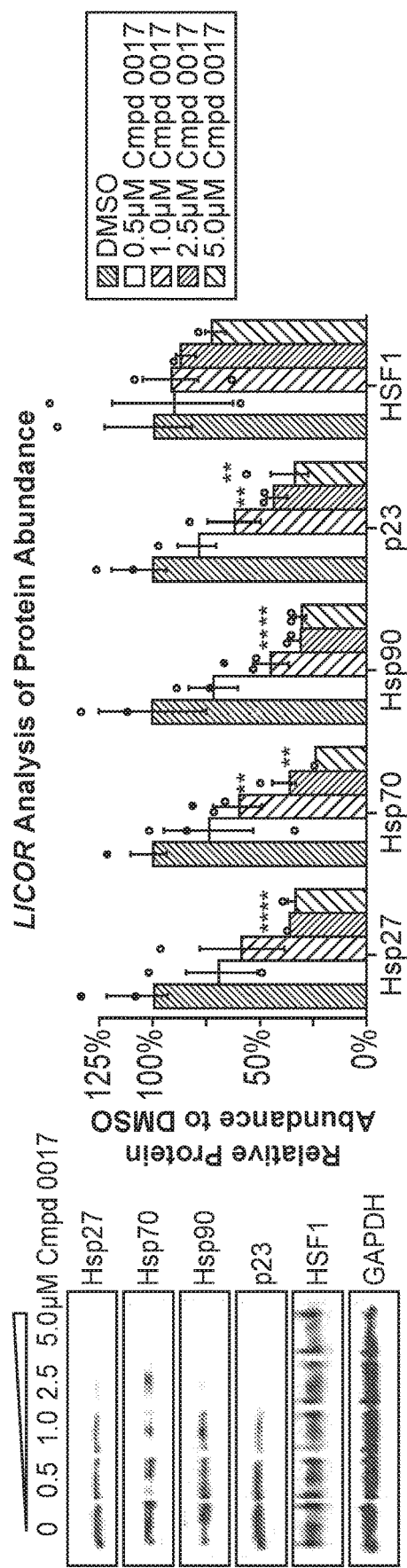
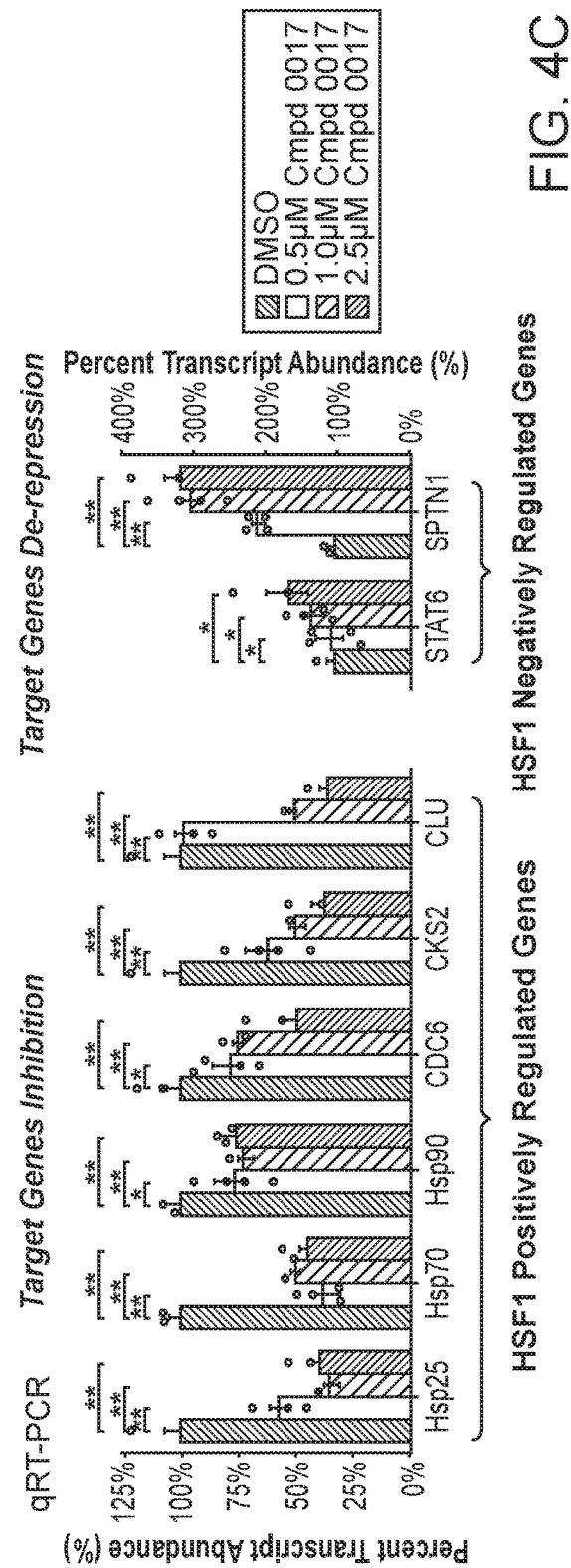
FIG. 4A
FIG. 4B
FIG. 4C

COMPOSITIONS AND METHODS FOR THE TREATMENT OF CANCER

CROSS-REFERENCE TO RELATED APPLICATIONS

This application is a U.S. National Phase Application of International Patent Application No. PCT/US2019/065757, which claims the benefit of U.S. Provisional Application No. 62/777,831, filed Dec. 11, 2018, each of which is incorporated herein by reference in their entirety.

STATEMENT AS TO FEDERALLY SPONSORED RESEARCH

This invention was made with government support under Grant CA014236 awarded by National Institutes of Health. The government has certain rights in the invention.

BACKGROUND OF DISCLOSURE

Field of the Invention

This disclosure relates to compounds, pharmaceutical compositions comprising them, and methods of using the compounds and compositions for treating diseases related to Heat Shock Transcription Factor 1 (HSF1) activity and/or function. More particularly, this disclosure relates to methods of inhibiting HSF1 activity with these compounds and pharmaceutical compositions thereof, and methods of treating diseases associated with HSF1 activity and/or function, such as cancer.

Background of the Disclosure

Therapies to prevent cancer cell survival, invasion and migration would be a major therapeutic breakthrough. Recent work has uncovered a critical role for the mammalian stress-responsive transcription factor, HSF1, in cancer cell initiation, proliferation, survival, invasion and metastasis. Furthermore, HSF1 was discovered as one of six metastasis-promoting genes in malignant melanoma. HSF1 is normally activated by cellular stresses that cause protein misfolding, activating the expression of protein chaperones that protect cells from protein damage. In many distinct cancers, however, HSF1 protein abundance and activity are dramatically elevated and HSF1 drives a program of gene expression that regulates pathways to support tumor cell initiation, growth, survival, invasion and metastasis, in both tumor cells and the stromal tissue (FIG. 1).

HSF1 itself is not an oncogene, but a broad range of cancer cells have a "non-oncogene addiction" to the pro-survival, pro-proliferative, pro-invasive and pro-metastatic functions of HSF1. Indeed, in melanoma, breast, hepatocellular carcinoma, prostate cancer and other cancers, HSF1 levels, and in particular nuclear HSF1 levels, inversely correlate with patient survival. In melanoma and other cancers, HSF1 protein levels are dramatically elevated, in part due to decreased levels of the F Box protein Fbxw7, which normally targets HSF1 for ubiquitin-mediated proteasomal degradation. Other mechanisms underlying the increase in HSF1 levels and activity, and particularly increased nuclear HSF1 levels, in a broad range of cancers are possible. Moreover, silencing of HSF1 expression by RNAi, shRNA, CRISPR-Cas9 or inactivation of the HSF1 gene by deletion in cultured cancer cells in vitro, or in mice, results in a marked reduction in cancer cell invasion and metastasis and in increased survival of mouse cancer models. While numerous reports have indicated that HSF1 is a promising therapeutic target in cancer, HSF1 inhibitors are not available for use in the clinic. Therefore, there exists a need to identify novel HSF1 inhibitors.

SUMMARY OF THE INVENTION

This disclosure relates to compounds, pharmaceutical compositions comprising them, and methods of using the compounds and compositions for treating diseases related to HSF1 activity and/or function. The present disclosure also provides method of using the compounds of the disclosure as therapeutic agents to treat a wide variety of diseases associated with HSF1 activity and/or function, such as cancer. Thus, the composition and methods of the present disclosure provide the needed, but until now unrealized, compositions and methods of treating a wide variety of diseases associated with HSF1 activity (e.g., cancer).

The inventors identified distinct molecules by using a specialized high throughput thermal denaturation profile screen to measure recombinant HSF1 DNA binding domain melting temperatures in the presence and in the absence of distinct compounds. The compounds were validated for HSF1 interaction in vitro by thermal denaturation profiling, and the compounds were found to either increase or decrease the HSF1 DNA binding domain melting temperature. The inventors further showed that these compounds inhibit the activity and/or function of human HSF1.

Thus, one aspect of the disclosure provides methods of treating cancer. Such methods include administering to a subject in need thereof an effective amount of a compound having the structure of Formula (I):

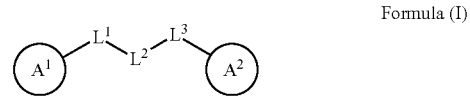

Formula (I)

or a pharmaceutically acceptable salt thereof, wherein:
ring $A^1$ is $C_1$-$C_6$alkyl, $C_3$-$C_6$cycloalkyl, $C_6$-$C_{10}$aryl, heteroaryl, or 3- to 10-membered heterocycloalkyl; each optionally substituted with 1-5 substituents independently selected from the group consisting of $R^{1a}$, —$OR^{1a}$, —$OC(O)R^{2a}$, —$NR^{2a}R^{2b}$, —$S(O)_{1\text{-}2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro;

$L^1$ is selected from —$(CH_2)_mNR^1$—, —$(CH_2)_mS$—, —$(CH_2)_mO$—, —$C(O)$—, —$C(O)O$—, —$C(O)NR^1$—, —$C(=NR^1)$—, —$CR^2=N$—, $C_1$-$C_6$alkyl, $C_2$-$C_6$alkenyl, $C_2$-$C_6$heteroalkyl, $C_3$-$C_6$cycloalkyl, $C_6$-$C_{10}$aryl, 5- to 10-membered heteroaryl, and 3- to 10-membered heterocycloalkyl; each optionally substituted with 1-5 substituents independently selected from the group consisting of $R^{1a}$, —$OR^{1a}$, —$OC(O)R^{2a}$, —$NR^{2a}R^{2b}$, —$S(O)_{1\text{-}2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro;

$L^2$ is absent or selected from —$C(O)$—, —$C(=NR^1)$—, —$S$—, —$O$—, —$C(O)O$—, —$C(O)NR^1$—, —$(CH_2)_mNR^1$—, —$S(O)$—, —$SO_2$—, $C_1$-$C_6$alkyl, $C_2$-$C_6$alkenyl, $C_2$-$C_6$heteroalkyl, $C_3$-$C_6$cycloalkyl, $C_6$-$C_{10}$aryl, 5- to 10-membered heteroaryl, and 3- to 10-membered heterocycloalkyl; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro;

$L^3$ is absent or selected from —$(CH_2)_nNR^1$—, —$(CH_2)_nS$—, —$(CH_2)_nO$—, —$C(O)$—, —$C(O)NR^1$—, —$NHC(O)NH$—, —$N=CR^2$—, $C_1$-$C_6$alkyl, $C_2$-$C_6$alkenyl, $C_2$-$C_6$heteroalkyl, $C_3$-$C_6$cycloalkyl, $C_6$-$C_{10}$aryl, 5- to 10-membered heteroaryl, and 3- to 10-membered heterocycloalkyl; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro; and ring $A^2$ is a $C_3$-$C_6$cycloalkyl, $C_6$-$C_{10}$aryl, heteroaryl, or 3- to 10-membered heterocycloalkyl; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro;

wherein each $R^1$ is independently selected from hydrogen; hydroxy; cyano; substituted or unsubstituted $C_1$-$C_6$alkyl; substituted or unsubstituted $C_2$-$C_6$alkenyl; substituted or unsubstituted $C_1$-$C_6$heteroalkyl; substituted or unsubstituted $C_3$-$C_6$cycloalkyl; substituted or unsubstituted $C_6$-$C_{10}$aryl; substituted or unsubstituted 5 to 10 membered heteroaryl and substituted or unsubstituted 3-10 membered heterocycloalkyl;

each $R^2$ is independently selected from hydrogen; halogen; cyano; nitro; substituted or unsubstituted $C_1$-$C_6$alkyl; substituted or unsubstituted $C_2$-$C_6$alkenyl; substituted or unsubstituted $C_1$-$C_6$heteroalkyl; substituted or un substituted $C_3$-$C_6$cycloalkyl; substituted or unsubstituted $C_6$-$C_{10}$aryl; substituted or unsubstituted 5 to 10 membered heteroaryl and substituted or unsubstituted 3-10 membered heterocycloalkyl;

each $R^{1a}$ is independently selected from unsubstituted $C_1$-$C_6$alkyl; $C_1$-$C_6$alkyl substituted with halogen, amine, cyano, oxo, or nitro; $C_2$-$C_6$alkene; $C_2$-$C_6$alkenyl; unsubstituted $C_3$-$C_6$ cycloalkyl; $C_3$-$C_6$ cycloalkyl substituted with $C_1$-$C_4$ alkyl, halogen, amine, cyano, oxo, or nitro; unsubstituted $C_6$-$C_{10}$aryl; $C_6$-$C_{10}$aryl substituted with $C_1$-$C_4$ alkyl, halogen, amine, cyano, oxo, or nitro; unsubstituted heteroaryl; heteroaryl substituted with $C_1$-$C_4$ alkyl, halogen, amine, cyano, oxo, or nitro; unsubstituted 3- to 10-membered heterocycloalkyl; and 3- to 10-membered heterocycloalkyl substituted with $C_1$-$C_4$ alkyl, halogen, amine, cyano, oxo, or nitro;

$R^{2a}$ and $R^{2b}$ are each independently selected from hydrogen, hydroxy, cyano, —COOH; —$C(O)(OC_1$-$C_6$alkyl); unsubstituted $C_1$-$C_6$alkyl; $C_1$-$C_6$alkyl substituted with halogen, amine, cyano, oxo, or nitro; $C_2$-$C_6$alkene; $C_2$-$C_6$alkenyl; unsubstituted $C_3$-$C_6$ cycloalkyl; $C_3$-$C_6$ cycloalkyl substituted with $C_1$-$C_4$ alkyl, halogen, amine, cyano, oxo, or nitro; unsubstituted $C_6$-$C_{10}$aryl; $C_6$-$C_{10}$aryl substituted with $C_1$-$C_4$ alkyl, halogen, amine, cyano, oxo, or nitro; unsubstituted heteroaryl; heteroaryl substituted with $C_1$-$C_4$ alkyl, halogen, amine, cyano, oxo, or nitro; unsubstituted 3- to 10-membered heterocycloalkyl; and 3- to 10-membered heterocycloalkyl substituted with $C_1$-$C_4$ alkyl, halogen, amine, cyano, oxo, or nitro;

m is an integer in the range of 0-3; and n is an integer in the range of 0-3.

Another aspect of the disclosure provides compounds of Formula (I). In certain embodiments, the disclosure provides compounds as provided in Table 1 and Table 2.

Another aspect of the disclosure provides a pharmaceutical composition comprising a compound of the disclosure and a pharmaceutically acceptable excipient and/or carrier.

In certain embodiments, the compounds and/or compositions of the disclosure inhibit the activity and/or function of human HSF1. The activity is not limited to a particular type of HSF. In some embodiments, the HSF is HSF1, HSF2, or HSF4. The compounds and/or compositions are not limited by the manner in which they result in HSF inhibition. In some embodiments, HSF inhibition includes, but is not limited to, inhibition of HSF1 homo-trimerization, inhibition of HSF target gene expression (e.g., Heat Shock Elements), inhibition of HSF target protein expression (e.g., Heat Shock Proteins), inhibition of HSF1-mediated genome-wide transcriptional regulation, and/or inhibition of protein chaperone activity (e.g., decreased protein folding, decreased protein solubilization, protein degradation). In certain embodiments, the inhibition of the activity and/or function of HSF1 is by binding of the compound directly to HSF1. For example, in certain embodiments, the binding of the compound stabilizes the HSF1 protein. In certain embodiments, the binding of the compound destabilizes the HSF1 protein. In certain embodiments, the binding of the compound increases the melting temperature of the HSF1 protein by at least 1° C. when compared with the melting temperature of the HSF1 protein prior to binding; or the binding of the compound decreases the melting temperature of the HSF1 protein by at least 1° C. when compared with the melting temperature of the HSF1 protein prior to binding.

BRIEF DESCRIPTION OF THE DRAWINGS

The accompanying drawings are included to provide a further understanding of the compositions and methods of the disclosure, and are incorporated in and constitute a part of this specification. The drawings illustrate one or more embodiments) of the disclosure and, together with the description, serve to explain the principles and operation of the disclosure.

FIG. 4A shows that Compound 0017 inhibits HSF1 function in malignant prostate cancer cells. In the malignant prostate cancer cell line C4-2, compound 0017 dose-dependently reduced the steady-state protein level of the molecular chaperones Hsp27, Hsp70, Hsp90 and p23, whose expression is activated by HSF1. FIG. 4B shows LI-COR® quantification of the immunoblot blot in A shows statistically significant, dose-dependent decreases in the HSF1-dependent expression of protein chaperone levels. FIG. 4C shows that, in C4-2 cells, Compound 0017 dose-dependently repressed the expression of HSF1 positively regulated transcripts, and de-repressed HSF1 negatively regulated transcripts, demonstrating that Compound 0017 inhibits both the activation and repression functions of HSF1. *=P<0.01; **=P<0.01 in accordance with one embodiment of the present disclosure.

DETAILED DESCRIPTION OF THE INVENTION

Figure 1:
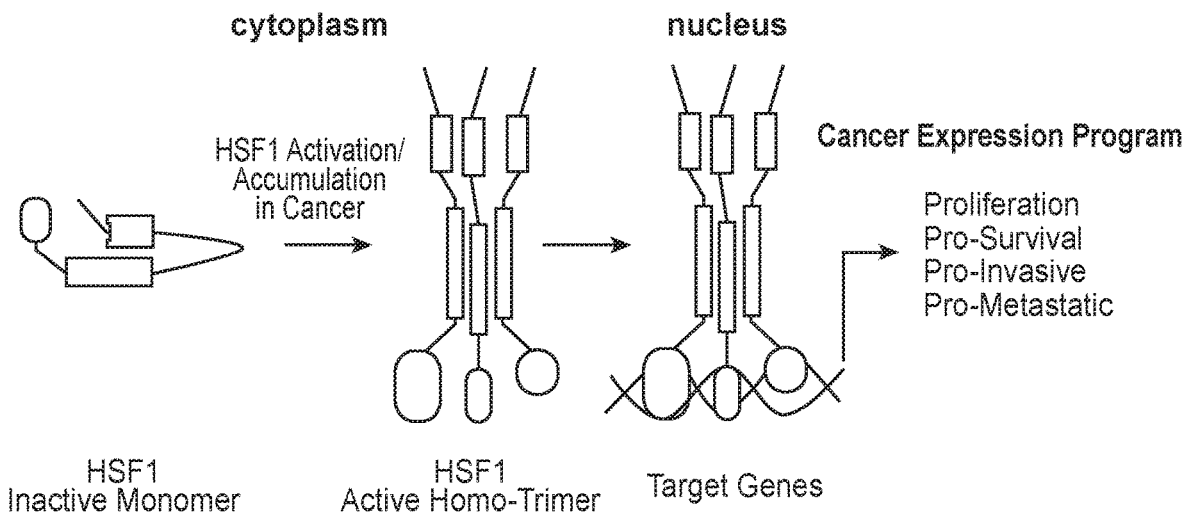
FIG. 1 is a model that shows HSF1 protein levels accumulate both in the cytoplasm and the nucleus, and HSF1 is activated in a wide range of cancers to regulate (either activate, repress, or both) transcription of genes involved in cancer cell initiation, proliferation, survival, invasion and metastasis. Genetic knock down or knock out of HSF1 illustrate that HSF1 is a potential target to treat a wide range of cancers.

Before the disclosed processes and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

Method of Treatment

One aspect of the disclosure provides methods of treating cancer. Such methods include administering to a subject in need thereof an effective amount of a compound of the disclosure (e.g., a compound of Formula (I)) or a pharmaceutical composition of the disclosure as provided herein.

The term "disease" as used herein includes, but is not limited to, any abnormal condition and/or disorder of a structure or a function that affects a part of an organism. It may be caused by an external factor, such as an infectious disease, or by internal dysfunctions, such as cancer, cancer metastasis, and the like.

As is known in the art, a cancer is generally considered as uncontrolled cell growth. The methods of the present invention can be used to treat any cancer, and any metastases thereof, that is characterized by the activation and/or over-expression of HSF1. Examples include, but are not limited to, breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, leukemia (including but not limited to acute lymphoblastic leukemia and acute myeloid leukemia), sarcoma, carcinoma, stromal cancer, testicular cancer, neurofibroma, hepatocellular carcinoma, lymphoma, Ewing sarcoma and peripheral neuroepithelioma, and combinations thereof.

In some embodiments, the cancer is leukemia, non-small cell lung cancer, colon cancer, CNS cancer, ovarian cancer, renal cancer, breast cancer, prostate cancer and melanoma. In some embodiments, the cancer is prostate cancer or melanoma. In some embodiments, the cancer is prostate cancer. In some embodiments, the cancer is melanoma.

Effective amounts of a compound, composition and/or pharmaceutical composition as provided herein can be determined by a physician with consideration of individual differences in age, weight, tumor size, extent of infection or metastasis, and condition of the patient (subject). The compositions may also be administered multiple times at these dosages. The optimal dosage and treatment regime for a particular patient can readily be determined by one skilled in the art of medicine by monitoring the patient for signs of disease and adjusting the treatment accordingly.

Various delivery systems are known and can be used to administer therapeutic agents (e.g., exemplary compounds, compositions and/or pharmaceutical compositions as described herein) of the present disclosure, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In some embodiments, it may be desirable to administer the pharmaceutical compositions of the present disclosure locally to the area in need of treatment; this may be achieved by, for example, and not by way of limitation, local infusion during surgery, injection, or by means of a catheter.

It is contemplated that the compounds, compositions and/or pharmaceutical compositions of the disclosure can be administered to subjects or individuals susceptible to or at risk of developing pathological growth of target cells and correlated conditions (e.g., at risk of developing a cancer). When the compounds, compositions and/or pharmaceutical compositions is administered to a subject such as a mouse, a rat or a human patient, the compounds, compositions and/or pharmaceutical compositions can be added to a pharmaceutically acceptable carrier and/or excipient and systemically or topically administered to the subject. To determine patients that can be beneficially treated, a tissue sample may be removed from the patient and the cells assayed for sensitivity to the agent.

The compounds, compositions and/or pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders. In addition to an agent of the present invention, the pharmaceutical compositions can also contain other pharmaceutically active compounds or a plurality of compounds of the invention.

More particularly, a compounds, compositions and/or pharmaceutical compositions according to the present disclosure, also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the compounds, compositions and/or pharmaceutical compositions should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the composition may be maintained by a continuous infusion to provide a therapeutic amount of the active ingredient within disease tissue. The use of operative combinations is contemplated to provide therapeutic combinations requiring a lower total dosage of each component agent than may be required when each individual therapeutic compound or drug is used alone, thereby reducing adverse effects.

Therapeutic amounts are empirically determined and vary with the pathology being treated, the subject being treated and the efficacy and toxicity of the compounds, compositions and/or pharmaceutical compositions. When delivered to an animal, the method is useful to further confirm efficacy of the compounds, compositions and/or pharmaceutical compositions.

Suitable dosage formulations and methods of administering the compounds, compositions and/or pharmaceutical compositions are readily determined by those of skill in the art. Preferably, the compounds, compositions and/or pharmaceutical compositions are administered at about 0.01 mg/kg to about 200 mg/kg, more preferably at about 0.1 mg/kg to about 100 mg/kg, even more preferably at about 0.5 mg/kg to about 50 mg/kg. When the compositions described herein are co-administered with another agent (e.g., as sensitizing agents), the effective amount may be less than when the agent is used alone.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

An effective amount of the compounds, compositions and/or pharmaceutical compositions described herein may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the composition. Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The methods of the present disclosure are not limited to dosing intervals that are spaced equally in time, but encompass doses at non-equal intervals, such as a priming schedule consisting of administration at 1 day, 4 days, 7 days, and 25 days, just to provide a non-limiting example.

An effective amount for a particular subject/patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

A dosing schedule of, for example, once/week, twice/week, three times/week, four times/week, five times/week, six times/week, seven times/week, once every two weeks, once every three weeks, once every four weeks, once every five weeks, and the like, is available for the methods provided herein. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The present disclosure also includes methods involving co-administration of the compounds, compositions and/or pharmaceutical compositions described herein with one or more additional active agents (e.g., additional chemotherapeutic/anti-cancer agents, biological agents, chemical agents, radiation, and the like). Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

In one embodiment, the present disclosure provides methods for enhancing prior art therapies and/or pharmaceutical compositions by co-administering a compound, composition and/or pharmaceutical composition according to the present disclosure. The pharmaceutical formulations and modes of administration may be any of those described above. In addition, the two or more co-administered chemotherapeutic/anti-cancer agents, chemical agents, biological agents or radiation may each be administered using different modes or different formulations. Co-administration need not to refer to administration at the same time in an individual, but rather may include administrations that are spaced by hours or even days, weeks, or longer, as long as the administration of multiple therapeutic agents is the result of a single treatment plan. By way of example, the co-administration may comprise administering the compounds, compositions and/or pharmaceutical compositions according to the present disclosure before, after, or at the same time as the one or more additional therapeutics. In one possible treatment schedule, the compounds, compositions and/or pharmaceutical compositions of the present disclosure may be given as an initial dose in a multi-day protocol, with one or more additional therapeutics given on later administration days; or the one or more additional therapeutics are given as an initial dose in a multi-day protocol, with the compounds, compositions and/or pharmaceutical compositions of the present disclosure given on later administration days. On another hand, one or more additional therapeutic agents and the compounds, compositions and/or pharmaceutical compositions of the present disclosure may be administered on alternate days in a multi-day protocol. In still another example, a mixture of one or more additional therapeutics and the compounds, compositions and/or pharmaceutical compositions of the present disclosure may be administered to reduce the presence of cancer in the subject. This is not meant to be a limiting list of possible administration protocols.

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

Formulations of therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

The Compounds of the Disclosure

As provided above, some embodiments relate to a compound having the structure of Formula (I) as described herein.

In some embodiments, the compounds of formula (I) as otherwise described herein are those wherein $A^1$ is $C_3$-$C_6$cycloalkyl, $C_6$-$C_{10}$aryl, heteroaryl, or 3- to 10-membered heterocycloalkyl; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro. In certain embodiments, $A^1$ is $C_6$-$C_{10}$aryl, heteroaryl, or 3- to 10-membered heterocycloalkyl; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}$ $R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro. In certain embodiments, $A^1$ is selected from phenyl, cyclohexyl, thiophene, pyridine, piperine, quinoline, isoqionoline, triazole, imidazole, pyrazole, oxozole, thiazole, isoxazole, benzimidazole, diazine, morpholine, oxane, oxepane, benzo(c)[1,2,5]oxadiazole, benzoisoxadiazole, benzothiadiazole, indazole, indole, chromene, naphthalene, and aziridine; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro. Yet, in certain embodiments, $A^1$ is selected from phenyl, cyclohexyl, pyridine, diazine, diazole, triazole, benzo(c)[1,2,5]oxadiazole, or thiophene; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro. In certain embodiments, $A^1$ is phenyl or pyridine; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro.

Another embodiment of the disclosure provides compounds of formula (I) as otherwise described herein which are of Formula (II)

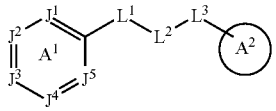

Formula (II)

wherein
$J^1$, $J^2$, $J^3$, $J^4$, and $J^5$ are independently selected from N and $CR^{3a}$, provided at least two of $J^1$ $J^2$, $J^3$, $J^4$, and $J^5$ are not N,
wherein each $R^{3a}$ is independent selected from hydrogen, $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro.

In certain embodiments of the disclosure, the compounds of formula (II) as otherwise described herein are those wherein each one of $J^1$, $J^2$, $J^3$, $J^4$, and $J^5$ are $CR^{3a}$ (e.g., $A^1$ is a phenyl ring substituted with 5 $R^{3a}$). In certain embodiments, four of $J^1$, $J^2$, $J^3$, $J^4$, and $J^5$ are $CR^{3a}$, and remaining $J^1$, $J^2$, $J^3$, $J^4$, or $J^5$ is N.

In certain embodiments of the disclosure, the compounds of formula (I)-(II) as otherwise described herein are those wherein $A^2$ is $C_6$-$C_{10}$aryl, heteroaryl, or 3- to 10-membered heterocycloalkyl; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro. In certain embodiments, $A^2$ is $C_6$-$C_{10}$aryl or heteroaryl; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro. In certain embodiments, $A^2$ is selected from phenyl, cyclohexyl, thiophene, pyridine, pipeline, quinoline, isoqionoline, triazole, imidazole, pyrazole, oxozole, thiazole, isoxazole, benzimidazole, diazine, morpholine, oxane, oxepane, benzo(c)[1,2,5]oxadiazole, benzoisoxadiazole, benzothiadiazole, indazole, indole, chromene, naphthalene, and aziridine; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro. In certain embodiments, $A^2$ is phenyl, cyclohexyl, pyridine, diazine, diazole, triazole, benzo(c)[1,2,5]oxadiazole, or thiophene; each optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro. In certain embodiments, $A^2$ is phenyl optionally substituted with 1-5 substituents independently selected from the group consisting of $R^{1a}$, —$OR^{1a}$, —$OC(O)R^{2a}$, —$NR^{2a}R^{2b}$, —$S(O)_{1-2}R^{2a}$, —$SO_2NR^{2a}R^{2b}$, —$NR^{2a}SO_2R^{2b}$, —$C(O)R^{2b}$, —$C(O)OR^{2a}$, —$C(O)NR^{2a}R^{2b}$, —$NR^{2a}C(O)R^{2b}$, —$NR^{2a}C(O)OR^{2b}$, halogen, cyano, oxo, and nitro.

Another embodiment of the disclosure provides compounds of formula (I)-(II) as otherwise described herein wherein $L^1$ is —$(CH_2)_mNR^1$—, —O—, —C(O)—, —C(O)O—, —C(O)NR^1$—, —$C(=NR^1)$—, —$CR^2=N$—, or $C_1$-$C_6$alkyl. In certain embodiments, $L^1$ is —$(CH_2)_mNR^1$— or —O—. In certain embodiments, $L^1$ is —$(CH_2)_mNR^1$—. In certain embodiments, $L^1$ is —$NR^1$—; or wherein $L^1$ is —NH—.

Another embodiment of the disclosure provides compounds of formula (I)-(II) as otherwise described herein wherein $L^3$ is —$(CH_2)_nNR^1$—, —$(CH_2)_nS$—, —$(CH_2)_nO$—, —C(O)—, —C(O)NR^1$—, —NHC(O)NH—, —N=CR^2$—, or $C_1$-$C_6$alkyl. In certain embodiments, $L^3$ is —$(CH_2)_mNR^1$— or —O—. In certain embodiments, $L^3$ is —$(CH_2)_nNR^1$—, In certain embodiments, $L^3$ is —$NR^1$—. In certain embodiments, $L^3$ is —NH—.

In certain embodiments of the disclosure, the compounds of formula (I)-(II) as otherwise described herein are those wherein $L^2$ is —C(O)—, —$C(=NR^{2a})$—, unsubstituted or substituted 3-10 membered heterocycloalkyl, or unsubstituted or substituted 5-10 membered heteroaryl. In certain embodiments, $L^2$ is substituted or unsubstituted $C_3$-$C_6$ cycloalkyl. In certain embodiments, $L^2$ is $C_3$-$C_6$ cycloalkyl substituted with one or more of $C_1$-$C_4$ alkyl, halogen, amine, cyano, oxo, and nitro. In certain embodiments, $L^2$ is $C_3$-$C_6$ cycloalkyl substituted with $C_1$-$C_4$ alkyl, halogen, amine, cyano, oxo, or nitro. In certain embodiments, $L^2$ is cyclobutene substituted with one or more oxo. For example, in certain embodiments, $L^2$ is

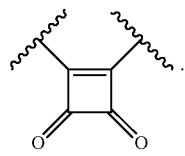 [SMILES: *c1c(*)c(=O)c1=O]

In certain embodiments of the disclosure, the compounds of formula (I)-(II) as otherwise described herein are those wherein L² is —C(O)— or —C(=NR²ᵃ)—. For example, in certain embodiments, L² is —C(O)—. In certain embodiments, L² is —C(O)—, —C(=NH)—, —C(=NCN)—,

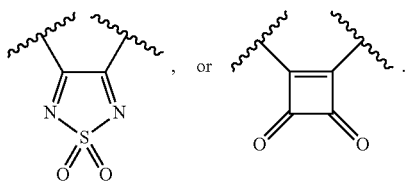 [SMILES: *C1=NS(=O)(=O)N=C1* ; *c1c(*)c(=O)c1=O]

Another embodiment of the disclosure provides compounds of formula (I)-(II) as otherwise described herein which are of Formula (III):

Formula (III)

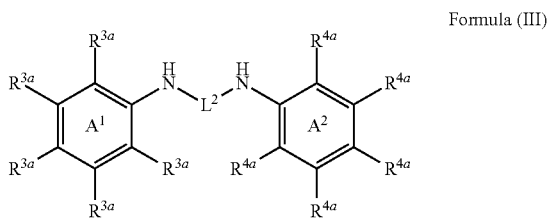

wherein
each R³ᵃ is independent selected from hydrogen, R¹ᵃ, —OR¹ᵃ, —OC(O)R²ᵃ, —NR²ᵃR²ᵇ, —S(O)₁₋₂R²ᵃ, —SO₂NR²ᵃR²ᵇ, —NR²ᵃSO₂R²ᵇ, —C(O)R²ᵇ, —C(O)OR²ᵃ, —C(O)NR²ᵃR²ᵇ, —NR²ᵃC(O)R²ᵇ, —NR²ᵃC(O)OR²ᵇ, halogen, cyano, oxo, and nitro; and
each R⁴ᵃ is independent selected from hydrogen, R¹ᵃ, —OR¹ᵃ, —OC(O)R²ᵃ, —NR²ᵃR²ᵇ, —S(O)₁₋₂R²ᵃ, —SO₂NR²ᵃR²ᵇ, —NR²ᵃSO₂R²ᵇ, —C(O)R²ᵇ, —C(O)OR²ᵃ, —C(O)NR²ᵃR²ᵇ, —NR²ᵃC(O)R²ᵇ, —NR²ᵃC(O)OR²ᵇ, halogen, cyano, oxo, and nitro.

In certain embodiments of the disclosure, the compounds of formula (III) as otherwise described herein are those wherein each R³ᵃ is independent selected from hydrogen, R¹ᵃ, —OR¹ᵃ, —NR²ᵃR²ᵇ, —C(O)R²ᵇ, —C(O)OR²ᵃ, —C(O)NR²ᵃR²ᵇ, halogen, cyano, oxo, and nitro. For example, in certain embodiments, each R³ᵃ is independently selected from hydrogen, halogen, C₁-C₄ alkyl, halogenated C₁-C₄ alkyl, nitro, cyano, and —COOH; or each R³ᵃ is independently selected from hydrogen, C₁-C₄ alkyl, or halogen; or each R³ᵃ is independently selected from hydrogen, methyl, or halogen. In certain embodiments, at least one R³ᵃ is independently methyl or halogen (e.g., fluorine) and the remaining R³ᵃ are hydrogen. For example, the ring A¹ may be

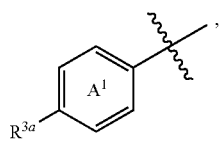

where R³ᵃ is methyl or halogen (e.g., fluorine).
In certain embodiments of the disclosure, the compounds of formula (III) as otherwise described herein are those wherein each R⁴ᵃ is independent selected from hydrogen, R¹ᵃ, —OR¹ᵃ, —NR²ᵃR²ᵇ, —S(O)₁₋₂R²ᵃ, —C(O)R²ᵇ, —C(O)OR²ᵃ, —C(O)NR²ᵃR²ᵇ, halogen, cyano, oxo, and nitro. For example, in certain embodiments, each R⁴ᵃ is independently selected from hydrogen, halogen, C₁-C₄ alkyl, halogenated C₁-C₄ alkyl, —S(O₂)(halogenated C₁-C₄ alkyl), nitro, cyano, and —COOH; or each R⁴ᵃ is independently selected from hydrogen, halogen, halogenated C₁-C₄ alkyl, —S(O₂)(halogenated C₁-C₄ alkyl), nitro, cyano, and —COOH; or each R⁴ᵃ is independently selected from hydrogen, halogen, C₁-C₄ alkyl, halogenated C₁-C₄ alkyl, nitro, and cyano. In certain embodiments, at least one R⁴ᵃ is independently halogen, C₁-C₄ alkyl, halogenated C₁-C₄ alkyl, nitro, and cyano; or at least one R⁴ᵃ is independently halogen, C₁-C₄ alkyl, halogenated C₁-C₄ alkyl, nitro, and cyano, and the remaining R⁴ᵃ are hydrogen. For example, the ring A² may be

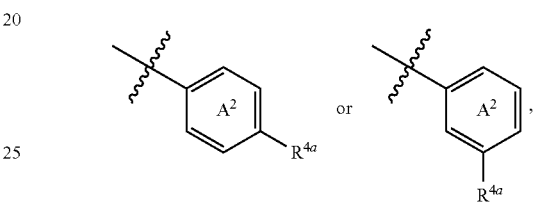

where R⁴ᵃ is independently halogen, C₁-C₄ alkyl, halogenated C₁-C₄ alkyl, nitro, and cyano.

Certain embodiments of the disclosure provide compounds of formula (I) wherein
ring A¹ is a C₆-C₁₀aryl, C₃₋₁₀ cycloalkyl, 5-10 membered heteroaryl, or 3- to 10-membered heterocycloalkyl; each substituted with one or more substituents selected from halogen, cyano, nitro, —COOH, C₁-C₆alkyl, halogenated C₁-C₆alkyl, —R¹ᵃ, —NHCOC₁-C₆alkyl, and —OS(O₂)OH;
ring A² is a C₆-C₁₀aryl, C₃₋₁₀ cycloalkyl, 5-10 membered heteroaryl, or 3- to 10-membered heterocycloalkyl; each substituted with one or more substituents selected from halogen, cyano, nitro, —COOH, C₁-C₆alkyl, halogenated C₁-C₆alkyl, —R¹ᵃ, —NHCOC₁-C₆alkyl, —S(O₂)CF₃, —NHC(O)CH₃, —OS(O₂)OH; or —COO(C₁₋₈ alkyl);
L¹-L²-L³- represents a bond, —NR¹—R³—NR¹—, —S—, —O—, —C(O)—, —C(O)O—, —C(O)NR¹—, —CR²=N—NHCO—, C₁-C₆alkyl, or 3-10 membered heterocycloalkyl;
wherein
each R¹ is independently selected from hydrogen; hydroxy, cyano; C₁-C₆alkyl; C₃-C₆cycloalkyl; C₆-C₁₀aryl; 5- to 10-membered heteroaryl; and 3- to 10-membered heterocycloalkyl;
each R² is independently selected from hydrogen; halogen; cyano; nitro; C₁-C₆alkyl; C₃-C₆cycloalkyl; C₆-C₁₀aryl; 5- to 10-membered heteroaryl; and 3- to 10-membered heterocycloalkyl;
R³ is selected from —C(O)—, —C(=N—CN)—, —C(=NH)—, substituted or unsubstituted C₃-C₆cycloalkyl, substituted or unsubstituted C₆-C₁₀aryl, substituted unsubstituted 5- to 10-membered heteroaryl, and substituted or unsubstituted 3-10 membered heterocycloalkyl; and
each R¹ᵃ is independently selected from unsubstituted C₁-C₆alkyl; C₁-C₆alkyl substituted with halogen, amine, cyano, oxo, or nitro; C₂-C₆alkene;

$C_2$-$C_6$alkenyl; unsubstituted $C_3$-$C_6$ cycloalkyl; $C_3$-$C_6$ cycloalkyl substituted with $C_1$-$C_4$ alkyl, halogen, amine, cyano, oxo, or nitro; unsubstituted $C_6$-$C_{10}$aryl; $C_6$-$C_{10}$aryl substituted with $C_1$-$C_4$ alkyl, halogen, amine, cyano, oxo, or nitro; unsubstituted heteroaryl; heteroaryl substituted with $C_1$-$C_4$ alkyl, halogen, amine, cyano, oxo, or nitro; unsubstituted 3- to 10-membered heterocycloalkyl; and 3- to 10-membered heterocycloalkyl substituted with $C_1$-$C_4$ alkyl, halogen, amine, cyano, oxo, or nitro.

In such embodiments of the disclosure, for example, $A^1$ is a phenyl, thiophene, tetrahydrofuran, quinolone, or dihydroquinoline, each substituted with one or more substituents selected from halogen, cyano, nitro, —COOH, $C_1$-$C_6$alkyl, halogenated $C_1$-$C_6$alkyl, —$R^{1a}$, —NHCOC$_1$-$C_6$alkyl, and —OS($O_2$)OH. In certain embodiments, $A^1$ is $C_6$-$C_{10}$aryl substituted with one or more substituents selected from halogen, cyano, nitro, —COOH, $C_1$-$C_6$alkyl, halogenated $C_1$-$C_6$alkyl, —$R^{1a}$, —NHCOC$_1$-$C_6$alkyl, and —OS($O_2$)OH.

Another embodiment of the disclosure provides compounds of formula (I) as otherwise described herein which are of Formula (IV)

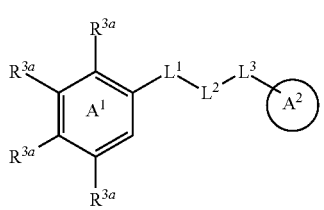

Formula (IV)

wherein each $R^{3a}$ is independently selected from hydrogen, halogen, cyano, nitro, —COOH, $C_1$-$C_6$alkyl, halogenated $C_1$-$C_6$alkyl, —$R^{1a}$, —NHCOC$_1$-$C_6$alkyl, and —OS($O_2$)OH, provided at least one of $R^{3a}$ is not hydrogen.

In certain embodiments of the disclosure, the compounds of formula (I)-(IV) as otherwise described herein are those wherein $A^2$ is a phenyl, thiophene, tetrahydrofuran, quinolone, dihydroquinoline, or isoindole; each substituted with one or more substituents selected from halogen, cyano, nitro, —COOH, $C_1$-$C_6$alkyl, halogenated $C_1$-$C_6$alkyl, —$R^{1a}$, —NHCOC$_1$-$C_6$alkyl, —S($O_2$)CF$_3$, —NHC(O)CH$_3$, —OS($O_2$)OH; or —COO($C_{1-8}$ alkyl). In certain embodiments, $A^2$ is $C_6$-$C_{10}$aryl substituted with one or more substituents selected from halogen, cyano, nitro, —COOH, $C_1$-$C_6$alkyl, halogenated $C_1$-$C_6$alkyl, —$R^{1a}$, —NHCOC$_1$-$C_6$alkyl, —S($O_2$)CF$_3$, —NHC(O)CH$_3$, —OS($O_2$)OH; or —COO($C_{1-8}$ alkyl). In certain embodiments, $A^2$ is phenyl substituted with one or more substituents selected from halogen, cyano, nitro, —COOH, $C_1$-$C_6$alkyl, halogenated $C_1$-$C_6$alkyl, —$R^{1a}$, —NHCOC$_1$-$C_6$alkyl, —S($O_2$)CF$_3$, —NHC(O)CH$_3$, —OS($O_2$)OH; or —COO($C_{1-8}$ alkyl).

Another embodiment of the disclosure provides compounds of formula (I) as otherwise described herein which are of Formula (V)

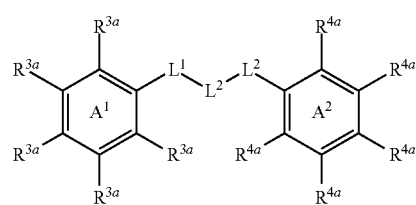

Formula (V)

wherein
each $R^{3a}$ is independently selected from hydrogen, halogen, cyano, nitro, —COOH, $C_1$-$C_6$alkyl, halogenated $C_1$-$C_6$alkyl, —$R^{1a}$, —NHCOC$_1$-$C_6$alkyl, and —OS($O_2$)OH, provided at least one of $R^{3a}$ on $A^1$ is not hydrogen; and
each $R^{4a}$ is independently selected from hydrogen, halogen, cyano, nitro, —COOH, $C_1$-$C_6$alkyl, halogenated $C_1$-$C_6$alkyl, —$R^{1a}$, —NHCOC$_1$-$C_6$alkyl, and —OS($O_2$)OH, provided at least one of $R^{4a}$ on $A^2$ is not hydrogen.

Another embodiment of the disclosure provides compounds of formula (I) as otherwise described herein wherein one of $A^1$ and $A^2$ is substituted $C_6$-$C_{10}$ aryl and the other is substituted 5- to 10-membered heteroaryl.

Another embodiment of the disclosure provides compounds of formula (I) as otherwise described herein wherein one of $A^1$ and $A^2$ is substituted 3- to 10-membered heterocycloalkyl and the other is substituted $C_{3-10}$cycloalkyl.

Another embodiment of the disclosure provides compounds of formula (I) as otherwise described herein wherein $A^1$ and $A^2$ are each independently substituted 5- to 10-membered heteroaryl.

Another embodiment of the disclosure provides compounds of formula (I) as otherwise described herein wherein $A^1$ and $A^2$ are each independently substituted 3- to 10-membered heterocycloalkyl.

Another embodiment of the disclosure provides compounds of formula (I)-(II) and (IV)-(V) as otherwise described herein wherein -$L^1$-$L^2$-$L^3$- is —NR$^1$-$R^3$—NR$^1$—, In some embodiments, each $R^1$ is independently hydrogen or $C_1$-$C_6$alkyl; or wherein each $R^1$ is independently hydrogen or methyl; or wherein both $R^1$ are hydrogen; or wherein one of $R^1$ is hydrogen and the other is methyl. In some embodiments, $R^3$ is —C(O)—, —C(=N—CN)—, —C(=NH)—,

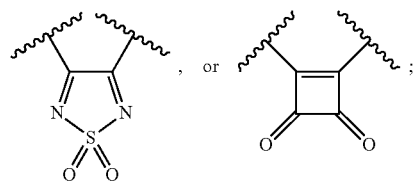 [SMILES: *C1=NS(=O)(=O)N=C1* ; *c1c(*)c(=O)c1=O]

or wherein $R^3$ is —C(O)—; or wherein $R^3$ is —C(=N—CN)—; or wherein $R^3$ is —C(=NH)—; or wherein $R^3$ is substituted or unsubstituted $C_3$-$C_6$cycloalkyl

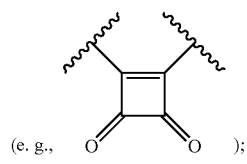

(e. g., or wherein $R^3$ is substituted or unsubstituted 5- to 10-membered heteroaryl (e.g., 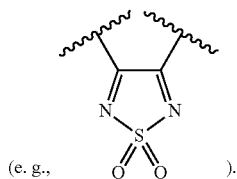 [SMILES: *C1=NS(=O)(=O)N=C1*] ).

Another embodiment of the disclosure provides compounds of formula (III) as otherwise described herein wherein each $R^{3a}$ is independently selected from hydrogen, halogen, cyano, nitro, —COOH, $C_1$-$C_6$alkyl, halogenated $C_1$-$C_6$alkyl, —$R^{1a}$, —NHCOC$_1$-$C_6$alkyl, and —OS(O$_2$)OH, provided at least one of $R^{3a}$ on $A^1$ is not hydrogen; and each $R^{4a}$ is independently selected from hydrogen, halogen, cyano, nitro, —COOH, $C_1$-$C_6$alkyl, halogenated $C_1$-$C_6$alkyl, —$R^{1a}$, —NHCOC$_1$-$C_6$alkyl, and —OS(O$_2$)OH, provided at least one of $R^{4a}$ on $A^2$ is not hydrogen. In certain embodiments of the disclosure, the compounds of formula (III) as otherwise described herein are those wherein each $R^{3a}$ is independent selected from hydrogen, halogen, $C_1$-$C_4$ alkyl, halogenated $C_1$-$C_4$ alkyl, nitro, cyano, and —COOH; or each $R^{3a}$ is independently selected from hydrogen, $C_1$-$C_4$ alkyl, or halogen; or each $R^{3a}$ is independently selected from hydrogen, methyl, or halogen. In certain embodiments, at least one $R^{3a}$ is independently methyl or halogen (e.g., fluorine) and the remaining $R^{3a}$ are hydrogen. For example, the ring $A^1$ may be

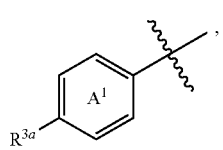

where $R^{3a}$ is methyl or halogen (e.g., fluorine). In certain embodiments, each $R^{4a}$ is independently selected from hydrogen, halogen, $C_1$-$C_4$ alkyl, halogenated $C_1$-$C_4$ alkyl, —S(O$_2$)(halogenated $C_1$-$C_4$ alkyl), nitro, cyano, and —COOH; or each $R^{4a}$ is independently selected from hydrogen, halogen, halogenated $C_1$-$C_4$ alkyl, —S(O$_2$)(halogenated $C_1$-$C_4$ alkyl), nitro, cyano, and —COOH; or each $R^{4a}$ is independently selected from hydrogen, halogen, $C_1$-$C_4$ alkyl, halogenated $C_1$-$C_4$ alkyl, nitro, and cyano. In certain embodiments, at least one $R^{4a}$ is independently halogen, $C_1$-$C_4$ alkyl, halogenated $C_1$-$C_4$ alkyl, nitro, and cyano; or at least one $R^{4a}$ is independently halogen, $C_1$-$C_4$ alkyl, halogenated $C_1$-$C_4$ alkyl, nitro, and cyano, and the remaining $R^{4a}$ are hydrogen. For example, the ring $A^2$ may be

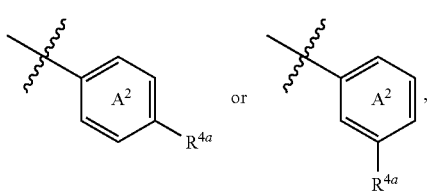

where $R^{4a}$ is independently halogen, $C_1$-$C_4$ alkyl, halogenated $C_1$-$C_4$ alkyl, nitro, and cyano.

Another embodiment of the disclosure provides compounds of formula (I)-(II) and (IV)-(V) as otherwise described herein wherein -$L^1$-$L^2$-$L^3$- is —O—.

Another embodiment of the disclosure provides compounds of formula (I)-(II) and (IV)-(V) as otherwise described herein wherein -$L^1$-$L^2$-$L^3$- is a bond.

Another embodiment of the disclosure provides compounds of formula (I)-(II) and (IV)-(V) as otherwise described herein wherein -$L^1$-$L^2$-$L^3$- is —CR$^2$=N—NHCO—. In some embodiments, $R^2$ is hydrogen.

Another embodiment of the disclosure provides compounds of formula (I)-(II) and (IV)-(V) as otherwise described herein wherein -$L^1$-$L^2$-$L^3$- is —NH—C(O)—NH—, —NCH$_3$—C(O)—NH—, —NHC(=NH)NH—, —NHC(=NCN)NH—, or

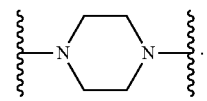 [SMILES: *N1CCN(*)CC1]

In some embodiments, the compound is selected from

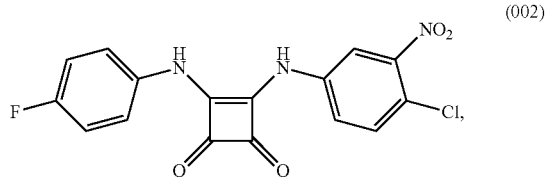
(002)

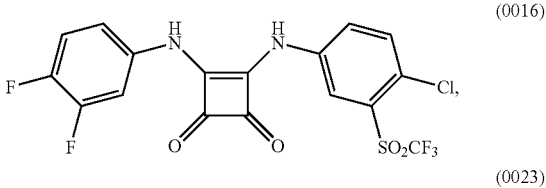
(0016)

(0023)

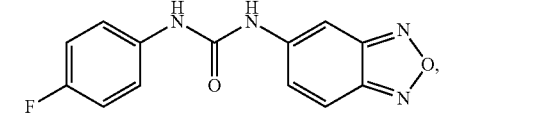
(0027)

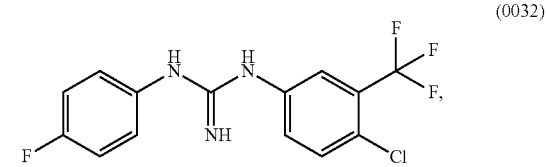
(0032)

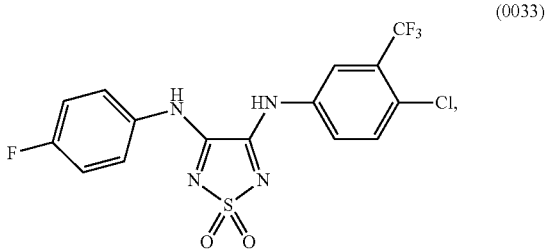
(0033)

-continued
(0034)
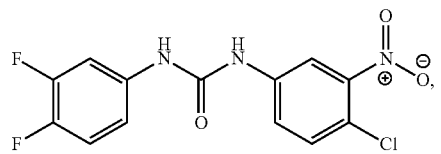
(0041)
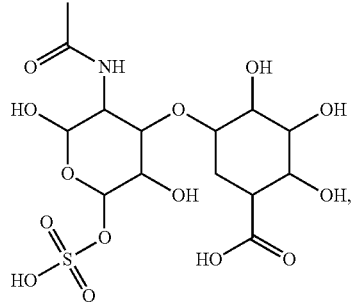
(0042)
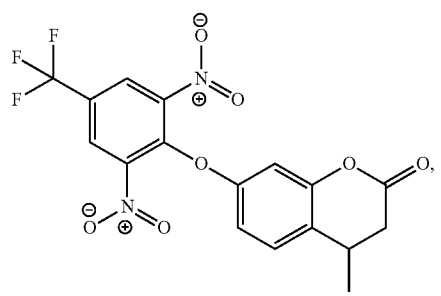
(0043)
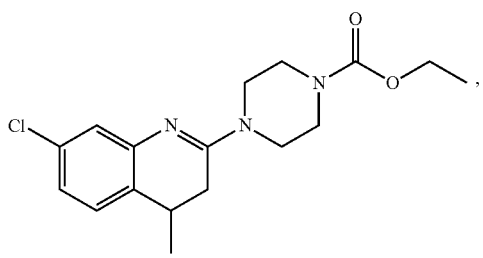
(0047)
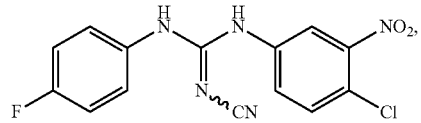
(0054)
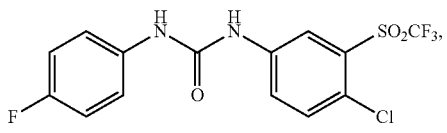
(0064)
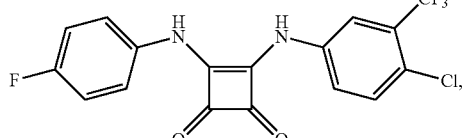
(0069)
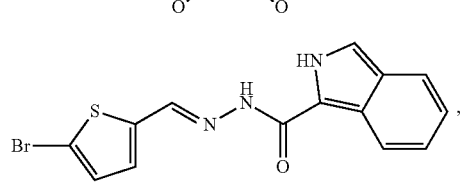
-continued
(0075)
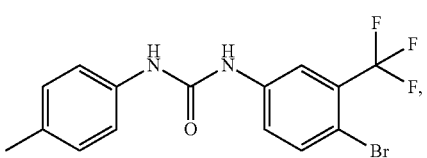
(0079)
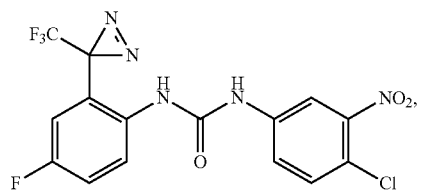
(0080)
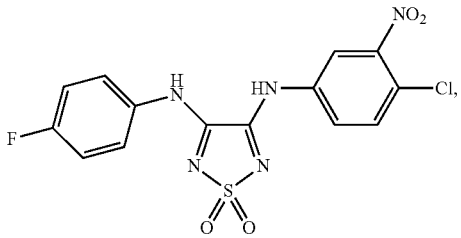
(0083)
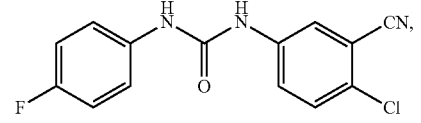
(0090)
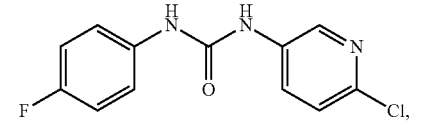
(0092)
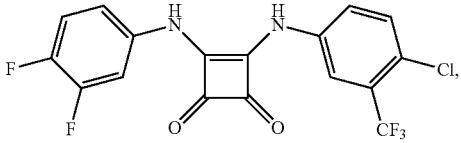
(0094)
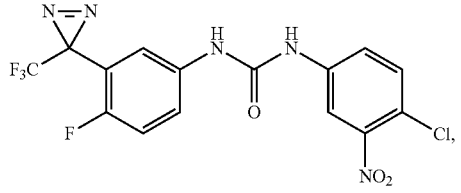

21
-continued
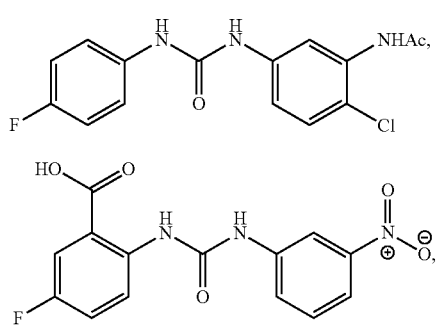
(0095)
22
-continued
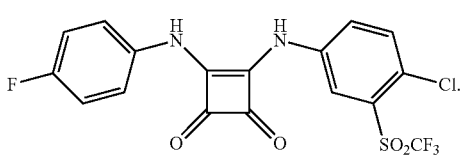
(112)
(106)
Some embodiments relate to a compound selected from Table 1:
TABLE 1
| No. | Structure | ΔTm |
|---|---|---|
| 0001 | 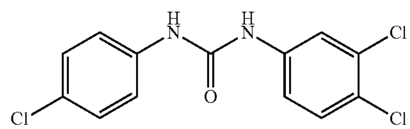 [SMILES: O=C(Nc1ccc(Cl)cc1)Nc1ccc(Cl)c(Cl)c1] | 4.78 |
| 0002 | 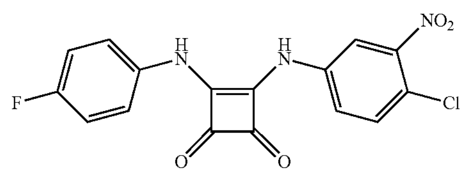 | 1.9 |
| 0003 | 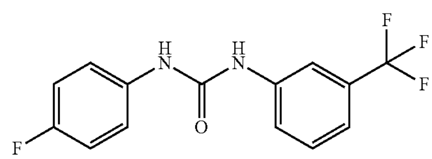 [SMILES: O=C(Nc1ccc(F)cc1)Nc1cccc(C(F)(F)F)c1] | 1.78 |
| 0004 | 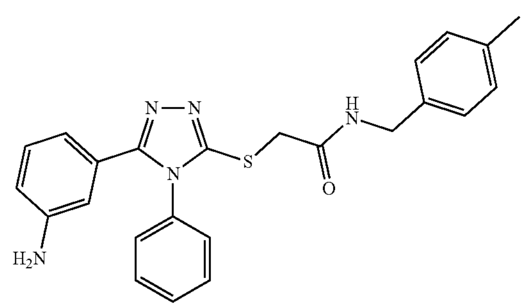 [SMILES: Cc1ccc(CNC(=O)CSc2nnc(-c3cccc(N)c3)n2-c2ccccc2)cc1] | −9.46 |
| 0005 | 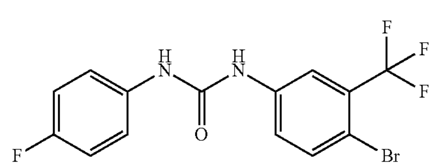 [SMILES: O=C(Nc1ccc(F)cc1)Nc1ccc(Br)c(C(F)(F)F)c1] | 5.1 |
| 0006 | 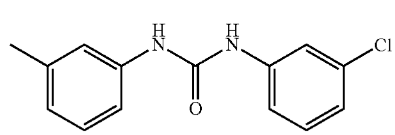 [SMILES: Cc1cccc(NC(=O)Nc2cccc(Cl)c2)c1] | 2.5 |

TABLE 1-continued

| No. | Structure | ΔTm |
|---|---|---|
| 0007 | 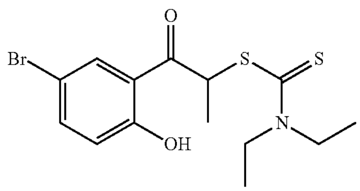 [SMILES: CCN(CC)C(=S)SC(C)C(=O)c1cc(Br)ccc1O] | −10.57 |
| 0008 | 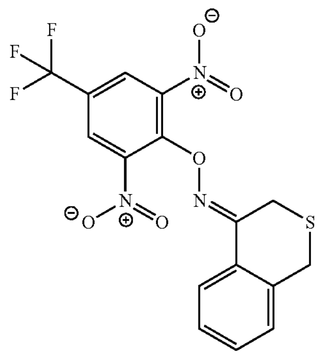 [SMILES: O=[N+]([O-])c1cc(C(F)(F)F)cc([N+](=O)[O-])c1O/N=C1\CSCc2ccccc21] | −4.56 |
| 0009 | 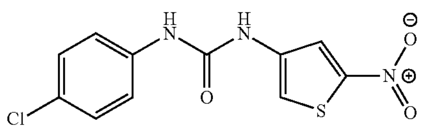 [SMILES: O=C(Nc1ccc(Cl)cc1)Nc1csc([N+](=O)[O-])c1] | 4.1 |
| 0010 | 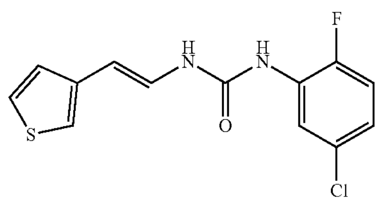 [SMILES: O=C(N/C=C/c1ccsc1)Nc1cc(Cl)ccc1F] | 5.43 |
| 0011 | 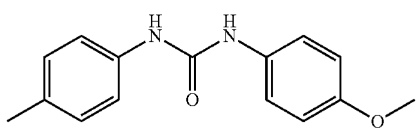 | 2.61 |
| 0012 | 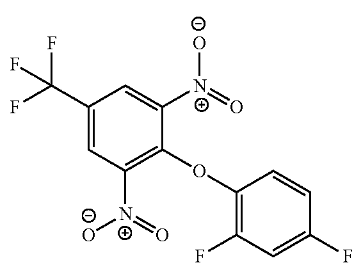 [SMILES: O=[N+]([O-])c1cc(C(F)(F)F)cc([N+](=O)[O-])c1Oc1ccc(F)cc1F] | −4.73 |
| 0013 | 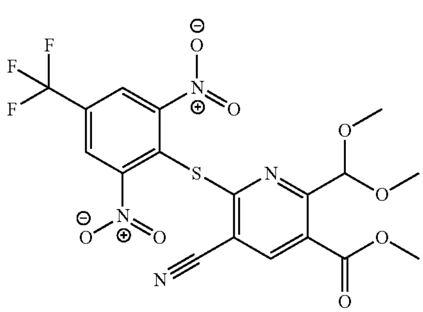 [SMILES: COC(=O)c1cc(C#N)c(Sc2c([N+](=O)[O-])cc(C(F)(F)F)cc2[N+](=O)[O-])nc1C(OC)OC] | −7.4 |

TABLE 1-continued

| No. | Structure | ΔTm |
|---|---|---|
| 0014 | 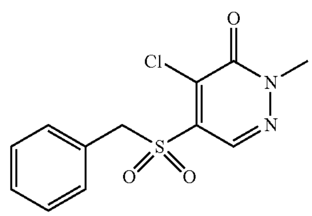 [SMILES: Cn1ncc(S(=O)(=O)Cc2ccccc2)c(Cl)c1=O] | −4.56 |
| 0015 | 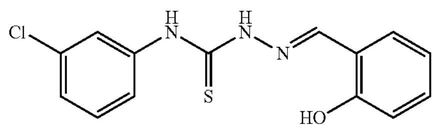 [SMILES: Oc1ccccc1/C=N/NC(=S)Nc1cccc(Cl)c1] | 3.44 |
| 0016 | 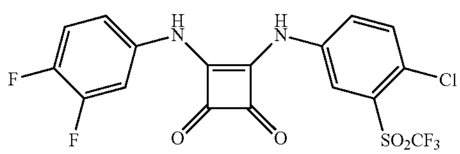 | 2.75 |
| 0017 | 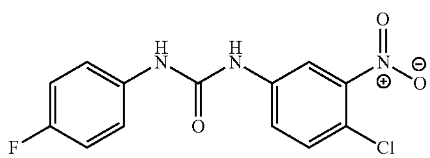 [SMILES: O=C(Nc1ccc(F)cc1)Nc1ccc(Cl)c([N+](=O)[O-])c1] | 3 |
| 0018 | 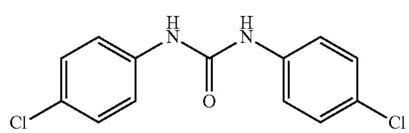 [SMILES: O=C(Nc1ccc(Cl)cc1)Nc1ccc(Cl)cc1] | 2.44 |
| 0019 | 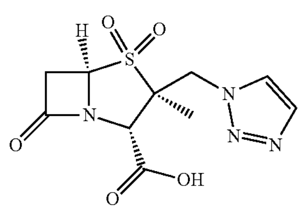 [SMILES: C[C@]1(Cn2ccnn2)[C@H](C(=O)O)N2C(=O)C[C@H]2S1(=O)=O] | −4.27 |

TABLE 1-continued
| No. | Structure | ΔTm |
|---|---|---|
| 0020 | 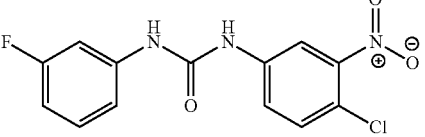 | 5.2 |
| 0021 | 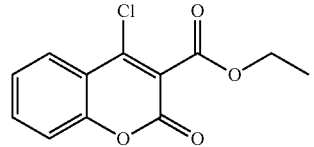 [SMILES: CCOC(=O)c1c(Cl)c2ccccc2oc1=O] | −9.19 |
| 0022 | 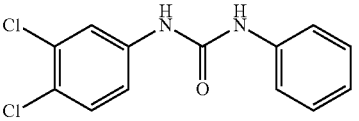 [SMILES: O=C(Nc1ccccc1)Nc1ccc(Cl)c(Cl)c1] | 2.78 |
| 0023 | 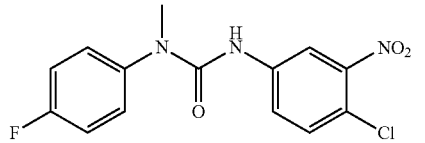 [SMILES: CN(C(=O)Nc1ccc(Cl)c([N+](=O)[O-])c1)c1ccc(F)cc1] | 0.67 |
| 0024 | 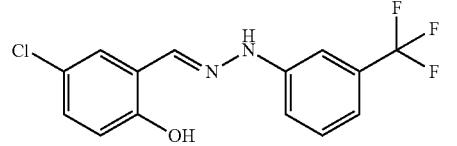 [SMILES: Oc1ccc(Cl)cc1/C=N/Nc1cccc(C(F)(F)F)c1] | 4.44 |
| 0025 | 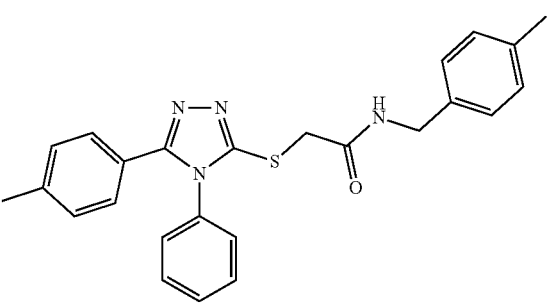 | −9.21 |
| 0026 | 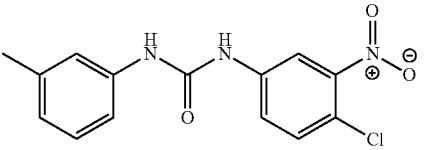 [SMILES: Cc1cccc(NC(=O)Nc2ccc(Cl)c([N+](=O)[O-])c2)c1] | 5.75 |
| 0027 | 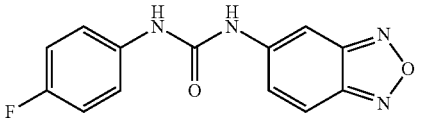 | 2.8 |
| 0028 | 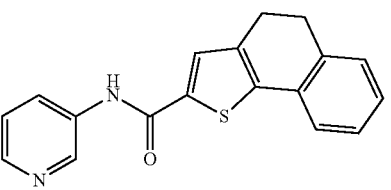 [SMILES: O=C(Nc1cccnc1)c1cc2c(s1)-c1ccccc1CC2] | −9.69 |

TABLE 1-continued

| No. | Structure | ΔTm |
|---|---|---|
| 0029 | 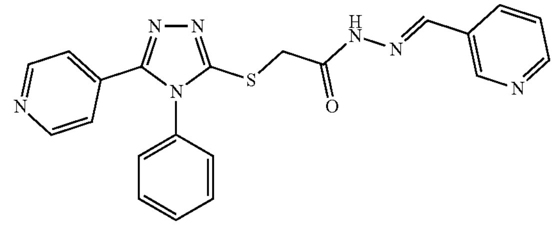 [SMILES: O=C(CSc1nnc(-c2ccncc2)n1-c1ccccc1)N/N=C/c1cccnc1] | −8.96 |
| 0030 | 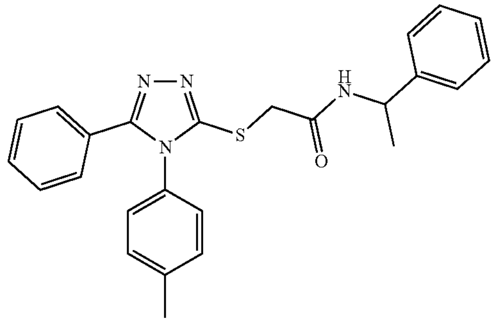 [SMILES: Cc1ccc(-n2c(SCC(=O)NC(C)c3ccccc3)nnc2-c2ccccc2)cc1] | −8.57 |
| 0031 | 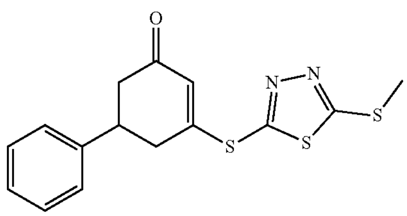 [SMILES: CSc1nnc(SC2=CC(=O)CC(c3ccccc3)C2)s1] | −6.23 |
| 0032 | 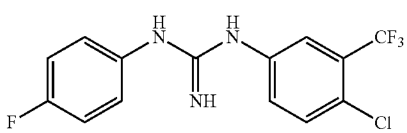 [SMILES: N=C(Nc1ccc(F)cc1)Nc1ccc(Cl)c(C(F)(F)F)c1] | 0.75 |
| 0033 | 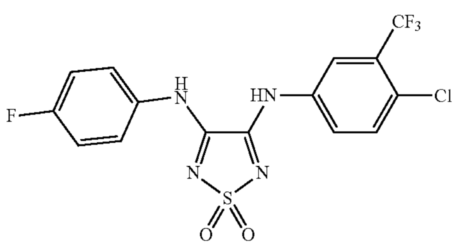 [SMILES: O=S1(=O)N=C(Nc2ccc(F)cc2)C(Nc2ccc(Cl)c(C(F)(F)F)c2)=N1] | 1.9 |
| 0034 | 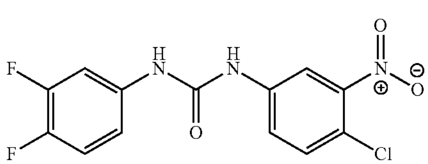 [SMILES: O=C(Nc1ccc(F)c(F)c1)Nc1ccc(Cl)c([N+](=O)[O-])c1] | 5.7 |
| 0035 | 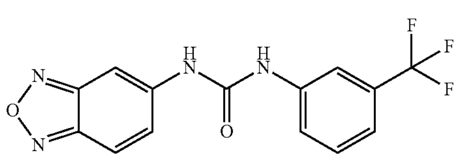 [SMILES: O=C(Nc1cccc(C(F)(F)F)c1)Nc1ccc2nonc2c1] | 6.44 |
| 0036 | 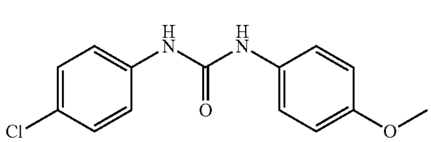 [SMILES: COc1ccc(NC(=O)Nc2ccc(Cl)cc2)cc1] | 2.61 |

TABLE 1-continued

| No. | Structure | ΔTm |
|-----|-----------|-----|
| 0037 | 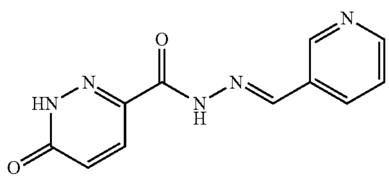 [SMILES: O=C(N/N=C/c1cccnc1)c1ccc(=O)[nH]n1] | −9.74 |
| 0038 | 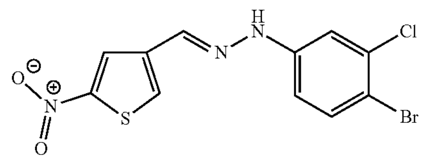 [SMILES: O=[N+]([O-])c1cc(/C=N/Nc2ccc(Br)c(Cl)c2)cs1] | 7.27 |
| 0039 | 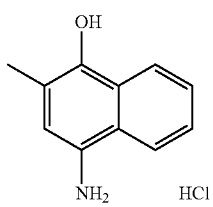 | −4.28 |
| 0040 | 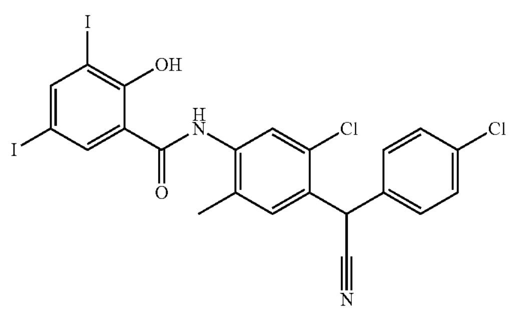 [SMILES: Cc1cc(C(C#N)c2ccc(Cl)cc2)c(Cl)cc1NC(=O)c1cc(I)cc(I)c1O] | −7.95 |
| 0041 | 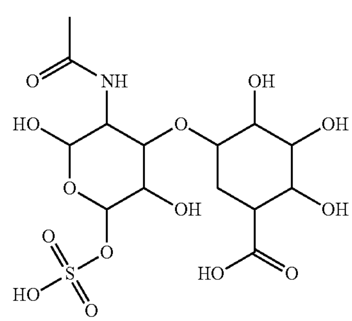 [SMILES: CC(=O)NC1C(O)OC(OS(=O)(=O)O)C(O)C1OC1CC(C(=O)O)C(O)C(O)C1O] | −3.11 |
| 0042 | 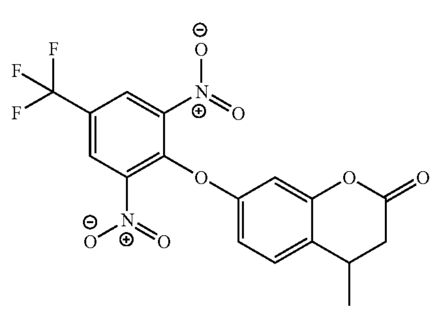 [SMILES: CC1CC(=O)Oc2cc(Oc3c([N+](=O)[O-])cc(C(F)(F)F)cc3[N+](=O)[O-])ccc21] | −6.23 |

TABLE 1-continued

| No. | Structure | ΔTm |
|---|---|---|
| 0043 | 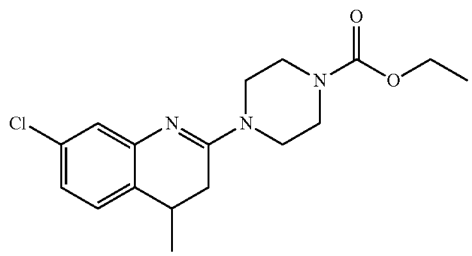 [SMILES: CCOC(=O)N1CCN(C2=Nc3cc(Cl)ccc3C(C)C2)CC1] | −9.07 |
| 0044 | 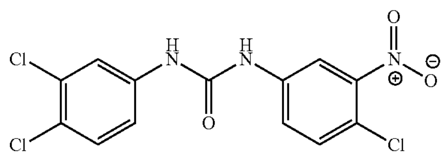 [SMILES: O=C(Nc1ccc(Cl)c(Cl)c1)Nc1ccc(Cl)c([N+](=O)[O-])c1] | 2.33 |
| 0045 | 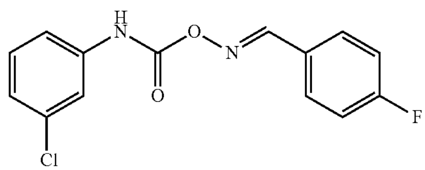 [SMILES: O=C(Nc1cccc(Cl)c1)O/N=C/c1ccc(F)cc1] | −8.21 |
| 0046 | 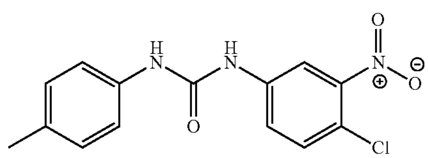 [SMILES: Cc1ccc(NC(=O)Nc2ccc(Cl)c([N+](=O)[O-])c2)cc1] | 4.3 |
| 0047 | 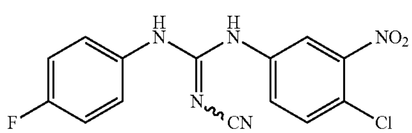 [SMILES: N#CN=C(Nc1ccc(F)cc1)Nc1ccc(Cl)c([N+](=O)[O-])c1] | 0.75 |
| 0048 | 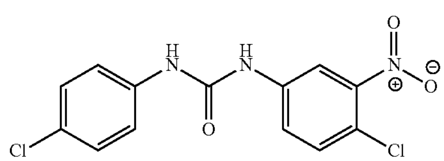 [SMILES: O=C(Nc1ccc(Cl)cc1)Nc1ccc(Cl)c([N+](=O)[O-])c1] | 2.61 |
| 0049 | 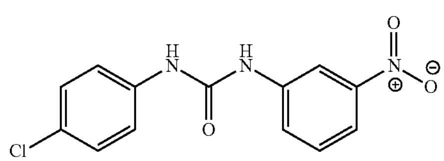 [SMILES: O=C(Nc1ccc(Cl)cc1)Nc1cccc([N+](=O)[O-])c1] | 3.11 |
| 0050 | 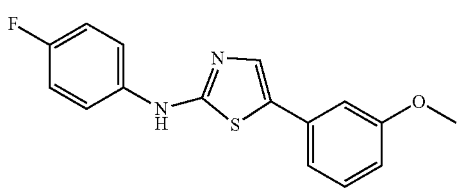 [SMILES: COc1cccc(-c2cnc(Nc3ccc(F)cc3)s2)c1] | 2.93 |
| 0051 | 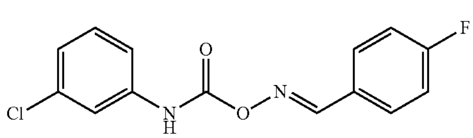 [SMILES: O=C(Nc1cccc(Cl)c1)O/N=C/c1ccc(F)cc1] | −6.91 |

TABLE 1-continued

| No. | Structure | ΔTm |
|---|---|---|
| 0052 | 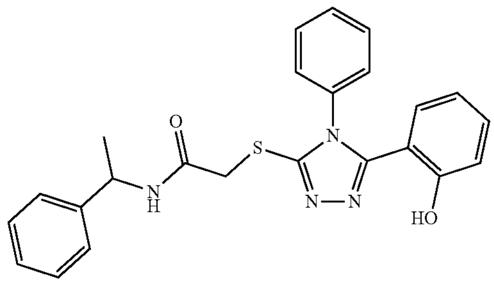 [SMILES: CC(NC(=O)CSc1nnc(-c2ccccc2O)n1-c1ccccc1)c1ccccc1] | −10.96 |
| 0053 | 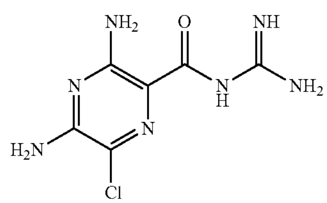 [SMILES: N=C(N)NC(=O)c1nc(Cl)c(N)nc1N] | −10.07 |
| 0054 | 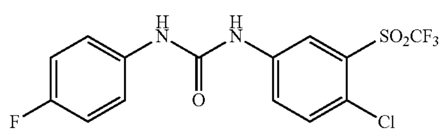 | 2.9 |
| 0055 | 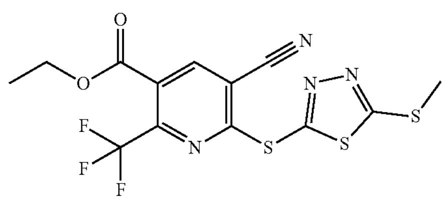 [SMILES: CCOC(=O)c1cc(C#N)c(Sc2nnc(SC)s2)nc1C(F)(F)F] | −9.69 |
| 0056 | 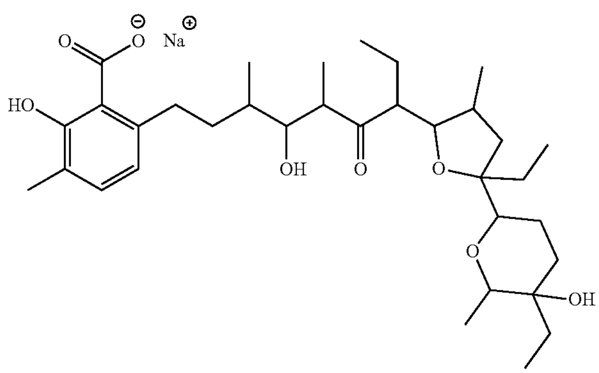 [SMILES: CCC(C(=O)C(C)C(O)C(C)CCc1ccc(C)c(O)c1C(=O)[O-])C1OC(CC)(C2CCC(O)(CC)C(C)O2)CC1C ; [Na+]] | −5.96 |
| 0057 | 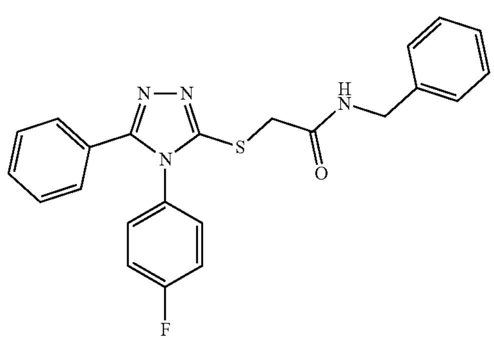 [SMILES: O=C(CSc1nnc(-c2ccccc2)n1-c1ccc(F)cc1)NCc1ccccc1] | −10.46 |

TABLE 1-continued

| No. | Structure | ΔTm |
|---|---|---|
| 0058 | 1-(4-methylphenyl)-3-[3-(trifluoromethyl)phenyl]urea | 2.58 |
| 0059 | 3-[4-(4-hydroxy-3-iodophenoxy)-3,5-diiodophenyl]propanoic acid | −3.45 |
| 0060 | 1-(3-chlorophenyl)-3-(4-fluorophenyl)urea | 2.5 |
| 0061 | 1-(3-chlorophenyl)-3-(4-chloro-3-nitrophenyl)urea | 2.94 |
| 0062 | 2-[4-[2,6-dinitro-4-(trifluoromethyl)phenoxy]phenyl]-1,3-dithiolane | −6.9 |
| 0063 | 1-(3-chlorophenyl)-3-(3-methylphenyl)urea | 2.5 |
| 0064 | 3-(4-fluoroanilino)-4-[4-chloro-3-(trifluoromethyl)anilino]cyclobut-3-ene-1,2-dione | 2.3 |
| 0065 | 1-[4-cyano-5-(methylsulfanyl)thiophen-2-yl]-3-[3-(trifluoromethyl)phenyl]urea | 4.44 |

TABLE 1-continued

| No. | Structure | ΔTm |
|---|---|---|
| 0066 | *1,3-bis(chlorophenyl)urea (4-Cl and 3-Cl)* | 3 |
| 0067 | *1-(3-methylphenyl)-3-(3-nitrophenyl)urea* | 4 |
| 0068 | *1-(4-methylphenyl)-3-(3-chlorophenyl)urea* | 2.75 |
| 0069 | *(E)-N'-((5-bromothiophen-2-yl)methylene)-1H-isoindole-2-carbohydrazide* | 8.06 |
| 0070 | *2,4-dichloro-6-(((3-(trifluoromethyl)phenyl)imino)methyl)phenyl 3,4,5-trimethoxybenzoate* | −7.24 |
| 0071 | *(Z)-1-(4-methylphenyl)-3-phenyl-3-(piperidin-1-yl)prop-2-en-1-one* | −6.24 |
| 0072 | *ethyl 3-(4-(4-(trifluoromethyl)-2,6-dinitrophenoxy)phenyl)propanoate* | 3.39 |
| 0073 | *2-(2,4-dichlorobenzyl)-4-(2,4,4-trimethylpentan-2-yl)phenol* | 2.6 |

TABLE 1-continued
| No. | Structure | ΔTm |
|---|---|---|
| 0074 | 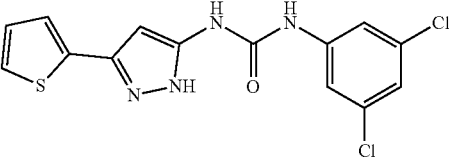 [SMILES: O=C(Nc1cc(Cl)cc(Cl)c1)Nc1cc(-c2cccs2)n[nH]1] | 2.61 |
| 0075 | 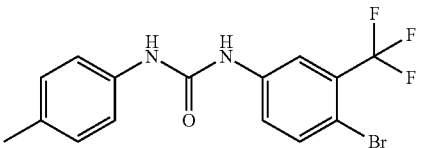 [SMILES: Cc1ccc(NC(=O)Nc2ccc(Br)c(C(F)(F)F)c2)cc1] | 2.61 |
| 0076 | 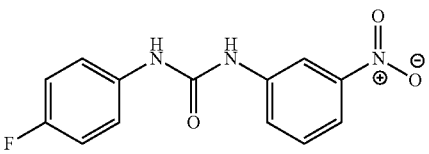 [SMILES: O=C(Nc1ccc(F)cc1)Nc1cccc([N+](=O)[O-])c1] | −7.23 |
| 0077 | 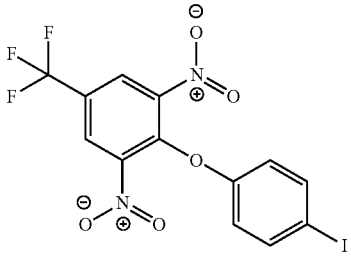 [SMILES: O=[N+]([O-])c1cc(C(F)(F)F)cc([N+](=O)[O-])c1Oc1ccc(I)cc1] | 2.5 |
| 0078 | 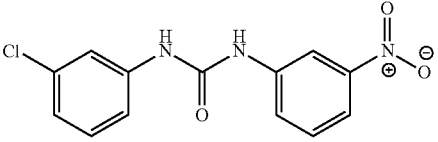 [SMILES: O=C(Nc1cccc(Cl)c1)Nc1cccc([N+](=O)[O-])c1] | 2.25 |
| 0079 | 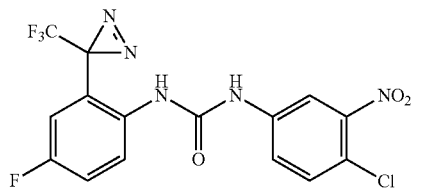 [SMILES: O=C(Nc1ccc(Cl)c([N+](=O)[O-])c1)Nc1ccc(F)cc1C1(C(F)(F)F)N=N1] | 2.25 |
| 0080 | 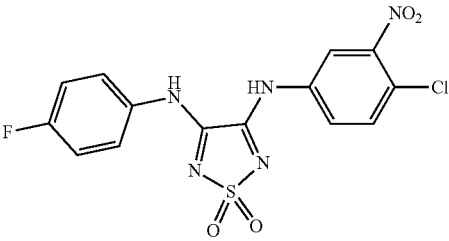 [SMILES: O=[N+]([O-])c1cc(NC2=NS(=O)(=O)N=C2Nc2ccc(F)cc2)ccc1Cl] | 1.6 |
| 0081 | 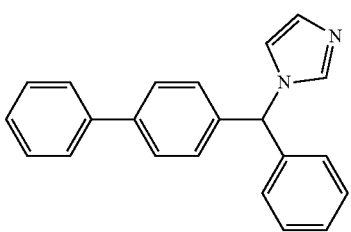 [SMILES: c1ccc(-c2ccc(C(c3ccccc3)n3ccnc3)cc2)cc1] | −3.6 |

TABLE 1-continued
| No. | Structure | ΔTm |
|---|---|---|
| 0082 | 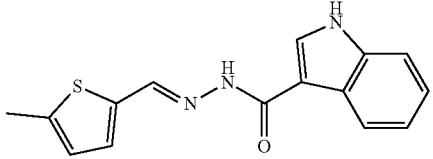 [SMILES: Cc1ccc(/C=N/NC(=O)c2c[nH]c3ccccc23)s1] | 3.9 |
| 0083 | 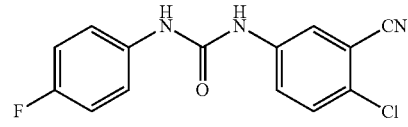 [SMILES: N#Cc1cc(NC(=O)Nc2ccc(F)cc2)ccc1Cl] | 2 |
| 0084 | 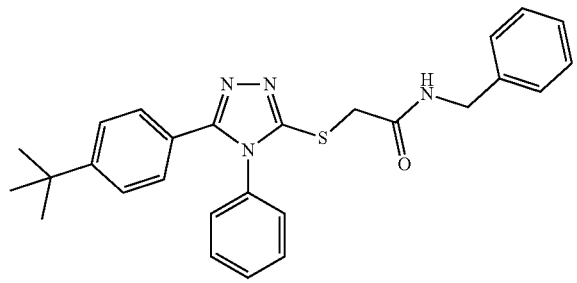 [SMILES: CC(C)(C)c1ccc(-c2nnc(SCC(=O)NCc3ccccc3)n2-c2ccccc2)cc1] | −8.96 |
| 0085 | 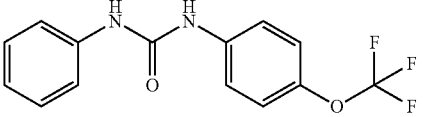 [SMILES: O=C(Nc1ccccc1)Nc1ccc(OC(F)(F)F)cc1] | 3.26 |
| 0086 | 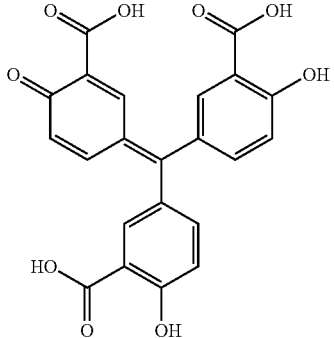 [SMILES: O=C(O)C1=CC(=C(c2ccc(O)c(C(=O)O)c2)c2ccc(O)c(C(=O)O)c2)C=CC1=O] | −11.46 |
| 0087 | 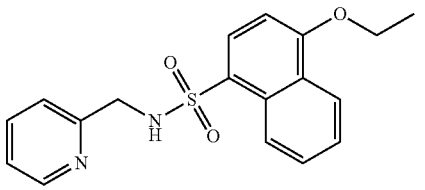 [SMILES: CCOc1ccc(S(=O)(=O)NCc2ccccn2)c2ccccc12] | −9.24 |
| 0088 | 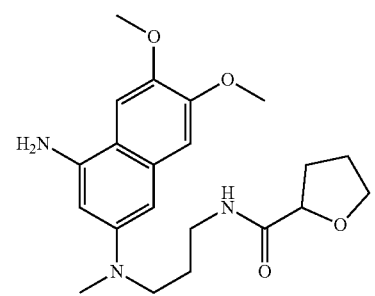 [SMILES: COc1cc2cc(N(C)CCCNC(=O)C3CCCO3)cc(N)c2cc1OC] | −3.02 |

TABLE 1-continued

| No. | Structure | ΔTm |
|---|---|---|
| 0089 | 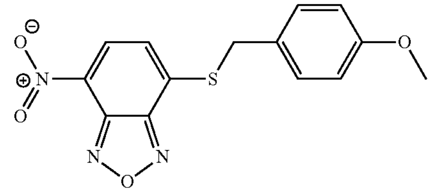 [SMILES: COc1ccc(CSc2ccc([N+](=O)[O-])c3nonc23)cc1] | −5.73 |
| 0090 | 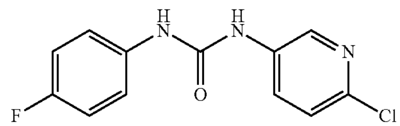 [SMILES: O=C(Nc1ccc(F)cc1)Nc1ccc(Cl)nc1] | 0.67 |
| 0091 | 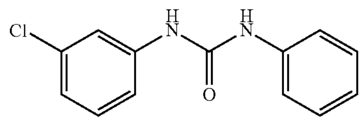 [SMILES: O=C(Nc1ccccc1)Nc1cccc(Cl)c1] | 2.5 |
| 0092 | 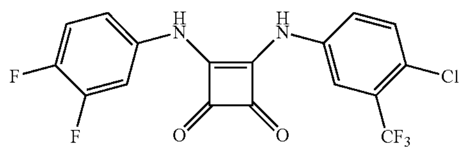 | 2.33 |
| 0093 | 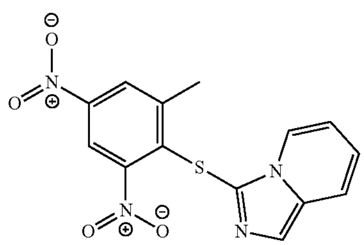 [SMILES: Cc1cc([N+](=O)[O-])cc([N+](=O)[O-])c1Sc1ncc2ccccn12] | −3.44 |
| 0094 | 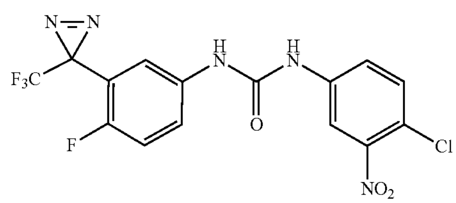 [SMILES: O=C(Nc1ccc(Cl)c([N+](=O)[O-])c1)Nc1ccc(F)c(C2(C(F)(F)F)N=N2)c1] | 2.92 |
| 0095 | 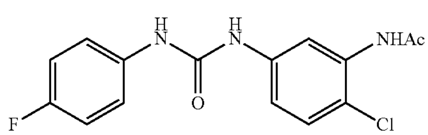 [SMILES: CC(=O)Nc1cc(NC(=O)Nc2ccc(F)cc2)ccc1Cl] | 0.67 |
| 0096 | 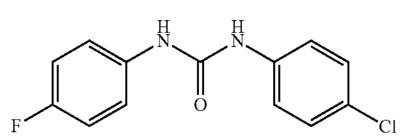 | 2.61 |
| 0097 | 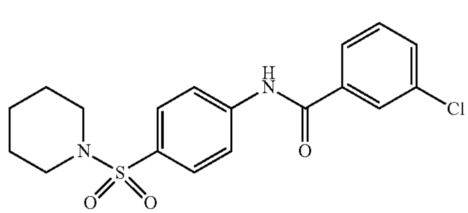 [SMILES: O=C(Nc1ccc(S(=O)(=O)N2CCCCC2)cc1)c1cccc(Cl)c1] | 3.43 |

TABLE 1-continued

| No. | Structure | ΔTm |
|---|---|---|
| 0098 | 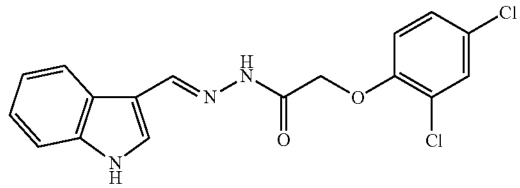 [SMILES: O=C(COc1ccc(Cl)cc1Cl)N/N=C/c1c[nH]c2ccccc12] | 4.93 |
| 0099 | 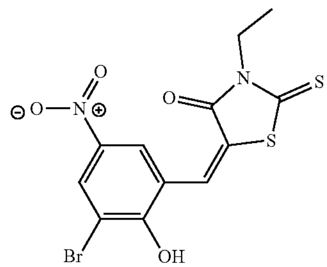 [SMILES: CCN1C(=O)/C(=C\c2cc([N+](=O)[O-])cc(Br)c2O)SC1=S] | −6.74 |
| 0100 | 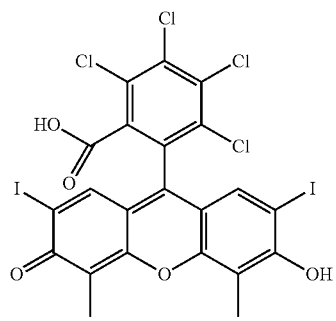 [SMILES: Cc1c2oc3c(C)c(O)c(I)cc3c(-c3c(Cl)c(Cl)c(Cl)c(Cl)c3C(=O)O)c-2cc(I)c1=O] | −7.52 |
| 0101 | 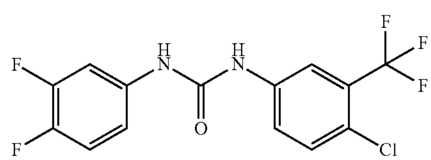 [SMILES: O=C(Nc1ccc(F)c(F)c1)Nc1ccc(Cl)c(C(F)(F)F)c1] | 3.33 |
| 0102 | 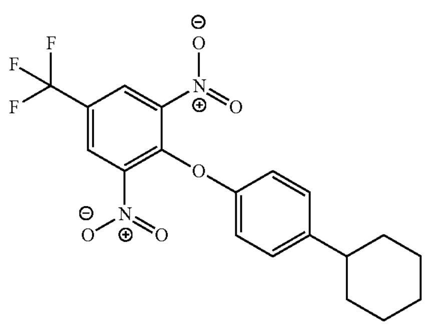 [SMILES: O=[N+]([O-])c1cc(C(F)(F)F)cc([N+](=O)[O-])c1Oc1ccc(C2CCCCC2)cc1] | −6.23 |
| 0103 | 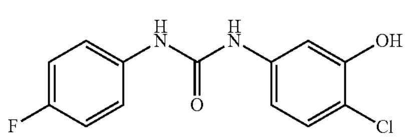 [SMILES: O=C(Nc1ccc(F)cc1)Nc1ccc(Cl)c(O)c1] | 4.7 |
| 0104 | 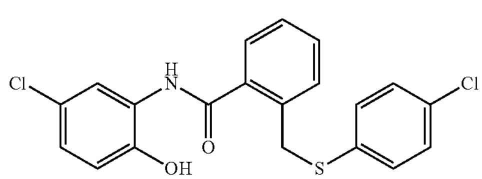 [SMILES: O=C(Nc1cc(Cl)ccc1O)c1ccccc1CSc1ccc(Cl)cc1] | 3.27 |

TABLE 1-continued

| No. | Structure | ΔTm |
|---|---|---|
| 0105 | 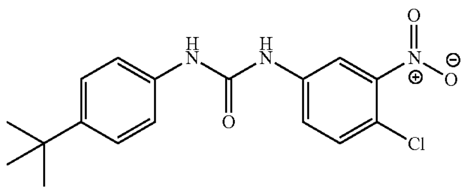 [SMILES: CC(C)(C)c1ccc(NC(=O)Nc2ccc(Cl)c([N+](=O)[O-])c2)cc1] | 3.2 |
| 0106 | 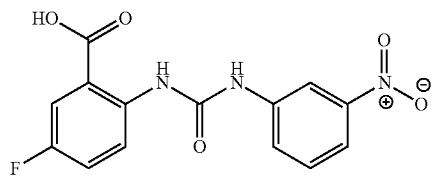 [SMILES: O=C(Nc1cccc([N+](=O)[O-])c1)Nc1ccc(F)cc1C(=O)O] | 3.28 |
| 0107 | 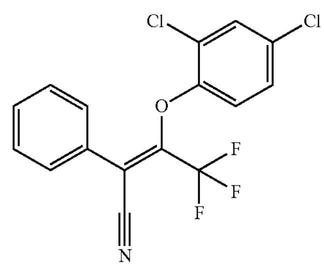 [SMILES: N#C/C(=C(/Oc1ccc(Cl)cc1Cl)C(F)(F)F)c1ccccc1] | −4.4 |
| 0108 | 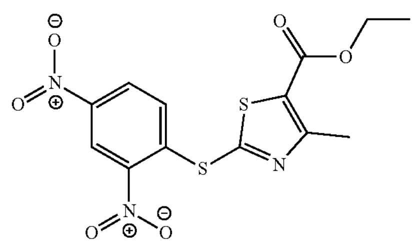 [SMILES: CCOC(=O)c1sc(Sc2ccc([N+](=O)[O-])cc2[N+](=O)[O-])nc1C] | −4.19 |
| 0109 | 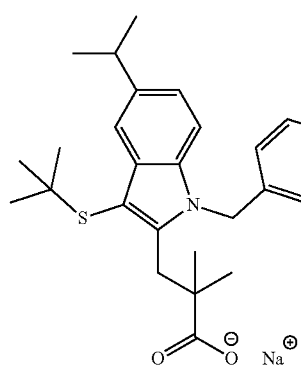 | −9.02 |
| 0110 | 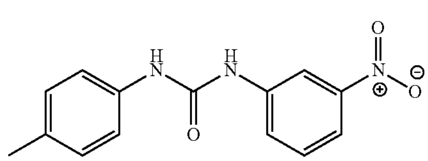 [SMILES: Cc1ccc(NC(=O)Nc2cccc([N+](=O)[O-])c2)cc1] | 2.94 |

TABLE 1-continued

| No. | Structure | ΔTm |
|---|---|---|
| 0111 | 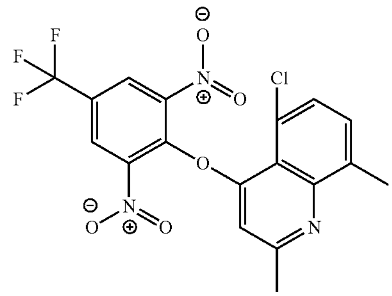 [SMILES: Cc1cc(Oc2c([N+](=O)[O-])cc(C(F)(F)F)cc2[N+](=O)[O-])c2c(Cl)ccc(C)c2n1] | −5.21 |
| 0112 | 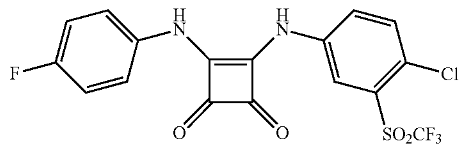 | 2.08 |
| 0113 | 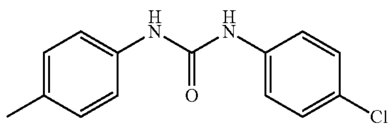 [SMILES: Cc1ccc(NC(=O)Nc2ccc(Cl)cc2)cc1] | 2.28 |
| 0114 | 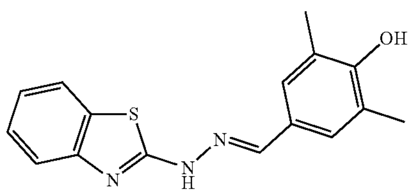 [SMILES: Cc1cc(/C=N/Nc2nc3ccccc3s2)cc(C)c1O] | 0.49 |
| 0115 | 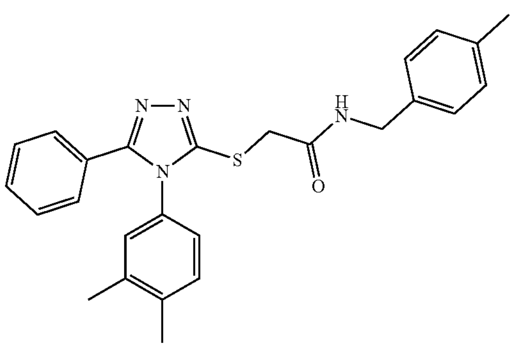 [SMILES: Cc1ccc(CNC(=O)CSc2nnc(-c3ccccc3)n2-c2ccc(C)c(C)c2)cc1] | −9.91 |
| 0116 | 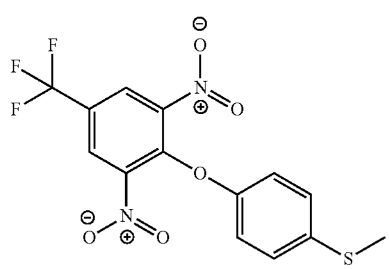 [SMILES: CSc1ccc(Oc2c([N+](=O)[O-])cc(C(F)(F)F)cc2[N+](=O)[O-])cc1] | −5.56 |
| 0117 | 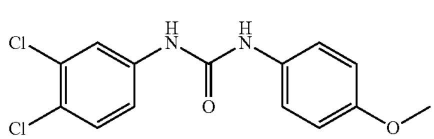 [SMILES: COc1ccc(NC(=O)Nc2ccc(Cl)c(Cl)c2)cc1] | |

In certain embodiments, the compounds of the disclosure as disclosed herein are selected from Table 2:

In one embodiment, the compound of the disclosure as described herein is Compound 0005, having the structure:

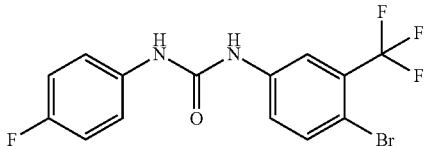 [SMILES: O=C(Nc1ccc(F)cc1)Nc1ccc(Br)c(C(F)(F)F)c1]

and any pharmaceutically acceptable salts, esters, solvates, and mixtures thereof.

In one embodiment, the compound of the disclosure as described herein is Compound 0009, having the structure:

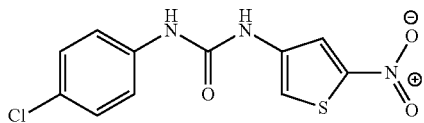 [SMILES: O=C(Nc1ccc(Cl)cc1)Nc1csc([N+](=O)[O-])c1]

and any pharmaceutically acceptable salts, esters, solvates, and mixtures thereof.

In one embodiment, the compound of the disclosure as described herein is Compound 0017, having the structure:

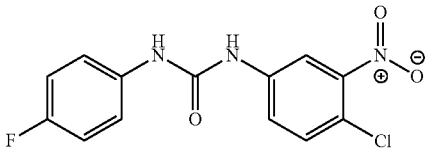 [SMILES: O=C(Nc1ccc(F)cc1)Nc1ccc(Cl)c([N+](=O)[O-])c1]

and any pharmaceutically acceptable salts, esters, solvates, and mixtures thereof.

In one embodiment, the compound of the disclosure as described herein is Compound 0050, having the structure:

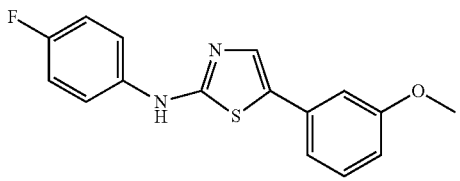 [SMILES: COc1cccc(-c2cnc(Nc3ccc(F)cc3)s2)c1]

and any pharmaceutically acceptable salts, esters, solvates, and mixtures thereof.

In one embodiment, the compound of the disclosure as described herein is Compound 0054, having the structure:

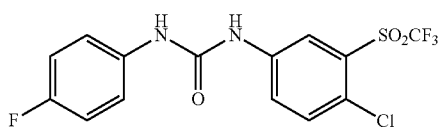

and any pharmaceutically acceptable salts, esters, solvates, and mixtures thereof.

In one embodiment, the compound of the disclosure as described herein is Compound 0064, having the structure:

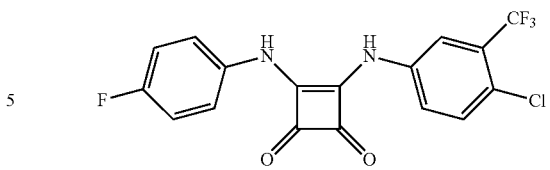

and any pharmaceutically acceptable salts, esters, solvates, and mixtures thereof.

In certain embodiments, the compounds and/or compositions of the disclosure inhibit the activity and/or function of human HSF1. The activity is not limited to a particular type of HSF. In some embodiments, the HSF is HSF1, HSF2, or HSF4. The compounds and/or compositions are not limited by the manner in which they result in HSF inhibition. In some embodiments, HSF inhibition includes, but is not limited to, inhibition of HSF1 homo-trimerization, inhibition of HSF target gene expression (e.g., Heat Shock Elements), inhibition of HSF target protein expression (e.g., Heat Shock Proteins), inhibition of HSF1-mediated genome-wide transcriptional regulation, and/or inhibition of protein chaperone activity (e.g., decreased protein folding, decreased protein solubilization, protein degradation). In certain embodiments, the inhibition of the activity and/or function of HSF1 is by binding of the compound directly to HSF1. For example, in certain embodiments, the binding of the compound stabilizes the HSF1 protein. In certain embodiments, the binding of the compound destabilizes the HSF1 protein.

In some embodiments, the binding of the compound increases the melting temperature of the HSF1 protein by at least 1° C. when compared with the melting temperature of the HSF1 protein prior to binding. In some embodiments, the binding of the compound increases the melting temperature of the HSF1 protein by at least about 0.5, about 1, about 1.5, about 2, about 3, about 3.5, about 4, about 4.5, about 5, or about 5.5° C. when compared with the melting temperature of the HSF1 protein prior to binding. In some embodiments, the binding of the compound increases the melting temperature of the HSF1 protein by no greater than about 0.5, about 1, about 1.5, about 2, about 3, about 3.5, about 4, about 4.5, about 5, or about 5.5° C. when compared with the melting temperature of the HSF1 protein prior to binding. In some embodiments, the binding of the compound increases the melting temperature of the HSF1 protein by about 0.5, about 1, about 1.5, about 2, about 3, about 3.5, about 4, about 4.5, about 5, about 5.5, about 6, about 10, or at any intermediate value spanned by the range herein.

In some embodiments, the binding of the compound decreases the melting temperature of the HSF1 protein by at least 1° C. when compared with the melting temperature of the HSF1 protein prior to binding. In some embodiments, the binding of the compound decreases the melting temperature of the HSF1 protein by at least about 0.5, about 1, about 1.5, about 2, about 3, about 3.5, about 4, about 4.5, about 5, about 5.5, about 6, about 6.5, about 7, about 7.5, about 8, about 9, about 10, about 12.5, or about 15° C. when compared with the melting temperature of the HSF1 protein prior to binding. In some embodiments, the binding of the compound decreases the melting temperature of the HSF1 protein by no greater than about 0.5, about 1, about 1.5, about 2, about 3, about 3.5, about 4, about 4.5, about 5, about 5.5, about 6, about 6.5, about 7, about 7.5, about 8, about 9, about 10, about 12.5, or about 15° C. when compared with the melting temperature of the HSF1 protein prior to binding. In some embodiments, the binding of the compound decreases the melting temperature of the HSF1 protein by about 0.5, about 1, about 1.5, about 2, about 3, about 3.5, about 4, about 4.5, about 5, about 5.5, about 6, about 10, or at any intermediate value spanned by the range herein.

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as 2H, 3H, 13C, 14C, 15N, 18O, 17O, 31P, 32P, 35S, 18F, and 36Cl, respectively. Compounds described herein, and the pharmaceutically acceptable salts, solvates, or stereoisomers thereof which contain the aforementioned isotopes and/or other isotopes of other atoms are within the scope of this disclosure. Certain isotopically-labeled compounds, for example those into which radioactive isotopes such as 3H and 14C are incorporated, are useful in drug and/or substrate tissue distribution assays. Tritiated, i.e., 3H and carbon-14, i.e., 14C, isotopes are particularly preferred for their ease of preparation and detectability. Further, substitution with heavy isotopes such as deuterium, i.e., 2H, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenyl acetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, or sulfate of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N+(C_{1-4}$ alkyl)4, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Administration and Pharmaceutical Composition

In general, the compounds of this invention will be administered in a therapeutically effective amount by any of the accepted modes of administration for agents that serve similar utilities. Therapeutically effective amounts of compound of the disclosure (e.g., any one of compounds of Formula I) may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this invention, i.e., the active ingredient, will depend upon numerous factors such as the severity of the disease to be treated, the age and relative health of the subject, the potency of the compound being utilized, the route and form of administration, and other factors.

In general, compounds of this invention will be administered as pharmaceutical compositions by any one of the following routes: oral, systemic (e.g., intranasal, suppository, intrapulmonary), or parenteral (e.g., intramuscular, intravenous, intrathecal, or intraperitoneal) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, liposomes, exosomes, nanoparticles, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of the disclosure (e.g., of Formula I) in combination with at least one pharmaceutically acceptable excipient. Acceptable excipients are non-toxic, aid administration, and do not adversely affect the therapeutic benefit of the compound of the disclosure. Such excipient may be any solid, liquid, semi-solid or, in the case of an aerosol composition, gaseous excipient that is generally available to one of skill in the art. A "pharmaceutically acceptable excipient and/or carrier" or "diagnostically acceptable excipient and/or carrier" includes but is not limited to, sterile distilled water, saline, phosphate buffered solutions, amino acid-based buffers, or bicarbonate buffered solutions. An excipient selected and the amount of excipient used will depend upon the mode of administration.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of the disclosure (e.g., of Formula I) based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is preferred. The combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In the case wherein the patient's status does improve, upon the doctor's discretion the administration of a compound described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In some embodiments of the present disclosure, the compounds/compositions are administered alone, while in some other embodiments, the compounds/compositions are preferably present in a pharmaceutical formulation/composition comprising at least one active ingredient/agent, as defined above, together with a solid support or alternatively, together with one or more pharmaceutically acceptable carriers and/or excipients. Optionally, such pharmaceutical compositions/formulations may also comprise other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present disclosure suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water*-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the. active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present disclosure are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents.

In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of the present disclosure are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous.solvent for the agent.

Formulations for rectal administration may be presented as a suppository with suitable base comprising, for example, cocoa butter or a salicylate. Likewise, those for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i,e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent. It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoleic acid), extenders, and stabilizers, etc.

In some embodiments, the compounds of the present disclosure are provided in unsolvated form or are in non-aqueous solutions (e.g., ethanol). The compounds may be generated to allow such formulations through the production of specific crystalline polymorphs compatible with the formulations.

In other embodiments, the present disclosure provides instructions for administering said compound to a subject. In certain embodiments, the present disclosure provides instructions for using the compositions contained in a kit for the treatment of cancer (e.g., a cancer characterized by the activation or and/or overexpression of HSF) providing dosing, route of administration, decision trees for treating physicians for correlating patient-specific characteristics with therapeutic courses of action).

Yet another aspect of the present disclosure provides all that is disclosed and illustrated herein.

Combination Therapy

In some cases, a compound described herein is administered in combination with a second anti-cancer agent. Examples of anti-cancer agents for use in combination with a compound of the disclosure (e.g., of Formula I) include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of the disclosure (e.g., of Formula I) include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of the disclosure (e.g., of Formula I) include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+ estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MTF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenyl acetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; Rn retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of the disclosure (e.g., of Formula I) include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of the disclosure (e.g., of Formula I) include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of the disclosure (e.g., of Formula I) include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of the disclosure (e.g., of Formula I) include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible EGFR tyrosine kinase inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

In some cases, a compound described herein (e.g., a compound of Formula I) is administered in combination with TNF-alpha and/or TNF-related apoptosis-inducing ligand (TRAIL). TRAIL shows homology to other members of the TNF-alpha family of proteins. In some cases, a compound described herein (e.g., a compound of Formula I) is administered in combination with a TNF-alpha modulator and/or a TNF-alpha analogue (e.g., lenalidomide, revlimid, CC-5013; CC-4047, ACTIMID, thalidomide and the like).

In some cases, a compound described herein (e.g., a compound of Formula I) is administered in combination with an adjuvant, hormone therapy, immunotherapy or any combination thereof.

Definitions

Unless otherwise defined, all technical terms used herein have the same meaning as commonly understood by one of ordinary skill in the art to which this disclosure belongs, Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of and "consisting of" those certain elements, As used herein, "and/or" refers to and encompasses any and all possible combinations of one or more of the associated listed items, as well as the lack of combinations where interpreted in the alternative ("or").

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Terms used herein may be preceded and/or followed by a single dash, or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" with reference to the chemical structure referred to unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene).

All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as —B-(A)$_a$, wherein a is 0 or 1. In such instances, when a is 0 the moiety is —B and when a is 1 the moiety is —B-A.

"Alkyl" refers to an optionally substituted straight-chain, or optionally substituted branched-chain saturated hydrocarbon monoradical having from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to, ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to, ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —CF$_3$, —OH, —OMe, —NH$_2$, or —NO$_2$. In some embodiments, an alkynyl is optionally substituted with oxo, halogen, —CN, —CF$_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —CF$_3$, —OH, —OMe, —NH$_2$, or —NO$_2$. In some embodiments, an alkylene is optionally substituted with oxo, halogen, —CN, —CF$_3$, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —CF$_3$, —OH, —OMe, —NH$_2$, or —NO$_2$. In some embodiments, an alkoxy is optionally substituted with oxo, halogen, —CN, —CF$_3$, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Hydroxyalkyl include, for example, aminomethyl, aminoethyl, aminopropyl, aminobutyl, or aminopentyl. In some embodiments, the hydroxyalkyl is aminomethyl.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —CF$_3$, —OH, —OMe, —NH$_2$, or —NO$_2$. In some embodiments, an aryl is optionally substituted with halogen, methyl, ethyl, —CN, —CF$_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclobutenyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Deuteroalkyl" refers to an alkyl radical, as defined above, that is substituted by one or more deuterium atoms. In some embodiments, the alkyl is substituted with one deuterium atom. In some embodiments, the alkyl is substituted with one, two, or three deuterium atoms. In some embodiments, the alkyl is substituted with one, two, three, four, five, or six deuterium atomss. Deuteroalkyl includes, for example, CD$_3$, CH$_2$D, CHD$_2$, CH$_2$CD$_3$, CD$_2$CD$_3$, CHDCD$_3$, CH$_2$CH$_2$D, or CH$_2$CHD$_2$. In some embodiments, the deuteroalkyl is CD$_3$.

"Haloalkyl" refers to an alkyl radical, as defined above, that is substituted by one or more halogen atoms. In some embodiments, the alkyl is substituted with one, two or three halogen atoms. In some embodiments, the alkyl is substituted with one, two, three, four, five, or six halogen halogens. Haloalkyl includes, for example, trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl is trifluoromethyl.

"Halo" or "halogen" refers to bromo, chloro, fluoro or iodo. In some embodiments, halogen is fluoro or chloro. In some embodiments, halogen is fluoro.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, or —CH(CH$_3$)OCH$_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl comprises 1 or 2 heteroatoms selected from nitrogen and oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). In some embodiments, the heterocycloalkyl is a 3- to 6-membered heterocycloalkyl. In some embodiments, the cycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to, the monosaccharides, the disaccharides and the oligosaccharides. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl. Unless stated otherwise specifically in the specification, a heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

An "effective amount" or "therapeutically effective amount" refers to an amount of a compound administered to a subject (e.g. a mammal, such as a human), either as a single dose or as part of a series of doses, which is effective to produce a desired therapeutic effect.

"Treatment" of a subject (e.g. a mammal, such as a human) includes any type of intervention used in an attempt to alter the natural course of the subject. In some embodiments, treatment includes administration of a pharmaceutical composition, subsequent to the initiation of a pathologic event or contact with an etiologic agent and includes stabilization of the condition (e.g., condition does not worsen, e.g., cancer does not metastasize and the like) or alleviation of the condition (e.g., reduction in tumor size, remission of cancer, absence of symptoms of autoimmune disease and the like). In other embodiments, treatment also includes prophylactic treatment (e.g., administration of a composition described herein when an individual is suspected to be suffering from a condition described herein).

As used herein, "subject", "individual" and "patient" are used interchangeably. None of the terms imply that a medical professional is required for the administration of the compounds disclosed herein.

Synthesis of Compounds

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Ed., Wiley-Interscience, 2001; or Vogel, A Textbook of Practical Organic Chemistry, Including Qualitative Organic Analysis, Fourth Ed., New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formulae (I)-(VI) can be prepared according to general procedures (below), and/or analogous synthetic procedures. One of skill in the art can adapt the reaction sequences of Examples 3-52 and general procedures to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

Scheme 1 is a nonlimiting example of preparing the compounds described herein. For instance, a substituted aniline compound A can react with compound B to provide the intermediate compound C.

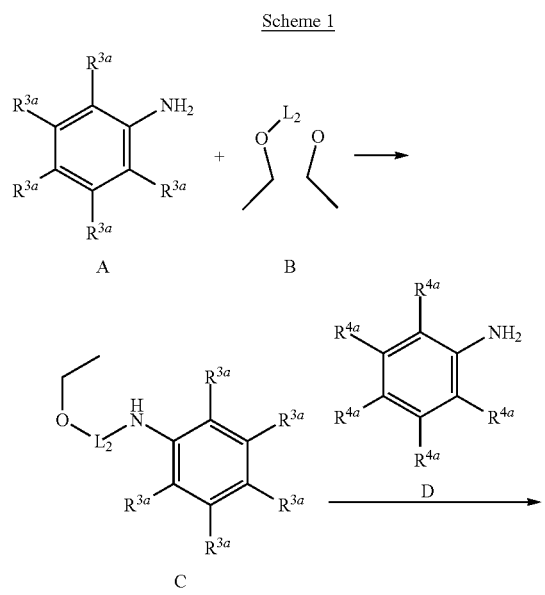

Scheme 1

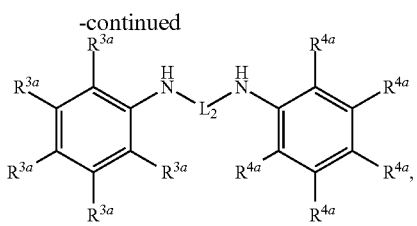

E where $R^{3a}$, $R^{4a}$ and $L^2$ are as defined above.

EXAMPLES

The methods of use and preparation of the compounds of the disclosure is illustrated further by the following examples, which are not to be construed as limiting the disclosure in scope or spirit to the specific procedures and compounds described in them.

Example 1. Identification of Compounds of Interest

Figure 2:
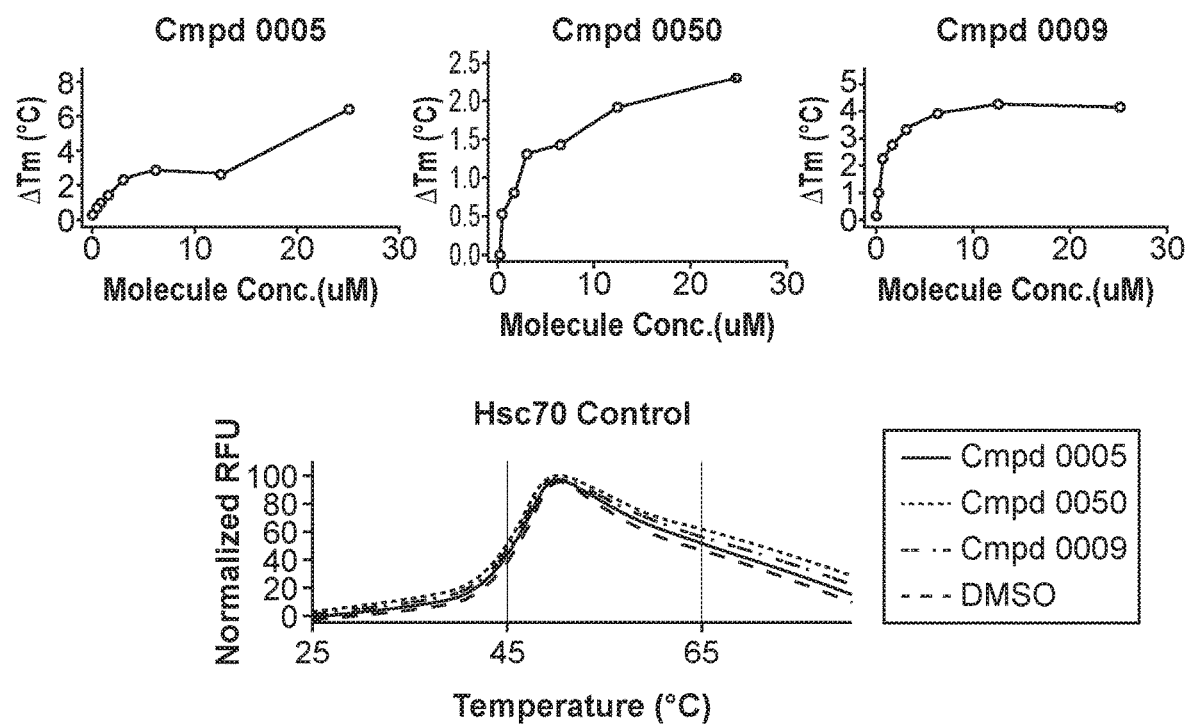
FIG. 2 are graphs showing exemplary thermal denaturation profiles of three compounds of the disclosure, Compounds 0005, 0050 and 0009, and their impact of on the melting of the recombinant protein in accordance with one embodiment of the present disclosure (A) Exemplary thermal denaturation profiles of three compounds of the disclosure from the thermal denaturation profiling screen and their impact on the melting temperature of recombinant HSF1 DNA binding domain. Shown at the top are the changes in recombinant human HSF1 DNA binding domain melting temperature ($\Delta$Tm) (on Y axis) with increasing concentrations in micromolar (X axis) of the molecules Compounds (Cmpds) 0005, 0050 and 0009. (B) Compounds 0005, 0050 and 0009 impact the melting of the recombinant protein Hsc70, whose melting temperature is unaffected by any of the compounds.

Distinct molecules were identified via high throughput thermal denaturation profile screening. Specifically, the screen measured recombinant HSF1 DNA binding domain melting temperature in the presence of the individual molecules in a library of distinct chemicals and in the absence of the chemical (i.e., presence of just a solvent), and two melting temperature values were compared to identify the active compounds. Several HSF1-interacting molecules were identified and validated as bona fide HSF1 interactors in vitro by thermal denaturation profiling where they either increase or decrease the HSF1 DNA binding domain melting temperature. Three examples of molecules that directly interact with HSF1, Compound 0005, 0050 and 0009 stabilized the melting temperature of HSF1 but did not affect the melting of an unrelated protein, Hsc70, demonstrating selectivity in binding (see FIG. 2)

Figure 3:
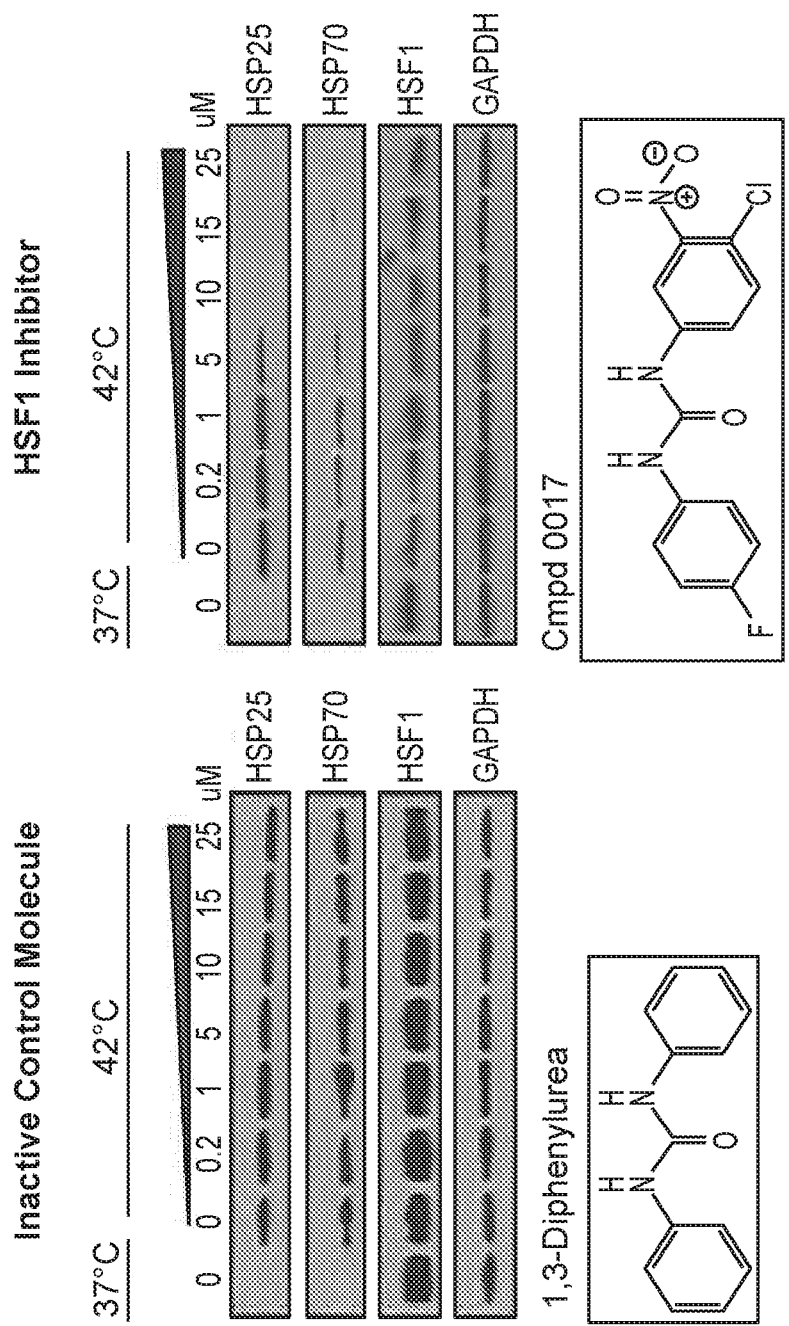
FIG. 3 illustrates that, in Mouse Embryonic Fibroblasts (MEFs), Compound 0017 dose-dependently inhibited the heat shock induced chaperone (Hsp25 and Hsp70) expression by inhibiting HSF1 activity, while the structurally related control molecule (1,3-diphenylurea) showed no impact on HSF1 activity in accordance with one embodiment of the present disclosure. The inactive control molecule is structurally similar to Compound 0017 but fails to bind HSF1. In this experiment, MEFs were pre-treated with a concentration gradient of the inactive control molecule or compound of the disclosure. The MEFs were then subjected to heat shock stress at 42° C. for 30 mins to activate HSF1. After heat shock, the MEFs were incubated at 37° C. for a 6 hour recovery. The whole cell lysates were collected at the end of the experiment, and proteins of interest, including Hsp25, Hsp70, HSF1 and GAPDH (as loading control) were assessed by immunoblotting with the corresponding antibody.

The addition of Compound 0017 inhibits the expression of HSF1 target genes in response to a heat shock in wild type Mouse Embryonic Fibroblasts in vitro (see FIG. 3) whereas the addition of 1,3-diphenylurea, which has the same chemical scaffold as compound 0017, does not.

Figure 5A:
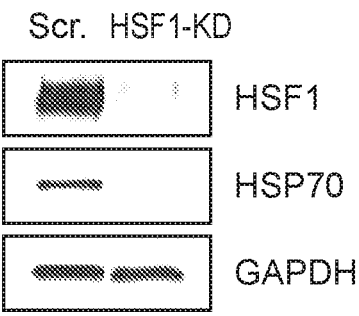
FIG. 5A shows that HSF1 was stably knocked down by shRNA in the C4/2 prostate cancer cell line as shown by immunoblotting for HSF1 and one of its targets, Hsp70. GAPDH was used as a loading control.
Figure 5B:
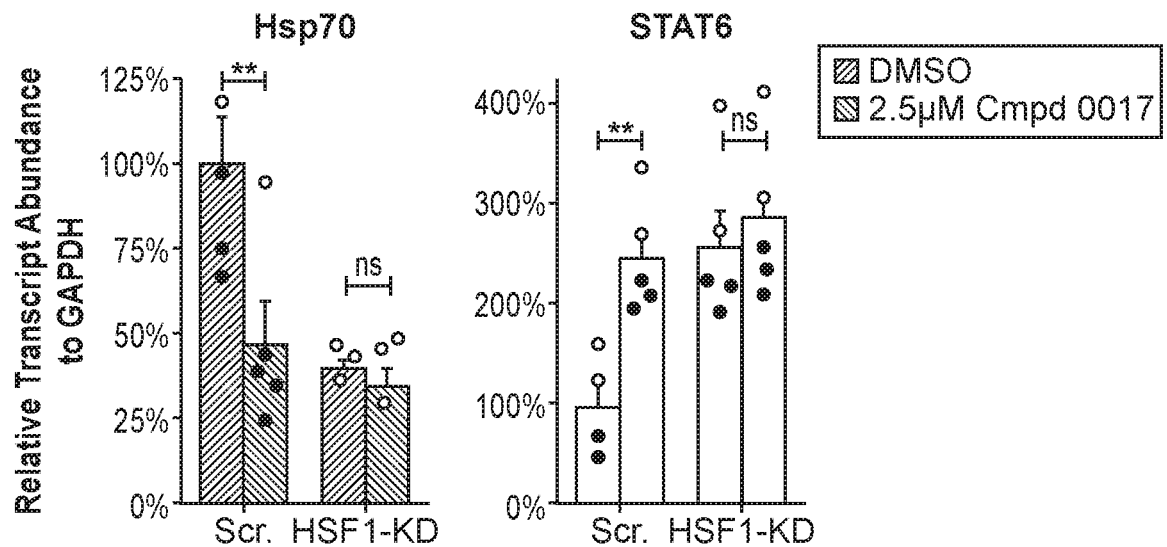
FIG. 5B shows 48-hour treatment with Compound 0017 results in inhibition of Hsp70 expression and de-repression of STAT6 the in C4/2 scramble cell line, but not in the C4/2 HSF1-knockdown cell line. Hsp70 is a gene activated by HSF1 and STAT6 is a gene repressed by HSF1.
Figure 5C:
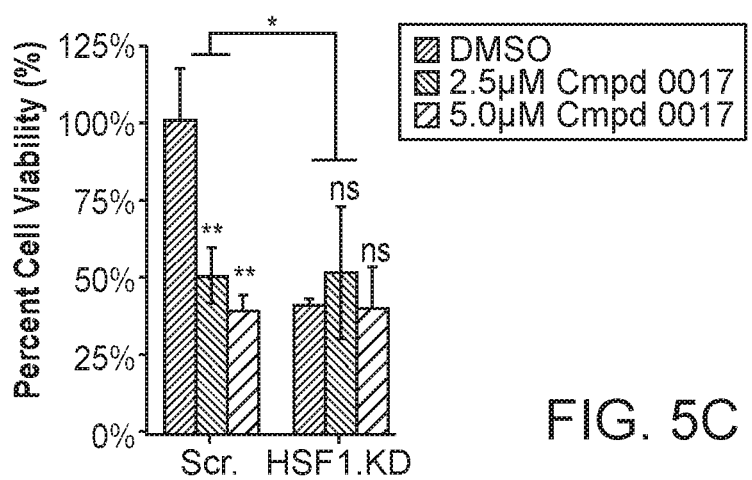
FIG. 5C shows that Compound 0017 preferentially reduces cell viability of C4/2 cells expressing HSF1 (the scrambled shRNA control) compared to the HSF1-knockdown C4/2 cells. This shows a dependency on HSF1 for Compound 0017 action. Shown is the solvent (DMSO) or two concentrations of Compound 0017 at 2.5 and 5 µM. ns=not significant; *=P<0.05; **=P<0.01 in accordance with one embodiment of the present disclosure.

Given the roles of HSF1 in a broad array of cancer types, the molecules disclosed herein, and their derivatives, can be used for treating a wide array of cancer types. The compound of the disclosure, such as Compound 0017, that binds HSF1 in the thermal denaturation assay and that inhibits HSF1 target gene activation in heat-shocked cells, also inhibits HSF1 target gene expression in Prostate Cancer cells, both at the protein level (FIGS. 4A and 4B). Compound 0017 also inhibits target gene regulation by HSF1 (FIG. 4C). The inhibition of HSF1 target gene expression, and prostate cancer cell growth, is dependent on the presence of the HSF1 target protein (FIG. 5).

Based on the chemical structure of Compound 0017 and its activity, and of other HSF1-interacting chemicals identified in the screen, additional derivatives were designed, synthesized and evaluated for binding to HSF1 and preferential inhibition of metastatic prostate cancer cells (C4-2) versus benign prostate cells (BPH-1). The compounds of the disclosure, such as Compound 0054 and Compound 0064, show selectivity for the inhibition of metastatic prostate cancer cell growth over benign prostate cell growth, and have increased potency compared to Compound 0017 (FIG.

Figure 6B:
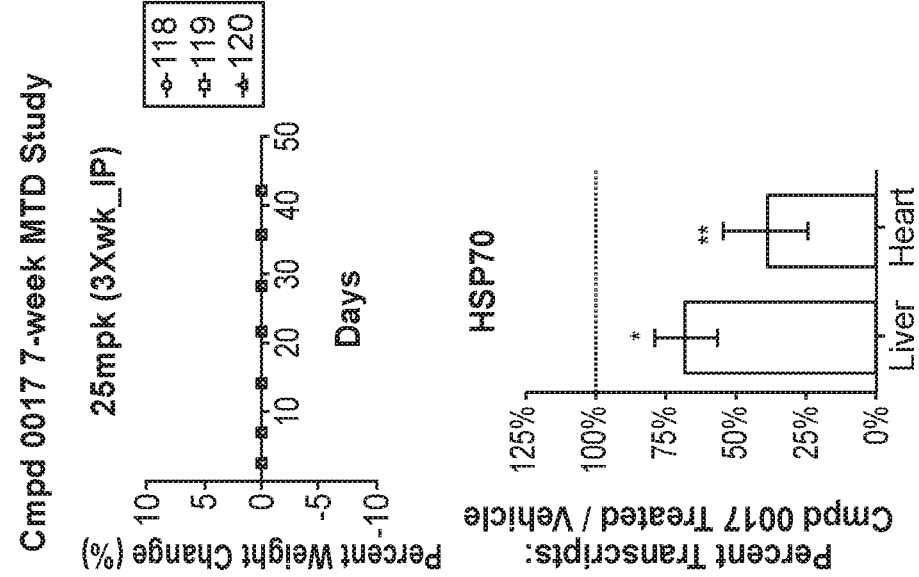
FIG. 6B illustrates the results of Compound 0017 used in a 7-week Maximal Tolerated Dose (MTD) study conducted in mice (3 mice identified as 118, 119 and 120). Compound 0017 was well tolerated when administered at 25 mpk three times per week by intra-peritoneal administration. After sacrificing the mice on the last day of the administration, mouse liver and heart tissue was isolated, messenger RNA extracted and the transcript abundance of the HSF1 target gene, Hsp70, was evaluated by qRT-PCR relative to the internal RNA control, GAPDH. The results of the vehicle-treated versus Compound 0017-treated experiments were compared. The data show that Compound 0017 inhibits expression of the HSF1 target Hsp70 when administered to mice at well tolerated doses. *=P<0.01; **=P<0.01 in accordance with one embodiment of the present disclosure.
Figure 6A:
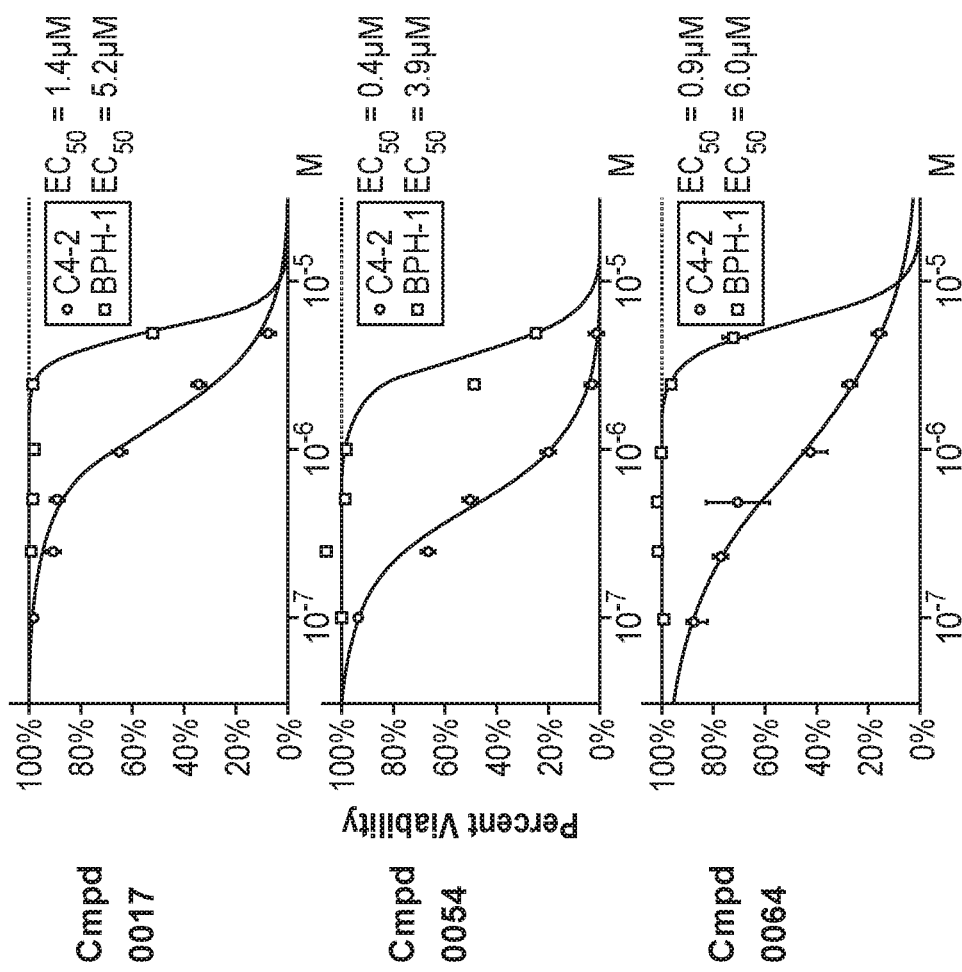
FIG. 6A illustrates that Compounds 0017, 0054, and 0064 preferentially inhibit the viability of malignant prostate cancer cells, C4-2, compared to non-tumorigenic prostate cells, BPH-1. The cells were treated for 96 hours with the indicated concentrations of the compounds of the disclosure and cell viability was measured with the AlamarBlue assay.

6A). The administration of Compound 0017 to mice is well tolerated over at least a seven-week period and tissues isolated from Compound 0017-treated mice show a reduction in Hsp70, a gene activated by HSF1, compared to vehicle treated mice (FIG. 6B).

Figure 7A:
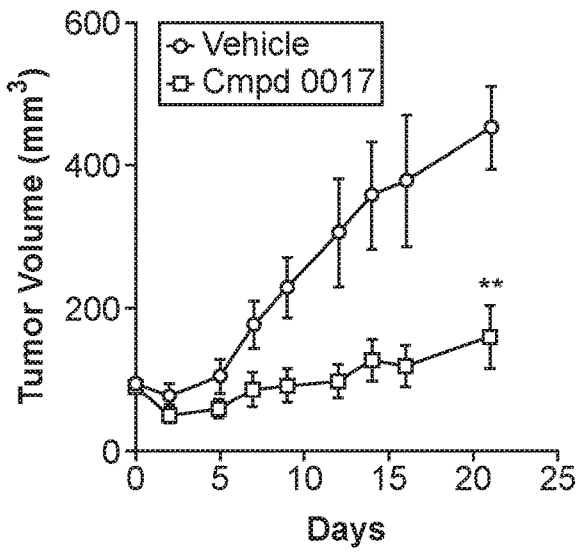
FIGS. 7A and 7B are graphs showing that the compounds of the disclosure inhibit tumor growth in a mouse xenograft model of Prostate Cancer. Nude mice were inoculated on their flank with one million C4/2 prostate cancer cells (n=20 mice). One week after inoculation, tumors were apparent and mice were then treated with either vehicle (n=10 mice) or Compound 0017 (n=10 mice) at 25 mg/kg every other day by intraperitoneal administration. On the indicated days after the start of vehicle or Compound 0017 administration, tumors were measured in situ with a caliper and tumor volume calculated in cubic millimeters (FIG. 7A). Simultaneously, mouse weight was determined (FIG. 7B). Error bars represent standard error of the mean. **=P<0.01 in accordance with one embodiment of the present disclosure.
Figure 7B:
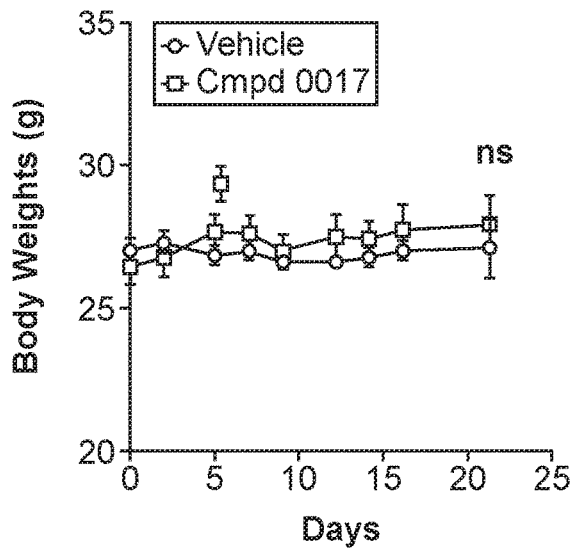
Figure 8:
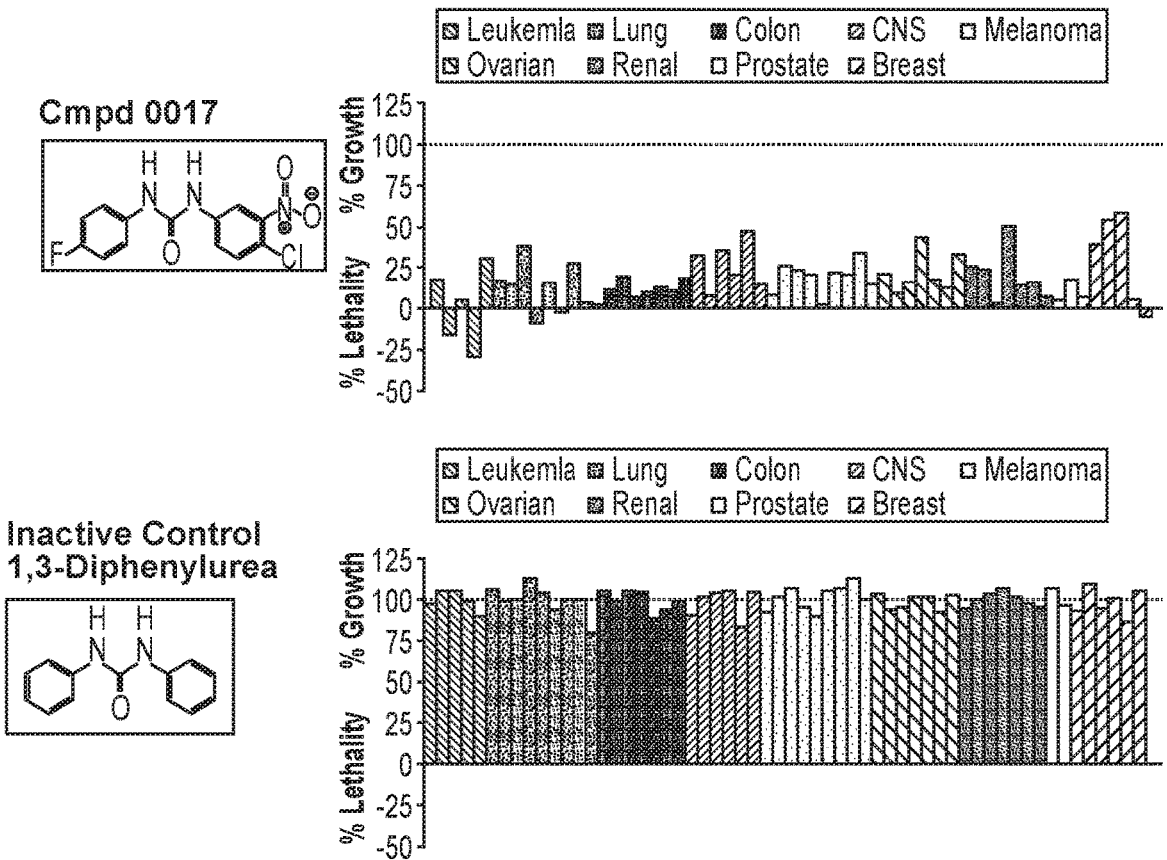
FIG. 8 is a graph showing the compounds of the disclosure suppress the growth of a broad range of cancer types. Compound 0017, or the inactive molecule on the same chemical scaffold, 1,3-diphenylurea, which fails to bind to HSF1, were incubated for two days with a diverse series of cancer cell lines in the NCI60 collection and cell growth and viability measured in accordance with one embodiment of the present disclosure. The cancer origins of the different cell lines are indicated with different colors.

The administration of Compound 0017 inhibits the growth of human prostate cancer cells (C4-2) derived tumors in a mouse xenograft cancer model, compared to vehicle alone, over a 21-day administration period, without impacting the weight of Compound 0017-treated mice compared to vehicle-treated mice (FIGS. 7A-B). Mice receiving this demonstrated that chemicals that bind to HSF1 suppress the growth of cancer cells in vitro and in vivo. Compound 0017, but not 1,3-diphenylurea, inhibited the growth of a broad range of cancer cells (FIG. 8).

The compounds of the disclosure are prepared in view of: (1) the binding of the molecules described above to HSF1; (2) the ability of HSF1 binding molecules to inhibit HSF1 target gene regulation in cell culture; (3) their ability of HSF1 binding molecules to selectively inhibit prostate cancer cell growth compared to benign prostate cells; (4) the ability of a representative HSF1 inhibitor to inhibit prostate cancer tumor growth in a mouse xenograft model using doses that are tolerable in mice; and (5) the efficacy of a representative HSF1 inhibitor to inhibit cell growth for a wide range of cancer cells. The compounds of the disclosure where then confirmed with thermal denaturation assays identifying those that interact with human HSF1 (Table 1).

The compounds of the disclosure that interact with HSF1 and/or inhibit HSF1 activity, in certain embodiments, can be used for the treatment of a wide range of cancers and other diseases in which HSF1 activity is implicated (such as in disease cause, severity or progression). In certain embodiments, the compounds of the disclosure may be used in the treatment of cancer. In certain embodiments, the compounds of the disclosure may be used in the treatment of infectious disease.

Example 2. Differential Scanning Fluorimetry Measurements

Differential Scanning Fluorimetry (DSF) was used to determine molecule binding to HSF1. In short, recombinant HSF1 DNA-binding domain (DBD) and compound of the disclosure were mixed to achieve final reaction condition: 5 µM HSF1 DBD, 25 µM Compound, 25 mM HEPES, 75 mM NaCl, 1 mM $MgCl_2$, 1×SYPRO orange dye, and pH 7.2. The DSF reaction was performed in 384-well format at 20 µL reaction volume via Bio-Rad CFX384 system to measure the melting temperature. The data are reported as the difference in melting temperature ($\Delta Tm$) when the compound is present and when the compound is absent. The positive $\Delta Tm$ values indicate that the compound stabilizes HSF1, and the negative $\Delta Tm$ values indicate that the compound destabilizes HSF1.

TABLE 3

DSF measurement to determine whether the compounds bind to HSF1

| Compound | ΔTm |
|---|---|
| 001 | 4.78 |
| 002 | 1.9 |
| 003 | 1.78 |
| 004 | −9.46 |
| 005 | 5.1 |
| 006 | 2.5 |
| 007 | −10.57 |
| 008 | −4.56 |
| 009 | 4.1 |
| 010 | 5.43 |
| 011 | 2.61 |
| 012 | −4.73 |
| 013 | −7.4 |
| 014 | −4.56 |
| 015 | 3.44 |
| 016 | 2.75 |
| 017 | 3 |
| 018 | 2.44 |
| 019 | −4.27 |
| 020 | 5.2 |
| 021 | −9.19 |
| 022 | 2.78 |
| 023 | 0.67 |
| 024 | 4.44 |
| 025 | −9.21 |
| 026 | 5.75 |
| 027 | 2.8 |
| 028 | −9.69 |
| 029 | −8.96 |
| 030 | −8.57 |
| 031 | −6.23 |
| 032 | 0.75 |
| 033 | 1.9 |
| 034 | 5.7 |
| 035 | 6.44 |
| 036 | 2.61 |
| 037 | −9.74 |
| 038 | 7.27 |
| 039 | −4.28 |
| 040 | −7.95 |
| 041 | −3.11 |
| 042 | −6.23 |
| 043 | −9.07 |
| 044 | 2.33 |
| 045 | −8.21 |
| 046 | 4.3 |
| 047 | 0.75 |
| 048 | 2.61 |
| 049 | 3.11 |
| 050 | 2.93 |
| 051 | −6.91 |
| 052 | −10.96 |
| 053 | −10.07 |
| 054 | 2.9 |
| 055 | −9.69 |
| 056 | −5.96 |
| 057 | −10.46 |
| 058 | 2.58 |
| 059 | −3.45 |
| 060 | 2.5 |
| 061 | 2.94 |
| 062 | −6.9 |
| 063 | 2.5 |
| 064 | 2.3 |
| 065 | 4.44 |
| 066 | 3 |
| 067 | 4 |
| 068 | 2.75 |
| 070 | 8.06 |
| 071 | −7.24 |
| 072 | −6.24 |
| 073 | 3.39 |
| 074 | 2.6 |
| 075 | 2.61 |
| 076 | 2.61 |
| 077 | −7.23 |
| 078 | 2.5 |
| 079 | 2.25 |

TABLE 3-continued

DSF measurement to determine whether the compounds bind to HSF1

| Compound | ΔTm |
|---|---|
| 080 | 1.6 |
| 081 | −3.6 |
| 082 | 3.9 |
| 083 | 2 |
| 084 | −8.96 |
| 085 | 3.26 |
| 086 | −11.46 |
| 087 | −9.24 |
| 088 | −3.02 |
| 089 | −5.73 |
| 090 | 0.67 |
| 091 | 2.5 |
| 092 | 2.33 |
| 093 | −3.44 |
| 094 | 2.92 |
| 095 | 0.67 |
| 096 | 2.61 |
| 097 | 3.43 |
| 098 | 4.93 |
| 099 | −6.74 |
| 100 | −7.52 |
| 101 | 3.33 |
| 102 | −6.23 |
| 103 | 4.7 |
| 104 | 3.27 |
| 105 | 3.2 |
| 106 | 3.28 |
| 107 | −4.4 |
| 108 | −4.19 |
| 109 | −9.02 |
| 110 | 2.94 |
| 111 | −5.21 |
| 112 | 2.08 |
| 113 | 2.28 |
| 114 | 0.49 |
| 115 | −9.91 |
| 116 | −5.56 |

Example 3: Preparation of 3-(4-chloro-3-nitro-anilino)-4-(4-fluoroanilino)cyclobut-3-ene-1,2-dione (Compound 0002)

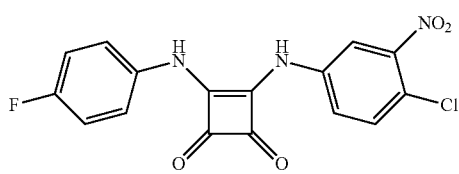

Step 1: Preparation of 3-(4-chloro-3-nitro-anilino)-4-ethoxy-cyclobut-3-ene-1,2-dione: To a solution of 4-chloro-3-nitro-aniline (0.4 g, 2.32 mmol, 1 eq) in EtOH (20 mL) was added 3,4-diethoxycyclobut-3-ene-1,2-dione (394.42 mg, 2.32 mmol, 340.02 uL, 1 eq). The mixture was stirred at 25° C. for 24 hours. The mixture was heated to 65° C. and stirred at stirred at 65° C. for 12 hours. The mixture was concentrated directly under reduced pressure to afford a residue. The residue was purified by flash silica gel chromatography (ISCO®; 12 g SepaFlash® Silica Flash Column, Eluent of 0~10% Ethyl acetate/Petroleum ether gradient@36 mL/min) to afford the compound 3-(4-chloro-3-nitro-anilino)-4-ethoxy-cyclobut-3-ene-1,2-dione (0.36 g, 1.21 mmol, 52.35% yield) as a yellow solid. $^1$H NMR: (400 MHz, DMSO-d6) δ 11.13 (brs, 1H), 8.10 (d, J=2.4 Hz, 1H), 7.76 (d, J=8.8 Hz, 1H), 7.64-7.66 (dd, J=8.8 Hz, 2.4 Hz, 1H), 4.76-4.81 (m, 2H), 1.43 (t, J=1.2 Hz, 3H).

Step 2: Preparation of 3-(4-chloro-3-nitro-anilino)-4-(4-fluoroanilino)cyclobut-3-ene-1,2-dione: To a solution of 3-(4-chloro-3-nitro-anilino)-4-ethoxy-cyclobut-3-ene-1,2-dione (0.05 g, 168.54 μmol, 1 eq) in THF (2 mL) was added AlMe$_3$ (1 M, 252.81 uL, 1.5 eq) and 4-fluoroaniline (22.47 mg, 202.25 μmol, 19.37 uL, 1.2 eq) at 20° C. After addition, the mixture was heated to 65° C. and stirred at 65° C. for 12 hours. The mixture was quenched by addition of H$_2$O (15 mL) at 0° C., extracted with EtOAc (20 mL×2). The combined organic layers were washed with H$_2$O (20 mL), brine (20 mL), dried over Na$_2$SO$_4$ and filtered. The filtrate was concentrated under reduced pressure to afford a residue. The residue was purified by recrystallization in MeOH (5 mL) and further purified by prep-HPLC (neutral condition, column: XtimateC18 150*25 mm*5 um; mobile phase: [water(10 mM NH$_4$HCO$_3$)-ACN]; B %: 40%-70%, 10 min) to afford the compound 3-(4-chloro-3-nitro-anilino)-4-(4-fluoroanilino)cyclobut-3-ene-1,2-dione (5.90 mg, 15.38 μmol, 9.12% yield, 94.26% purity) as a light-yellow solid with purity 94.26% on LCMS. $^1$H NMR: (400 MHz, DMSO-d6) δ 8.15 (s, 1H), 7.68-7.73 (m, 2H), 7.45-7.49 (m, 2H), 7.19-7.24 (m, 2H).

Example 4: Preparation of 1-(4-fluorophenyl)-3-(3-(trifluoromethyl)phenyl)urea (Compound 0003)

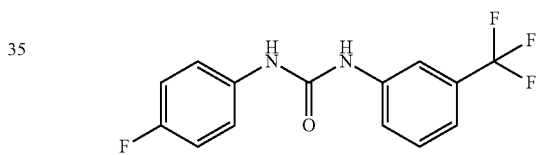

1-fluoro-4-isocyanatobenzene (1.0 equiv) and 3-(trifluoromethyl)aniline (1.0 equiv) were dissolved in dichloromethane (each 0.5 M) and stirred gently at 25° C. for 48 hours. 1-(4-fluorophenyl)-3-(3-(trifluoromethyl)phenyl)urea was collected by filtration, washed with dichloromethane, and dried under vacuum.

Example 5: Preparation of 1-(4-bromo-3-(trifluoromethyl)phenyl)-3-(4-fluorophenyl)urea (Compound 0005)

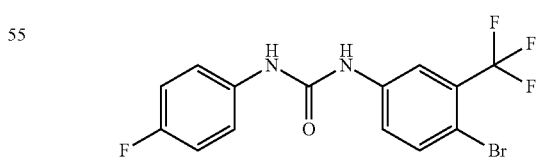

1-fluoro-4-isocyanatobenzene (1.0 equiv) and 4-bromo-3-(trifluoromethyl)aniline (1.0 equiv) were dissolved in dichloromethane (each 0.5 M) and stirred gently at 25° C. for 48 hours. 1-(4-bromo-3-(trifluoromethyl)phenyl)-3-(4-fluorophenyl)urea was collected by filtration, washed with dichloromethane, and dried under vacuum.

Example 6: Preparation of 1-(3-chlorophenyl)-3-(m-tolyl)urea (Compound 0006)

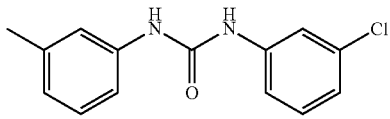 [SMILES: Cc1cccc(NC(=O)Nc2cccc(Cl)c2)c1]

1-isocyanato-3-methylbenzene (1.0 equiv) and 3-chloroaniline (1.0 equiv) were dissolved in dichloromethane (each 0.5 M) and stirred gently at 25° C. for 48 hours. 1-(3-chlorophenyl)-3-(m-tolyl)urea was collected by filtration, washed with dichloromethane, and dried under vacuum.

Example 7: Preparation of 1-(4-methoxyphenyl)-3-(p-tolyl)urea (Compound 0011)

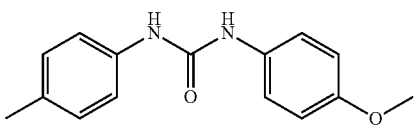

1-isocyanato-4-methylbenzene (1.0 equiv) and 4-methoxyaniline (1.0 equiv) were dissolved in dichloromethane (each 0.5 M) and stirred gently at 25° C. for 48 hours. 1-(4-methoxyphenyl)-3-(p-tolyl)urea was collected by filtration, washed with dichloromethane, and dried under vacuum.

Example 8: Preparation of 3-[4-chloro-3-(trifluoromethylsulfonyl)anilino]-4-(3,4-difluoroanilino)cyclobut-3-ene-1,2-dione (Compound 0016)

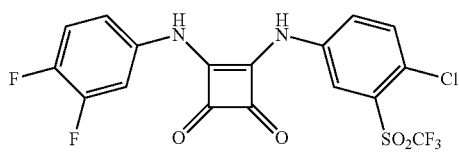

To a solution of 3-[4-chloro-3-(trifluoromethylsulfonyl)anilino]-4-ethoxy-cyclobut-3-ene-1,2-dione (0.06 g, 156.36 μmol, 1 eq) in THF (2 mL) was added 3,4-difluoroaniline (20.19 mg, 156.36 μmol, 14.98 uL, 1 eq) and AlMe₃ (2 M, 156.36 uL, 2 eq). The mixture was stirred at 70° C. for 12 hours. The mixture was quenched by addition of saturated aqueous NH₄Cl (5 mL) at 0° C., diluted with EtOAc (20 mL) and filtered. The organic layers were washed with H₂O (10 mL), brine (10 mL), dried over Na₂SO₄ and filtered. The filtrate was concentrated under reduced pressure to afford a residue. The residue was purified by prep-HPLC (basic condition, column: Kromasil 150*25 mm*10 um; mobile phase: [water(0.04% NH₃H₂O+10 mM NH₄HCO₃)-ACN]; B %: 40%-60%, 10 min) to afford the compound 3-[4-chloro-3-(trifluoromethylsulfonyl)anilino]-4-(3,4-difluoroanilino)cyclobut-3-ene-1,2-dione (0.0135 g, 27.16 μmol, 17.37% yield, 93.92% purity) as a light-yellow solid. ¹H NMR: (DMSO-d6, 400 MHz) δ 8.23 (s, 1H), 7.86-7.93 (m, 2H), 7.59 (m, 1H), 7.40-7.44 (m, 1H), 7.15-7.17 (m, 1H)

Example 9: Preparation of 1-(4-chloro-3-nitrophenyl)-3-(4-fluorophenyl)urea (Compound 0017)

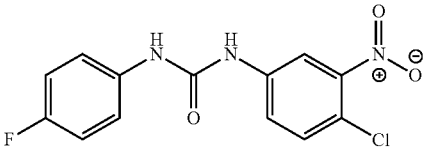 [SMILES: O=C(Nc1ccc(F)cc1)Nc1ccc(Cl)c([N+](=O)[O-])c1]

1-fluoro-4-isocyanatobenzene (1.0 equiv) and 4-chloro-3-nitroaniline (1.0 equiv) were dissolved in dichloromethane (each 0.5 M) and stirred gently at 25° C. for 48 hours. 1-(4-chloro-3-nitrophenyl)-3-(4-fluorophenyl)urea was collected by filtration, washed with dichloromethane, and dried under vacuum. ¹H NMR: (Chloroform-d, 400 MHz) δ 7.96 (d, J=2.5 Hz, 1H), 7.69 (dd, J=8.4, 2.4 Hz, 1H), 7.39 (d, J=8.9 Hz, 1H), 7.35 (dd, J=8.8, 4.7 Hz, 2H), 6.99 (t, J=8.6 Hz, 2H).

Example 10: Preparation of 1,3-bis(4-chlorophenyl)urea (Compound 0018)

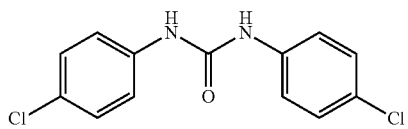 [SMILES: O=C(Nc1ccc(Cl)cc1)Nc1ccc(Cl)cc1]

1-chloro-4-isocyanatobenzene (1.0 equiv) and 4-chloroaniline (1.0 equiv) were dissolved in dichloromethane (each 0.5 M) and stirred gently at 25° C. for 48 hours. 1,3-bis(4-chlorophenyl)urea was collected by filtration, washed with dichloromethane, and dried under vacuum.

Example 11: Preparation of 1-(4-chloro-3-nitrophenyl)-3-(3-fluorophenyl)urea (Compound 0020)

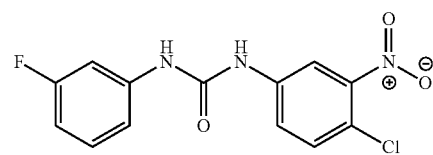 [SMILES: O=C(Nc1cccc(F)c1)Nc1ccc(Cl)c([N+](=O)[O-])c1]

1-fluoro-3-isocyanatobenzene (1.0 equiv) and 4-chloro-3-nitroaniline (1.0 equiv) were dissolved in dichloromethane (each 0.5 M) and stirred gently at 25° C. for 48 hours. 1-(4-chloro-3-nitrophenyl)-3-(3-fluorophenyl)urea was collected by filtration, washed with dichloromethane, and dried under vacuum.

Example 12: Preparation of 1-(3,4-dichlorophenyl)-3-phenylurea (Compound 0022)

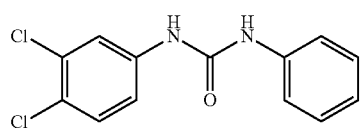 [SMILES: O=C(Nc1ccccc1)Nc1ccc(Cl)c(Cl)c1]

1,2-dichloro-4-isocyanatobenzene (1.0 equiv) and aniline (1.0 equiv) were dissolved in dichloromethane (each 0.5 M) and stirred gently at 25° C. for 48 hours. 1-(3,4-dichlorophenyl)-3-phenylurea was collected by filtration, washed with dichloromethane, and dried under vacuum.

Example 13: Preparation of 3-(4-chloro-3-nitrophenyl)-1-(4-fluorophenyl)-1-methyl-urea (Compound 0023)

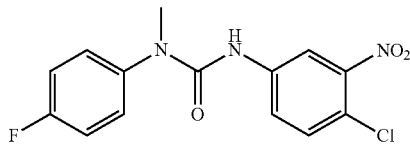 [SMILES: CN(C(=O)Nc1ccc(Cl)c([N+](=O)[O-])c1)c1ccc(F)cc1]

Step 1: Preparation of N-(4-chloro-3-nitro-phenyl)carbamoyl chloride: To a solution of 4-chloro-3-nitro-aniline (0.4 g, 2.32 mmol, 1 eq) in THF (5 mL) was added triphosgene (687.84 mg, 2.32 mmol, 1 eq) and TEA (703.65 mg, 6.95 mmol, 967.88 uL, 3 eq). The mixture was stirred at 0° C. for 1 h. The reaction mixture was used to the next step directly.

Step 2: Preparation of 3-(4-chloro-3-nitro-phenyl)-1-(4-fluorophenyl)-1-methyl-urea: To a solution of N-(4-chloro-3-nitro-phenyl)carbamoyl chloride (0.136 g, 578.66 µmol, 1 eq) in THF (1 mL) was added TEA (117.11 mg, 1.16 mmol, 161.09 uL, 2 eq) and 4-fluoro-N-methyl-aniline (144.83 mg, 1.16 mmol, 139.26 uL, 2 eq) at 0° C. The mixture was stirred at 25° C. for 3 hours. The mixture was poured to water (10 mL) and extracted with EtOAc (10 mL*2). The combined organic layers were washed with brine (10 mL*2), dried over Na$_2$SO$_4$, filtered and concentrated under reduced pressure to give a residue. The residue was purified by prep-HPLC (neutral condition) to afford the title compound (32.1 mg, 97.25 µmol, 16.81% yield, 98.070% purity) as a white solid. $^1$H NMR: (400 MHz, DMSO-d6) δ8.66 (s, 1H), 8.24 (d, J=2.4 Hz, 1H), 7.80 (dd, J=2.6, 8.9 Hz, 1H), 7.61 (d, J=8.8 Hz, 1H), 7.43-7.36 (m, 2H), 7.30-7.22 (m, 2H), 3.24 (s, 3H).

Example 14: Preparation of 1-(4-chloro-3-nitrophenyl)-3-(m-tolyl)urea (Compound 0026)

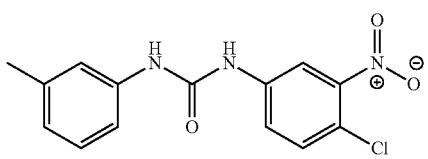 [SMILES: Cc1cccc(NC(=O)Nc2ccc(Cl)c([N+](=O)[O-])c2)c1]

1-isocyanato-3-methylbenzene (1.0 equiv) and 4-chloro-3-nitroaniline (1.0 equiv) were dissolved in dichloromethane (each 0.5 M) and stirred gently at 25° C. for 48 hours. 1-(4-chloro-3-nitrophenyl)-3-(m-tolyl)urea was collected by filtration, washed with dichloromethane, and dried under vacuum.

Example 15: Preparation of 1-(2,1,3-benzoxadiazol-5-yl)-3-(4-fluorophenyl)urea (Compound 0027)

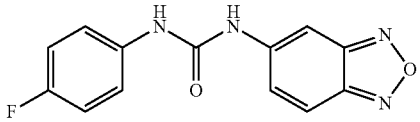 [SMILES: O=C(Nc1ccc(F)cc1)Nc1ccc2nonc2c1]

Step 1: Preparation of 4-bromo-9-oxido-8-oxa-7,9diazabicyclo[4.3.0]nona-1(9),2,4,6-tetraene: A stirred solution of KOH (594.66 mg, 10.60 mmol, 1 eq) in EtOH (25 mL) at 47° C. was treated in portions with 4-bromo-2-nitro-aniline (2.3 g, 10.60 mmol, 1 eq) such that the temperature remained stable and then was heated at 65° C. for 2 hours. The deep-red reaction mixture was then cooled to 2° C., treated drop-wise with an aqueous solution of NaOCl (134.64 g, 126.61 mmol, 111.28 mL, 7% purity, 11.95 eq) and stirred for 90 min at <5° C., followed by 18 h at 10-20° C. The mixture was filtered and the filter cake was washed with H$_2$O (30 mL)*3, dried in vacuum to afford the crude product 4-bromo-9-oxido-8-oxa-7,9diazabicyclo[4.3.0]nona-1(9),2,4,6-tetraene (1.9 g, crude) as a yellow solid which was used into the next step without further purification.

Step 2: Preparation of 5-bromo-2,1,3-benzoxadiazole: To a solution of PPh$_3$ (2.67 g, 10.16 mmol, 1.15 eq) in XYLENE (26 mL) was added a solution of 4-bromo-9-oxido-8-oxa-7,9diazabicyclo[4.3.0]nona-1(9),2,4,6-tetraene (1.9 g, 8.84 mmol, 1 eq) in xylene (5 mL) at 130° C. over 20 min. The mixture was stirred at 130° C. for another 4 hours. The reaction mixture was concentrated under reduced pressure to give a residue. The residue was purified by flash silica gel chromatography (ISCO®; 80 g SepaFlash® Silica Flash Column, Eluent of 0~100% Ethyl acetate/Petroleum ether gradient@100 mL/min) to afford a product with purity about 35% on $^1$H NMR. The product was purified again by flash silica gel chromatography (ISCO®; 20 g SepaFlash® Silica Flash Column, Eluent of 0~100% Ethyl acetate/Petroleum ether gradient@50 mL/min) to afford the compound 5-bromo-2,1,3-benzoxadiazole (0.7 g, 3.32 mmol, 37.60% yield, 94.46% purity) as a brown solid with purity 94.46% on LCMS.

Step 3: Preparation of 2,1,3-benzoxadiazol-5-amine: A mixture of 5-bromo-2,1,3-benzoxadiazole (0.7 g, 3.52 mmol, 1 eq), Pd$_2$(dba)$_3$ (161.05 mg, 175.88 µmol, 0.05 eq) and tritert-butylphosphonium; tetrafluoroborate (204.11 mg, 703.50 µmol, 0.2 eq) in toluene (40 mL) was degassed and purged with N$_2$ for 3 times, and then LiHMDS (1 M, 7.04 mL, 2 eq) was added drop-wise at the mixture was stirred at 50° C. for 11 hours under N$_2$ atmosphere. After cooling to 25° C., the mixture was diluted with MTBE (100 mL) and HCl (1 M, 3.52 mL, 1 eq) was added. The mixture was stirred for another 1 h. The mixture was diluted with EtOAc (100 mL), washed with saturated aq NaHCO$_3$ (100 mL), brine (100 mL), dried over Na$_2$SO$_4$ and filtered. The filtrate was concentrated under reduced pressure to afford a residue. The residue was purified by flash silica gel chromatography (ISCO®; 12 g SepaFlash® Silica Flash Column, Eluent of 0~100% Ethyl acetate/Petroleum ether gradient@36 mL/min) to afford the compound 2,1,3-benzoxadiazol-5-amine (0.21 g, 1.45 mmol, 41.13% yield, 93.1% purity) as a gray solid with purity 93.1% on LCMS.

Step 4: Preparation of 1-(2,1,3-benzoxadiazol-5-yl)-3-(4-fluorophenyl)urea: To a solution of 4-fluoroaniline (45.23 mg, 407.04 µmol, 38.99 uL, 1.1 eq) in THF (5 mL) was added triphosgene (54.90 mg, 185.02 µmol, 0.5 eq) and TEA (112.33 mg, 1.11 mmol, 154.51 uL, 3 eq) at 0° C. The mixture was warmed to 25° C. and stirred at for 2 hours, and then 2,1,3-benzoxadiazol-5-amine (0.05 g, 370.03 µmol, 1 eq) was added. The mixture was stirred at 25° C. for 10 hours. The mixture was concentrated directly under reduced pressure. The residue was washed with $H_2O$, (5 mL*2) and dried in vacuum to afford the crude product. The residue was purified by prep-HPLC (HCl condition; column: HUAPU C8 Extreme BDS 150*30 5 u; mobile phase: [water(0.04% HCl)-ACN]; B %: 40%-55%, 11 min) to afford the compound 1-(2,1,3-benzoxadiazol-5-yl)-3-(4-fluorophenyl)urea (0.01 g, 35.90 µmol, 9.70% yield, 97.73% purity) as a off-white solid with purity 97.73% on LCMS. $^1$H NMR: (400 MHz, DMSO-d6) δ 8.11 (s, 1H), 7.79-7.81 (m, 1H), 7.42-7.45 (m, 2H), 7.31-7.33 (m, 1H), 7.01-7.05 (m, 2H).

Example 16: Preparation of 1-[4-chloro-3-(trifluoromethyl)phenyl]-3-(4-fluorophenyl)guanidine (Compound 0032)

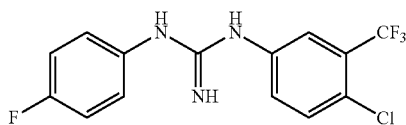 [SMILES: N=C(Nc1ccc(F)cc1)Nc1ccc(Cl)c(C(F)(F)F)c1]

Step 1: Preparation of 1-fluoro-4-isothiocyanato-benzene: 4-fluoroaniline (4 g, 36.00 mmol, 3.45 mL, 1 eq) and TEA (14.54 g, 143.68 mmol, 20.00 mL, 3.99 eq) was dissolved into THF (40 mL), then $CS_2$ (5.04 g, 66.19 mmol, 4.00 mL, 1.84 eq) was added to the mixture at 0° C. Then TEA (5.82 g, 57.47 mmol, 8.00 mL, 1.60 eq) was added to the mixture. The mixture was stirred at 25° C. for 12 hours. Then the mixture was cooled to 0° C., TosCl (8.24 g, 43.20 mmol, 1.2 eq) at 0° C. The mixture was stirred at 0° C. for 1 hour. The reaction mixture was diluted with aqueous of HCl (1 M, 40 mL) and extracted with EtOAc (40 mL). The combined organic layers were washed with brine (20 mL), dried over $Na_2SO_4$, filtered and concentrated under reduced pressure to give a residue. The residue was purified by flash silica gel chromatography (ISCO®; 20 g SepaFlash® Silica Flash Column, Eluent of 0~3% Ethyl acetate/Petroleum ether gradient@75 mL/min) to afford the compound 1-fluoro-4-isothiocyanato-benzene (4.5 g, 29.38 mmol, 81.61% yield) as a light-yellow oil. $^1$H NMR: (400 MHz, MeOD) δ 8.05-7.97 (m, 2H), 7.85-7.76 (m, 2H).

Step 2: Preparation of 1-[4-chloro-3-(trifluoromethyl)phenyl]-3-(4-fluorophenyl)thiourea: A mixture of 4-chloro-3-(trifluoromethyl) aniline (638.38 mg, 3.26 mmol, 1 eq) in DMF (5 mL) was added NaH (156.67 mg, 3.92 mmol, 60% purity, 1.2 eq) at 0° C. Then the mixture was stirred at 0° C. for 30 min, then 1-fluoro-4-isothiocyanatobenzene (0.5 g, 3.26 mmol, 1 eq) was added to the mixture. The mixture was stirred at 25° C. for 2 hours. The mixture was poured to water (10 mL) and extracted with EtOAc (10 mL*2). The combined organic layers were washed with brine (10 mL*2), dried over $Na_2SO_4$, filtered and concentrated under reduced pressure to give a residue. The residue was purified by flash silica gel chromatography (ISCO®; 12 g SepaFlash® Silica Flash Column, Eluent of 0~50% Ethyl acetate/Petroleum ether gradient@36 mL/min) to afford compound 1-[4-chloro-3-(trifluoromethyl) phenyl]-3-(4-fluorophenyl)thiourea (0.58 g, 1.16 mmol, 35.66% yield, 70% purity) was obtained as yellow gum.

Step 3: Preparation of 1-[4-chloro-3-(trifluoromethyl) phenyl]-3-(4-fluorophenyl) guanidine: To a mixture of 1-[4-chloro-3-(trifluoromethyl)phenyl]-3-(4-fluorophenyl)thiourea (0.2 g, 573.48 µmol, 1 eq) in $NH_3$. $H_2O$ (1 mL) and MeOH (1 mL) was added triacetoxyplumbyl acetate (1.27 g, 2.87 mmol, 5 eq). The mixture was stirred at 80° C. for 0.5 hour. The reaction mixture was filtered and concentrated under reduced pressure to give a residue. The residue was purified by prep-HPLC (neutral condition) to afford compound 1-[4-chloro-3-(trifluoromethyl)phenyl]-3-(4-fluorophenyl)guanidine (14.3 mg, 42.80 µmol, 7.46% yield, 99.27% purity) as a white solid. $^1$H NMR: (400 MHz, MeOD) δ 7.55 (d, J=2.4 Hz, 1H), 7.45 (d, J=8.6 Hz, 1H), 7.34 (dd, J=2.4, 8.7 Hz, 1H), 7.23 (dd, J=4.8, 9.0 Hz, 2H), 7.03 (t, J=8.8 Hz, 2H).

Example 17: Preparation of $N_3$-[4-chloro-3-(trifluoromethyl)phenyl]-$N_4$-(4-fluorophenyl)-1,1-dioxo-1,2,5-thiadiazole-3,4-diamine (Compound 0033)

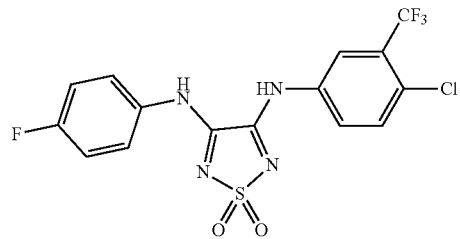 [SMILES: O=S1(=O)N=C(Nc2ccc(F)cc2)C(Nc2ccc(Cl)c(C(F)(F)F)c2)=N1]

To a solution of 3,4-diethoxy-1,2,5-thiadiazole 1,1-dioxide (0.035 g, 169.72 µmol, 1 eq), 4-chloro-3-(trifluoromethyl)aniline (33.19 mg, 169.72 µmol, 1 eq), 4-fluoroaniline (18.86 mg, 169.72 µmol, 16.26 uL, 1 eq) in toluene (2 mL) was added $AlMe_3$ (2 M, 424.30 uL, 5 eq) drop-wise slowly at 25° C. After addition, the mixture was taken up into a microwave tube. The sealed tube was heated at 120° C. for 2 hours under microwave. The mixture was quenched by addition of aq HCl (2M, 5 mL) at 25° C., extracted with EtOAc (5 mL*2). The combined organic layers were washed with $H_2O$ (5 mL), brine (5 mL), dried over $Na_2SO_4$ and filtered. The filtrate was concentrated under reduced pressure to afford a residue. The residue was purified by prep-HPLC (TFA condition; column: Waters Xbridge Prep OBD C18 150*30 5 u; mobile phase: [water(0.1% TFA)-ACN]; B %: 40%-80%, 13 min) to afford the compound $N_3$-[4-chloro-3-(trifluoromethyl)phenyl]-$N_4$-(4-fluorophenyl)-1,1-dioxo-1,2,5-thiadiazole-3,4-diamine (0.0096 g, 22.62 µmol, 13.33% yield, 99.16% purity) as a white solid with purity 99.16% on LCMS. $^1$H NMR: (400 MHz, MeOD) δ 8.28 (d, J=2.8 Hz, 1H), 8.11 (d, J=8.4 Hz, 1H), 7.84-7.87 (m, 2H), 7.76 (d, J=8.4 Hz, 1H), 7.23-7.27 (m, 2H).

Example 18: Preparation of 1-(4-chloro-3-nitrophenyl)-3-(3,4-difluorophenyl)urea (Compound 0034)

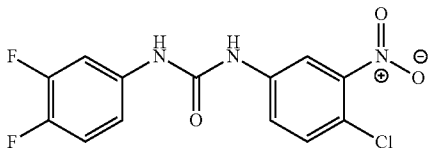 [SMILES: O=C(Nc1ccc(F)c(F)c1)Nc1ccc(Cl)c([N+](=O)[O-])c1]

1,2-difluoro-4-isocyanatobenzene (1.0 equiv) and 4-chloro-3-nitroaniline (1.0 equiv) were dissolved in dichloromethane (each 0.5 M) and stirred gently at 25° C. for 48 hours. 1-(4-chloro-3-nitrophenyl)-3-(3,4-difluorophenyl)urea was collected by filtration, washed with dichloromethane, and dried under vacuum.

Example 19: Preparation of 1-(4-chlorophenyl)-3-(4-methoxyphenyl)urea (Compound 0036)

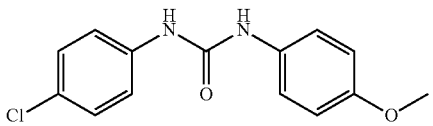 [SMILES: COc1ccc(NC(=O)Nc2ccc(Cl)cc2)cc1]

1-chloro-4-isocyanatobenzene (1.0 equiv) and 4-methoxyaniline (1.0 equiv) were dissolved in dichloromethane (each 0.5 M) and stirred gently at 25° C. for 48 hours. 1-(4-chlorophenyl)-3-(4-methoxyphenyl)urea was collected by filtration, washed with dichloromethane, and dried under vacuum.

Example 20: Preparation of 1-(4-chloro-3-nitrophenyl)-3-(3,4-dichlorophenyl)urea (Compound 0044)

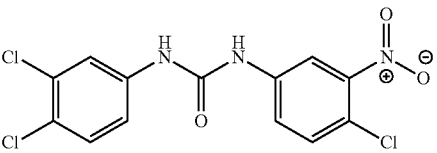 [SMILES: O=C(Nc1ccc(Cl)c(Cl)c1)Nc1ccc(Cl)c([N+](=O)[O-])c1]

1,2-dichloro-4-isocyanatobenzene (1.0 equiv) and 4-chloro-3-nitroaniline (1.0 equiv) were dissolved in dichloromethane (each 0.5 M) and stirred gently at 25° C. for 48 hours. 1-(4-chloro-3-nitrophenyl)-3-(3,4-dichlorophenyl)urea was collected by filtration, washed with dichloromethane, and dried under vacuum.

Example 21: Preparation of 1-(4-chloro-3-nitrophenyl)-3-(p-tolyl)urea (Compound 0046)

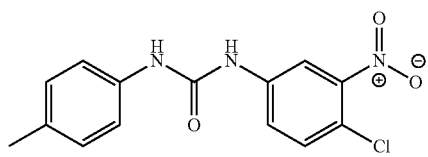 [SMILES: Cc1ccc(NC(=O)Nc2ccc(Cl)c([N+](=O)[O-])c2)cc1]

1-isocyanato-4-methylbenzene (1.0 equiv) and 4-chloro-3-nitroaniline (1.0 equiv) were dissolved in dichloromethane (each 0.5 M) and stirred gently at 25° C. for 48 hours. 1-(4-chloro-3-nitrophenyl)-3-(p-tolyl)urea was collected by filtration, washed with dichloromethane, and dried under vacuum.

Example 22: Preparation of 1-(4-chloro-3-nitrophenyl)-2-cyano-3-(4-fluorophenyl)guanidine (Compound 0047)

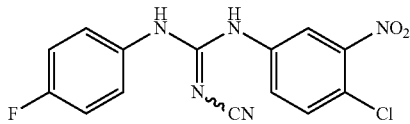 [SMILES: N#CN=C(Nc1ccc(F)cc1)Nc1ccc(Cl)c([N+](=O)[O-])c1]

Step 1: Preparation of 1-fluoro-4-isothiocyanato-benzene: 4-fluoroaniline (2 g, 18.00 mmol, 1.72 mL, 1 eq) and TEA (7.27 g, 71.85 mmol, 10 mL, 3.99 eq) was dissolved into THF (20 mL), then $CS_2$ (2.52 g, 33.10 mmol, 2 mL, 1.84 eq) was added to the mixture at 0° C. Then TEA (2.91 g, 28.74 mmol, 4 mL, 1.60 eq) was added to the mixture. The mixture was stirred at 25° C. for 12 hours. Then the mixture was cooled to 0° C. Then TosCl (4.12 g, 21.60 mmol, 1.2 eq) was added to the mixture slowly. The mixture was stirred at 0° C. for 1 hour. The reaction mixture was diluted with aqueous of HCl (1 M, 20 mL) and extracted with EtOAc (20 mL). The combined organic layers were washed with brine (20 mL), dried over $Na_2SO_4$, filtered and concentrated under reduced pressure to give a residue. The residue was purified by flash silica gel chromatography (ISCO®; 20 g SepaFlash® Silica Flash Column, Eluent of 0~30% Ethyl acetate/Petroleum ether gradient@36 mL/min) to afford compound 1-fluoro-4-isothiocyanato-benzene (2.7 g, 17.63 mmol, 97.93% yield) as yellow oil. $^1$H NMR: (400 MHz, DMSO-d6) δ 7.54-7.48 (m, 2H), 7.34-7.27 (m, 2H).

Step 2: Preparation of 1-(4-chloro-3-nitro-phenyl)-3-(4-fluorophenyl) thiourea: To a mixture of 1-fluoro-4-isothiocyanato-benzene (2.3 g, 15.02 mmol, 1 eq) in DMF (20 mL) was added NaH (720.67 mg, 18.02 mmol, 60% purity, 1.2 eq) at 0° C. Then the mixture was stirred at 0° C. for 30 min. Then 4-chloro-3-nitro-aniline (2.59 g, 15.02 mmol, 1 eq) was added to the mixture. The mixture was stirred at 25° C. for 1 hour. The mixture was poured to water (10 mL) and extracted with EtOAc (10 mL*2). The combined organic layers were washed with brine (10 mL*2), dried over $Na_2SO_4$, filtered and concentrated under reduced pressure to give a residue. The residue was purified by flash silica gel chromatography (ISCO®; 40 g SepaFlash® Silica Flash Column, Eluent of 0~70% Ethyl acetate/Petroleum ether gradient@100 mL/min) to afford compound 1-(4-chloro-3-nitro-phenyl)-3-(4-fluorophenyl) thiourea (1.7 g, 4.33 mmol, 28.85% yield, 83% purity) as yellow oil.

Step 3: Preparation of 3-(4-chloro-3-nitro-phenyl)-1-(4-fluorophenyl)-2-methyl-isothiourea: To a mixture of 1-(4-chloro-3-nitro-phenyl)-3-(4-fluorophenyl)thiourea (0.5 g, 1.53 mmol, 1 eq) in acetone (2 mL) was added MeI (435.74 mg, 3.07 mmol, 191.11 uL, 2 eq) and $K_2CO_3$ (424.28 mg, 3.07 mmol, 2 eq). The mixture was stirred at 80° C. for 2 hours. The mixture was filtered and concentrated under reduced pressure to give a residue. The residue was purified by flash silica gel chromatography (ISCO®; 12 g SepaFlash® Silica Flash Column, Eluent of 0~30% Ethyl acetate/Petroleum ether gradient@36 mL/min) to afford compound 3-(4-chloro-3-nitro-phenyl)-1-(4-fluorophenyl)-2-methyl-isothiourea (0.4 g, 517.99 μmol, 33.75% yield, 44% purity) as yellow oil. $^1$H NMR: (400 MHz, DMSO-d6) δ 7.71-7.49 (m, 3H), 7.26-7.01 (m, 4H), 2.50 (br s, 3H).

Step 4: Preparation of 1-(4-chloro-3-nitro-phenyl)-2-cyano-3-(4-fluorophenyl)guanidine: 3-(4-chloro-3-nitro-phenyl)-1-(4-fluorophenyl)-2-methyl-isothiourea (0.15 g, 441.47 μmol, 1 eq) and (cyanoamino) sodium (75.00 mg, 1.17 mmol, 2.65 eq) were taken up into a microwave tube in i-PrOH (2 mL). The sealed tube was heated at 80° C. for 20 min under microwave. The mixture was poured to water (10 mL) and extracted with EtOAc (10 mL*2). The combined organic layers were washed with brine (10 mL*2), dried over Na$_2$SO$_4$, filtered and concentrated under reduced pressure to give a residue. The residue was purified by prep-HPLC (neutral condition) to afford compound 1-(4-chloro-3-nitro-phenyl)-2-cyano-3-(4-fluorophenyl)guanidine (0.0058 g, 17.31 μmol, 3.92% yield, 99.58% purity) as a yellow solid. $^1$H NMR: (400 MHz, DMSO-d6) δ 9.71 (br s, 2H), 8.06 (d, J=2.4 Hz, 1H), 7.74-7.69 (m, 1H), 7.68-7.63 (m, 1H), 7.39-7.33 (m, 2H), 7.25-7.17 (m, 2H)

Example 23: Preparation of 1-(4-chloro-3-nitrophenyl)-3-(4-chlorophenyl)urea (Compound 0048)

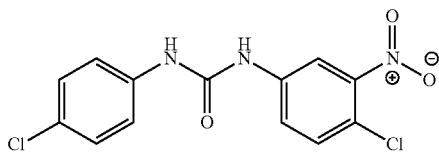 [SMILES: O=C(Nc1ccc(Cl)cc1)Nc1ccc(Cl)c([N+](=O)[O-])c1]

1-chloro-4-isocyanatobenzene (1.0 equiv) and 4-chloro-3-nitroaniline (1.0 equiv) were dissolved in dichloromethane (each 0.5 M) and stirred gently at 25° C. for 48 hours. 1-(4-chloro-3-nitrophenyl)-3-(4-chlorophenyl)urea was collected by filtration, washed with dichloromethane, and dried under vacuum.

Example 23: Preparation of 1-(4-chlorophenyl)-3-(3-nitrophenyl)urea (Compound 0049)

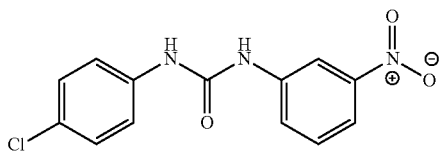 [SMILES: O=C(Nc1ccc(Cl)cc1)Nc1cccc([N+](=O)[O-])c1]

1-chloro-4-isocyanatobenzene (1.0 equiv) and 3-nitroaniline (1.0 equiv) were dissolved in dichloromethane (each 0.5 M) and stirred gently at 25° C. for 48 hours. 1-(4-chlorophenyl)-3-(3-nitrophenyl)urea was collected by filtration, washed with dichloromethane, and dried under vacuum.

Example 24: Preparation of 1-[4-chloro-3-(trifluoromethylsulfonyl)phenyl]-3-(4-fluorophenyl)urea (Compound 0054)

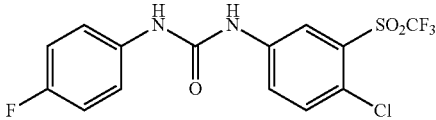

Step 1: Preparation of 2-chloro-5-nitro-benzenediazonium: To a solution of 2-chloro-5-nitro-aniline (6.92 g, 40.10 mmol, 1 eq) in EtOH (12 mL) was added HBF$_4$ (17.61 g, 80.20 mmol, 12.4 mL, 40% purity, 2 eq) and t-BuONO (8.27 g, 80.20 mmol, 9.54 mL, 2 eq) at 0° C. drop-wise slowly. After addition, the mixture was stirred at 25° C. for 2 hours. The mixture was quenched by addition of diisopropyl ether (100 mL) at 20° C., filtered. The filtered cake was washed with diisopropylether (50 mL*3), dried in vacuum afford the crude product 2-chloro-5-nitro-benzenediazonium (7.5 g, crude) as a yellow solid which was used into the next step without further purification.

Step 2: Preparation of 1-chloro-4-nitro-2-(trifluoromethylsulfonyl)benzene: A mixture of 2-chloro-5-nitro-benzenediazonium (3.4 g, 18.42 mmol, 1 eq), sodium trifluoromethanesulfinate (8.62 g, 55.27 mmol, 8.62 mL, 3 eq), Cu$_2$O (263.60 mg, 1.84 mmol, 188.29 uL, 0.1 eq) was degassed and purged with N$_2$ for 3 times, and then DMSO (120 mL) was added by syringe. The mixture was stirred at 25° C. for 12 hr under N$_2$ atmosphere. The mixture was diluted with EtOAc (150 mL) at 20° C., washed with H$_2$O (10 mL*3), brine (10 mL), dried over Na$_2$SO$_4$ and filtered. The filtrate was concentrated under reduced pressure to afford a residue. The residue was purified by flash silica gel chromatography (ISCO®; 40 g SepaFlash® Silica Flash Column, Eluent of 0~50% Ethyl acetate/Petroleum ether gradient@75 mL/min) the compound 1-chloro-4-nitro-2-(trifluoromethylsulfonyl)benzene (0.35 g, 1.21 mmol, 6.56% yield) as light-yellow oil.

Step 3: Preparation of 4-chloro-3-(trifluoromethylsulfonyl)aniline: To a solution of 1-chloro-4-nitro-2-(trifluoromethylsulfonyl)benzene (0.5 g, 1.73 mmol, 1 eq) in EtOH (10 mL)/H$_2$O (2 mL) was added Fe (964.12 mg, 17.26 mmol, 10 eq) and NH$_4$Cl (461.74 mg, 8.63 mmol, 5 eq) under N$_2$ atmosphere. After addition, the mixture was heated to 75° C. and stirred at 75° C. for 6 hours. The mixture was cooled to 25° C. and filtered, and the filter cake was washed with MeOH (10 mL*2). The filtrate was concentrated under reduced pressure to afford a residue. The residue was purified by flash silica gel chromatography (ISCO®; 12 g SepaFlash® Silica Flash Column, Eluent of 0~100% Ethyl acetate/Petroleum ether gradient@36 mL/min) to afford the compound 4-chloro-3-(trifluoromethylsulfonyl)aniline (73.28% purity, 0.34 g) as yellow oil with purity 73.28% on LCMS.

Step 4: Preparation of 1-[4-chloro-3-(trifluoromethylsulfonyl)phenyl]-3-(4-fluorophenyl)urea: To a solution of 4-fluoroaniline (25.68 mg, 231.10 μmol, 22.14 uL, 1.2 eq) in THF (5 mL) was added triphosgene (22.86 mg, 77.03 μmol, 0.4 eq) and DIPEA (49.78 mg, 385.16 μmol, 67.09 uL, 2 eq) at 0° C. After addition, the mixture was stirred at 0° C. for 2 hours and then 4-chloro-3-(trifluoromethylsulfonyl)aniline (0.05 g, 192.58 μmol, 1 eq) was added. The mixture was warmed to 25° C. and stirred for 10 hours. The mixture was quenched by addition of H$_2$O (10 mL) at 0° C., extracted with EtOAc (10 mL*2). The combined organic layers were washed with H₂O (10 mL), dried over Na₂SO₄ and filtered. The filtrate was concentrated under reduced pressure to afford a residue. The residue was purified by pre-HPLC (column: HUAPU C8 Extreme BDS 150*30 5 u; mobile phase: [water(0.04% HCl)-ACN]; B %: 40%-75%, 11 min) to afford the compound 1-[4-chloro-3-(trifluoromethylsulfonyl)phenyl]-3-(4-fluorophenyl)urea (0.0162 g, 40.48 μmol, 21.02% yield, 99.13% purity) as an off-white solid with purity 99.13% on LCMS. ¹H NMR: (400 MHz, MeOD) δ 8.53 (s, 1H), 7.97 (m, 1H), 7.74 (m, 1H), 7.51 (m, 2H), 7.11 (m, 2H).

Example 25: Preparation of 1-(p-tolyl)-3-(3-(trifluoromethyl)phenyl)urea (Compound 0058)

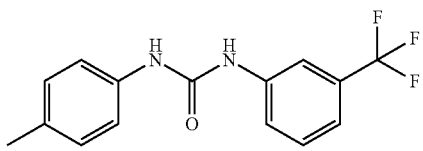 [SMILES: Cc1ccc(NC(=O)Nc2cccc(C(F)(F)F)c2)cc1]

1-isocyanato-4-methylbenzene (1.0 equiv) and 3-(trifluoromethyl)aniline (1.0 equiv) were dissolved in dichloromethane (each 0.5 M) and stirred gently at 25° C. for 48 hours. 1-(p-tolyl)-3-(3-(trifluoromethyl)phenyl)urea was collected by filtration, washed with dichloromethane, and dried under vacuum.

Example 26: Preparation of 1-(3-chlorophenyl)-3-(4-fluorophenyl)urea (Compound 0060)

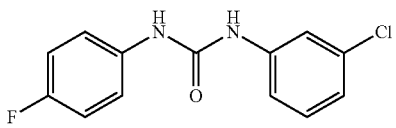 [SMILES: O=C(Nc1ccc(F)cc1)Nc1cccc(Cl)c1]

1-fluoro-4-isocyanatobenzene (1.0 equiv) and 3-chloroaniline (1.0 equiv) were dissolved in dichloromethane (each 0.5 M) and stirred gently at 25° C. for 48 hours. 1-(3-chlorophenyl)-3-(4-fluorophenyl)urea was collected by filtration, washed with dichloromethane, and dried under vacuum.

Example 27: Preparation of 1-(4-chloro-3-nitrophenyl)-3-(3-chlorophenyl)urea (Compound 0061)

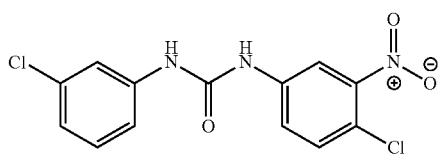 [SMILES: O=C(Nc1cccc(Cl)c1)Nc1ccc(Cl)c([N+](=O)[O-])c1]

1-chloro-3-isocyanatobenzene (1.0 equiv) and 4-chloro-3-nitroaniline (1.0 equiv) were dissolved in dichloromethane (each 0.5 M) and stirred gently at 25° C. for 48 hours. 1-(4-chloro-3-nitrophenyl)-3-(3-chlorophenyl)urea was collected by filtration, washed with dichloromethane, and dried under vacuum.

Example 28: Preparation of 1-(3-chlorophenyl)-3-(m-tolyl)urea (Compound 0063)

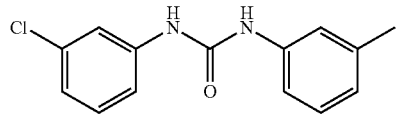 [SMILES: Cc1cccc(NC(=O)Nc2cccc(Cl)c2)c1]

1-chloro-3-isocyanatobenzene (1.0 equiv) and w-toluidine (1.0 equiv) were dissolved in dichloromethane (each 0.5 M) and stirred gently at 25° C. for 48 hours. 1-(3-chlorophenyl)-3-(m-tolyl)urea was collected by filtration, washed with dichloromethane, and dried under vacuum.

Example 29: Preparation of 3-[4-chloro-3-(trifluoromethyl)anilino]-4-(4-fluoroanilino)cyclobut-3-ene-1,2-dione (Compound 0064)

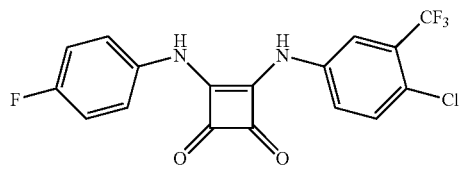

Step 1: Preparation of 3-ethoxy-4-(4-fluoroanilino)cyclobut-3-ene-1,2-dione: To a solution of 4-fluoroaniline (0.2 g, 1.80 mmol, 172.41 uL, 1 eq) in EtOH (20 mL) was added 3,4-diethoxycyclobut-3-ene-1,2-dione (306.28 mg, 1.80 mmol, 264.03 uL, 1 eq). The mixture was stirred at 25° C. for 12 hours. The mixture was concentrated directly under reduced pressure to afford the crude product 3-ethoxy-4-(4-fluoroanilino)cyclobut-3-ene-1,2-dione (0.42 g, crude) as a light-yellow solid which was used into the next step without further purification.

Step 2: Preparation of 3-[4-chloro-3-(trifluoromethyl)anilino]-4-(4-fluoroanilino)cyclobut-3-ene-1,2-dione: To a solution of 3-ethoxy-4-(4-fluoroanilino)cyclobut-3-ene-1,2-dione (0.2 g, 850.30 μmol, 1 eq) in THF (5 mL) was added AlMe₃ (2 M, 425.15 uL, 1 eq) and 4-chloro-3-(trifluoromethyl)aniline (166.29 mg, 850.30 μmol, 1 eq) at 20° C. After addition, the mixture was heated to 65° C. and stirred at 65° C. for 12 hours. The mixture was quenched by addition of H₂O (15 mL) at 0° C., extracted with EtOAc (20 mL*2). The combined organic layers were washed with H₂O (20 mL), brine (20 mL), dried over Na₂SO₄ and filtered. The filtrate was concentrated under reduced pressure to afford a residue. The residue was re-crystallized in MDF/H₂O (2 mL/4 mL) and MeOH (5 mL) to afford the compound 3-[4-chloro-3-(trifluoromethyl)anilino]-4-(4-fluoroanilino)cyclobut-3-ene-1,2-dione (0.0605 g, 154.56 μmol, 18.18% yield, 98.28% purity) as a white solid with purity 98.28% on LCMS. ¹H NMR: (400 MHz, DMSO-d6) δ 9.96-10.89 (brs, 2H), 7.93 (s, 1H), 7.0-7.62 (m, 1H), 7.57 (m, 1H), 7.36-7.39 (m, 2H), 7.14-7.18 (m, 2H).

Example 30: Preparation of 1-(3-chlorophenyl)-3-(4-chlorophenyl)urea (Compound 0066)

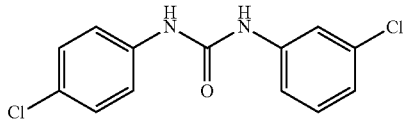 [SMILES: O=C(Nc1ccc(Cl)cc1)Nc1cccc(Cl)c1]

1-chloro-4-isocyanatobenzene (1.0 equiv) and 3-chloroaniline (1.0 equiv) were dissolved in dichloromethane (each 0.5 M) and stirred gently at 25° C. for 48 hours. 1-(3-chlorophenyl)-3-(4-chlorophenyl)urea was collected by filtration, washed with dichloromethane, and dried under vacuum.

Example 31: Preparation of 1-(3-nitrophenyl)-3-(m-tolyl)urea (Compound 0067)

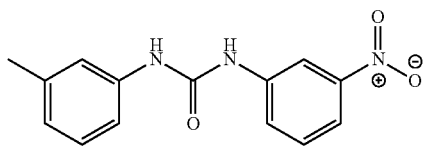 [SMILES: Cc1cccc(NC(=O)Nc2cccc([N+](=O)[O-])c2)c1]

1-isocyanato-3-methylbenzene (1.0 equiv) and 3-nitroaniline (1.0 equiv) were dissolved in dichloromethane (each 0.5 M) and stirred gently at 25° C. for 48 hours. 1-(3-nitrophenyl)-3-(m-tolyl)urea was collected by filtration, washed with dichloromethane, and dried under vacuum.

Example 32: Preparation of 1-(3-chlorophenyl)-3-(p-tolyl)urea (Compound 0068)

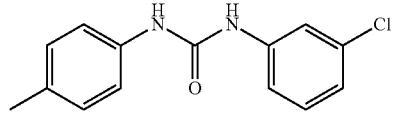 [SMILES: Cc1ccc(NC(=O)Nc2cccc(Cl)c2)cc1]

1-isocyanato-4-methylbenzene (1.0 equiv) and 3-chloroaniline (1.0 equiv) were dissolved in dichloromethane (each 0.5 M) and stirred gently at 25° C. for 48 hours. 1-(3-chlorophenyl)-3-(p-tolyl)urea was collected by filtration, washed with dichloromethane, and dried under vacuum.

Example 33: Preparation of 1-(4-bromo-3-(trifluoromethyl)phenyl)-3-(p-tolyl)urea (Compound 0075)

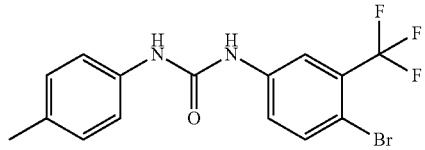 [SMILES: Cc1ccc(NC(=O)Nc2ccc(Br)c(C(F)(F)F)c2)cc1]

1-isocyanato-4-methylbenzene (1.0 equiv) and 4-bromo-3-(trifluoromethyl)aniline (1.0 equiv) were dissolved in dichloromethane (each 0.5 M) and stirred gently at 25° C. for 48 hours. 1-(4-bromo-3-(trifluoromethyl)phenyl)-3-(p-tolyl)urea was collected by filtration, washed with dichloromethane, and dried under vacuum.

Example 34: Preparation of 1-(4-fluorophenyl)-3-(3-nitrophenyl)urea (Compound 0076)

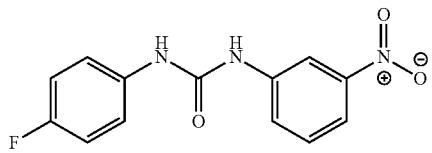 [SMILES: O=C(Nc1ccc(F)cc1)Nc1cccc([N+](=O)[O-])c1]

1-fluoro-4-isocyanatobenzene (1.0 equiv) and 3-nitroaniline (1.0 equiv) were dissolved in dichloromethane (each 0.5 M) and stirred gently at 25° C. for 48 hours. 1-(4-fluorophenyl)-3-(3-nitrophenyl)urea was collected by filtration, washed with dichloromethane, and dried under vacuum.

Example 35: Preparation of 1-(3-chlorophenyl)-3-(3-nitrophenyl)urea (Compound 0078)

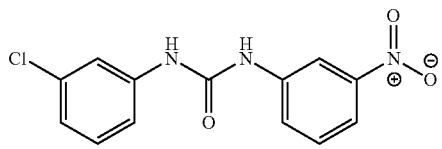 [SMILES: O=C(Nc1cccc(Cl)c1)Nc1cccc([N+](=O)[O-])c1]

1-chloro-3-isocyanatobenzene (1.0 equiv) and 3-nitroaniline (1.0 equiv) were dissolved in dichloromethane (each 0.5 M) and stirred gently at 25° C. for 48 hours. 1-(3-chlorophenyl)-3-(3-nitrophenyl)urea was collected by filtration, washed with dichloromethane, and dried under vacuum.

Example 36: Preparation of 1-(4-chloro-3-nitrophenyl)-3-[4-fluoro-2-[3-(trifluoromethyl)diazirin-3-yl]phenyl]urea (Compound 0079)

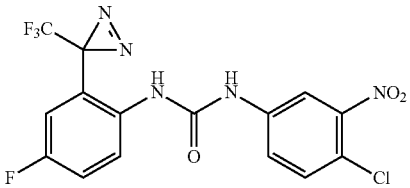 [SMILES: O=C(Nc1ccc(Cl)c([N+](=O)[O-])c1)Nc1ccc(F)cc1C1(C(F)(F)F)N=N1]

Step 1: Preparation of 4-fluoro-2-iodo-aniline: To a solution of 4-fluoroaniline (5 g, 45.00 mmol, 4.31 mL, 1 eq) in $H_2O$ (40 mL) was added $I_2$ (13.70 g, 54.00 mmol, 10.88 mL, 1.2 eq) and $NaHCO_3$ (11.34 g, 134.99 mmol, 5.25 mL, 3 eq). The mixture was stirred at 15° C. for 4 hours. The mixture was quenched by addition of $H_2O$ (50 mL) at 0° C., extracted with EtOAc (40 mL*2). The combined organic layers were washed with saturated aqueous $NaSO_3$ (60 mL*2), brine (60 mL), dried over $Na_2SO_4$ and filtered. The filtrate was concentrated under reduced pressure to afford a residue. The residue was purified by flash silica gel chromatography (ISCO®; 80 g SepaFlash® Silica Flash Column, Eluent of 0~50% Ethyl acetate/Petroleum ether gradient@100 mL/min) to afford the compound 4-fluoro-2-iodo-aniline (10 g, 42.19 mmol, 93.76% yield) as red oil. $^1$H NMR: (DMSO-d6, 400 MHz) δ 7.39-7.42 (m, 1H), 6.94-6.99 (m, 1H), 6.72-6.75 (m, 1H), 5.06 (brs, 2H).

Step 2: Preparation of tert-butyl N-(4-fluoro-2-iodo-phenyl)carbamate: To a solution of 4-fluoro-2-iodo-aniline (9 g, 37.97 mmol, 1 eq) in THF (90 mL) was added NaHMDS (1 M, 75.95 mL, 2 eq) and (Boc)$_2$O (9.12 g, 41.77 mmol, 9.60 mL, 1.1 eq) at 0° C. After addition, the mixture was stirred at 25° C. for 12 hours. The mixture was quenched by addition of saturated aqueous NH$_4$Cl (150 mL) at 0° C., extracted with EtOAc (100 mL*2). The combined organic layers were washed with H$_2$O (150 mL), brine (150 mL), dried over Na$_2$SO$_4$ and filtered. The filtrate was concentrated under reduced pressure to afford a residue. The residue was purified by flash silica gel chromatography (ISCO®; 120 g SepaFlash® Silica Flash Column, Eluent of 0~50% Ethyl acetate/Petroleum ether gradient@100 mL/min) to afford the compound tert-butyl N-(4-fluoro-2-iodo-phenyl)carbamate (9.1 g, 26.99 mmol, 71.08% yield) as a dark yellow solid.

Step 3: Preparation of tert-butyl N-[4-fluoro-2-(2,2,2-trifluoroacetyl)phenyl]carbamate: To a solution of tert-butyl N-(4-fluoro-2-iodo-phenyl)carbamate (9.7 g, 28.77 mmol, 1 eq) in THF (200 mL) was added i-PrMgCl—LiCl (1.3 M, 77.46 mL, 3.5 eq) at −70° C. The mixture was stirred for 0.5 hr and then 2,2,2-trifluoro-N-methoxy-N-methyl-acetamide (9.94 g, 63.30 mmol, 7.65 mL, 2.2 eq) was added drop-wise slowly. The mixture was stirred at −70° C. for 0.5 hr and warmed to 25° C. for 2 hours. The mixture was quenched by addition of saturated aq NH$_4$Cl (200 mL) at 0° C., extracted with EtOAc (150 mL*2). The combined organic layers were washed with H$_2$O (250 mL), brine (250 mL), dried over Na$_2$SO$_4$ and filtered. The filtrate was concentrated under reduced pressure to afford the crude product tert-butyl N-[4-fluoro-2-(2,2,2-trifluoroacetyl)phenyl]carbamate (8.8 g, crude) as dark yellow oil which was used into the next step without further purification.

Step 4: Preparation of tert-butyl N-[4-fluoro-2-[(Z)—N-hydroxy-C-(trifluoromethyl)carbonimidoyl]phenyl]carbamate: To a solution of tert-butyl N-[4-fluoro-2-(2,2,2-trifluoroacetyl)phenyl]carbamate (8.8 g, 28.64 mmol, 1 eq) in Pyridine (80 mL) was added NH$_2$OH·HCl (3.98 g, 57.28 mmol, 2 eq). The mixture was stirred at 100° C. for 12 hours. The mixture was concentrated under reduced pressure to afford the crude product tert-butyl N-[4-fluoro-2-[(Z)—N-hydroxy-C-(trifluoromethyl)carbonimidoyl]phenyl]carbamate (9.3 g, crude) as a yellow solid which was used into the next step without further purification.

Step 5: Preparation of [(Z)-[1-[2-(tert-butoxycarbonylamino)-5-fluoro-phenyl]-2,2,2-trifluoro-ethylidene]amino]4-methylbenzenesulfonate: To a solution of tert-butyl N-[4-fluoro-2-[(Z)—N-hydroxy-C-(trifluoromethyl)carbonimidoyl]phenyl]carbamate (9.3 g, 28.86 mmol, 1 eq) in ACETONE (90 mL) was added TEA (8.76 g, 86.58 mmol, 12.05 mL, 3 eq) and 4-methylbenzenesulfonyl chloride (5.50 g, 28.86 mmol, 1 eq). The mixture turned from a yellow solution to a red solution. The mixture was stirred at 20° C. for 3 hours. The mixture was quenched by addition of H$_2$O (100 mL) at 0° C., and then concentrated under reduced pressure to remove the organic solvent. The residue was diluted with EtOAc (200 mL). The organic layers were washed with H$_2$O (200 mL), brine (200 mL), dried over Na$_2$SO$_4$ and filtered. The filtrate was concentrated under reduced pressure to afford a residue. The residue was purified by flash silica gel chromatography (ISCO®; 220 g SepaFlash® Silica Flash Column, Eluent of 0~50% Ethyl acetate/Petroleum ether gradient@150 mL/min) to afford the compound [(Z)-[1-[2-(tert-butoxycarbonylamino)-5-fluoro-phenyl]-2,2,2-trifluoro-ethylidene]amino]4-methylbenzenesulfonate (4.7 g, 9.86 mmol, 34.18% yield) as a yellow solid. $^1$H NMR: (CDCl$_3$, 400 MHz) δ 7.89 (d, J=8.0 Hz, 2H), 7.75 (m, 1H), 7.41 (d, J=8.0 Hz, 2H), 7.20-7.23 (m, 1H), 6.83-6.85 (m, 1H), 6.08 (brs, 1H), 2.49 (s, 3H), 1.49 (s, 9H).

Step 6: Preparation of tert-butyl N-[4-fluoro-2-[3-(trifluoromethyl)diazirin-3-yl]phenyl]carbamate: To a solution of [(Z)-[1-[2-(tert-butoxycarbonylamino)-5-fluoro-phenyl]-2,2,2-trifluoro-ethylidene]amino] 4-methylbenzenesulfonate (1.5 g, 3.15 mmol, 1 eq) in Et$_2$O (10 mL) was bubbled NH$_3$ (30 mL) at −30° C. for 1 h. The reaction mixture was charged into an autoclave and heated to 50° C. and stirred at 1.5 Mpa for 12 hours. The mixture was cooled to −40° C. and diluted with Et$_2$O (40 mL). The combined organic layers were washed with H$_2$O (40 mL), brine (40 mL), dried over Na$_2$SO$_4$ and filtered. The filtrate was concentrated under reduced pressure at 0° C. to afford a residue. The residue was purified by flash silica gel chromatography (ISCO®; 12 g SepaFlash® Silica Flash Column, Eluent of 0~100% DCM/Petroleum ether gradient@36 mL/min) to afford the compound tert-butyl N-[4-fluoro-2-[3-(trifluoromethyl)diazirin-3-yl]phenyl]carbamate (0.5 g, 1.57 mmol, 49.75% yield) as yellow oil. $^1$H NMR: (DMSO-d6, 400 MHz) δ 9.17 (brs, 1H), 7.56-7.58 (m, 1H), 7.38 (m, 1H), 7.24-7.27 (m, 1H), 1.49 (s, 9H).

Step 7: Preparation of 4-fluoro-2-[3-(trifluoromethyl)diazirin-3-yl]aniline: To a solution of tert-butyl N-[4-fluoro-2-[3-(trifluoromethyl)diazirin-3-yl]phenyl]carbamate (0.45 g, 1.41 mmol, 1 eq) in EtOAc (1 mL) was added HCl/EtOAc (4 M, 5 mL, 14.19 eq) dropwise slowly. The mixture was stirred at 20° C. for 2 hours, a yellow precipitate was formed. The mixture was concentrated directly under reduced pressure to afford the crude compound 4-fluoro-2-[3-(trifluoromethyl)diazirin-3-yl]aniline (0.17 g, 665.10 μmol, 47.19% yield, HCl) as a light-yellow solid which was used directly into next step, $^1$H NMR: (DMSO-d6, 400 MHz) δ 7.31-7.33 (m, 1H), 7.12-7.15 (m, 1H), 6.81-6.85 (m, 1H), 5.34-5.50 (brs, 3H).

Step 8: Preparation of 1-(4-chloro-3-nitro-phenyl)-3-[4-fluoro-2-[3-(trifluoromethyl)diazirin-3-yl]phenyl]urea: To a solution of 4-fluoro-2-[3-(trifluoromethyl)diazirin-3-yl]aniline (0.055 g, 215.18 μmol, 1 eq, HCl) in THF (3 mL) was added triphosgene (25.54 mg, 86.07 μmol, 0.4 eq) and TEA (87.10 mg, 860.72 μmol, 119.80 uL, 4 eq) at 0° C. The mixture was stirred at 0° C. for 1 hr and then 4-chloro-3-nitro-aniline (37.13 mg, 215.18 μmol, 1 eq) was added. The mixture was warned to 20° C. and stirred for another 2 hours. The mixture was quenched by addition of H$_2$O (5 mL) at 0° C., extracted with EtOAc (10 mL*2). The combined organic layers were washed with H$_2$O (10 mL), brine (10 mL), dried over Na$_2$SO$_4$ and filtered. The filtrate was concentrated under reduced pressure to afford a residue. The residue was purified by prep-HPLC (neutral condition; column: Xamide 150*30 mm 5 um; mobile phase: [water (10 mM NH$_4$HCO$_3$)-ACN]; B %: 60%-80%, 10 min) to afford the compound 1-(4-chloro-3-nitro-phenyl)-3-[4-fluoro-2-[3-(trifluoromethyl)diazirin-3-yl]phenyl]urea (0.012 g, 24.1 μmol, 11.2% yield) as a light-yellow solid. $^1$H NMR: (DMSO-d6, 400 MHz) δ 9.79 (s, 1H), 8.70 (s, 1H), 8.31 (s, 1H), 7.70-7.71 (m, 2H), 7.62-7.68 (m, 2H), 7.44 (m, 1H).

Example 37: Preparation of N3-(4-chloro-3-nitro-phenyl)-N4-(4-fluorophenyl)-1,1-dioxo-1,2,5-thiadiazole-3,4-diamine (Compound 0080)

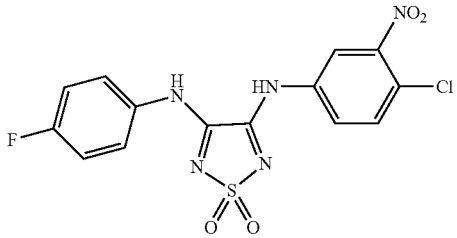 [SMILES: O=[N+]([O-])c1cc(NC2=NS(=O)(=O)N=C2Nc2ccc(F)cc2)ccc1Cl]

To a solution of 3,4-diethoxy-1,2,5-thiadiazole 1,1-dioxide (0.035 g, 169.72 μmol, 1 eq), 4-chloro-3-nitro-aniline (29.29 mg, 169.72 μmol, 1 eq) and 4-fluoroaniline (33.95 mg, 305.50 μmol, 29.26 uL, 1.8 eq) in toluene (2 mL) was added AlMe$_3$ (2 M, 424.31 uL, 5 eq) at 25° C. The mixture was taken up into a microwave tube. The sealed tube was heated at 120° C. for 2 hours under microwave. The mixture was quenched by addition of aq HCl (2M, 5 mL) at 25° C., extracted with EtOAc (10 mL*2). The combined organic layers were washed with H$_2$O (10 mL), brine (10 mL), dried over Na$_2$SO$_4$ and filtered. The filtrate was concentrated under reduced pressure to afford a residue. The residue was purified by prep-HPLC (TFA condition; column: Waters Xbridge Prep OBD C18 150*30 5 u; mobile phase: [water (0.1% TFA)-ACN]; B %: 40%-70%, 13 min) to afford the compound N3-(4-chloro-3-nitro-phenyl)-N4-(4-fluorophenyl)-1,1-dioxo-1,2,5-thiadiazole-3,4-diamine (0.0064 g, 15.60 μmol, 9.19% yield, 96.98% purity) as a white solid with purity 96.98% on LCMS. $^1$H NMR: (400 MHz, MeOD) δ 8.50 (d, J=2.4 Hz, 1H), 8.02 (d, J=8.8 Hz, 1H), 7.82-7.85 (m, 2H), 7.78 (d, J=8.8 Hz, 1H), 7.21-7.25 (m, 2H).

Example 38: Preparation of 1-(4-chloro-3-cyano-phenyl)-3-(4-fluorophenyl) urea (Compound 0083)

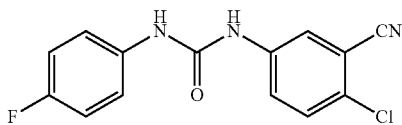

To a mixture of 5-amino-2-chloro-benzonitrile (0.2 g, 1.31 mmol, 1 eq) in THF (5 mL) was added triphosgene (136.14 mg, 458.77 μmol, 0.35 eq) and TEA (397.91 mg, 3.93 mmol, 547.34 uL, 3 eq) at 0° C. Then the mixture was stirred at 0° C. for 30 min. Then 4-fluoroaniline (145.65 mg, 1.31 mmol, 125.56 uL, 1 eq) was added to the mixture. The mixture was stirred at 25° C. for 2 hours. The mixture was poured to water (10 mL) and extracted with EtOAc (10 mL*2). The combined organic layers were washed with brine (10 mL*2), dried over Na$_2$SO$_4$, filtered and concentrated under reduced pressure to give a residue. The residue was purified by prep-HPLC (neutral condition) to afford compound 1-(4-chloro-3-cyano-phenyl)-3-(4-fluorophenyl) urea (57.0 mg, 196.76 μmol, 15.01% yield, 100% purity) as a white solid. $^1$H NMR: (400 MHz, MeOD) δ 8.01 (d, J=2.6 Hz, 1H), 7.64 (dd, J=2.7, 8.9 Hz, 1H), 7.52 (d, J=8.9 Hz, 1H), 7.47-7.40 (m, 2H), 7.09-7.01 (m, 2H).

Example 39: Preparation of 1-(6-chloro-3-pyridyl)-3-(4-fluorophenyl) urea (Compound 0090)

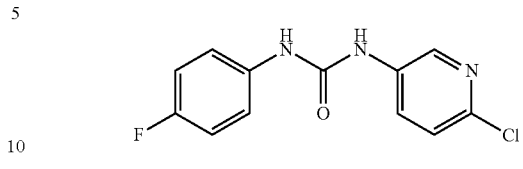

To a mixture of 6-chloropyridin-3-amine (0.2 g, 1.56 mmol, 1 eq) in THF (5 mL) was added triphosgene (161.58 mg, 544.49 μmol, 0.35 eq) and TEA (472.26 mg, 4.67 mmol, 649.60 uL, 3 eq) at 0° C. Then the mixture was stirred at 0° C. for 30 min. Then 4-fluoroaniline (172.86 mg, 1.56 mmol, 149.02 uL, 1 eq) was added to the mixture. The mixture was stirred at 25° C. for 2 hours. The mixture was poured to water (10 mL) and extracted with EtOAc (10 mL*2). The combined organic layers were washed with brine (10 mL*2), dried over Na$_2$SO$_4$, filtered and concentrated under reduced pressure to give a residue. The residue was purified by prep-HPLC (neutral condition) to afford the compound 1-(6-chloro-3-pyridyl)-3-(4-fluorophenyl) urea (82.6 mg, 305.94 μmol, 19.67% yield, 98.4% purity) as a white solid. $^1$H NMR: (400 MHz, MeOD) δ 8.44 (d, J=2.7 Hz, 1H), 8.00 (dd, J=2.8, 8.7 Hz, 1H), 7.47-7.35 (m, 3H), 7.10-7.02 (m, 1H), 7.09-7.00 (m, 1H).

Example 40: Preparation of 1-(3-chlorophenyl)-3-phenyl urea (Compound 0091)

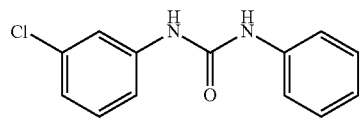 [SMILES: O=C(Nc1ccccc1)Nc1cccc(Cl)c1]

1-chloro-3-isocyanatobenzene (1.0 equiv) and aniline (1.0 equiv) were dissolved in dichloromethane (each 0.5 M) and stirred gently at 25° C. for 48 hours. 1-(3-chlorophenyl)-3-phenylurea was collected by filtration, washed with dichloromethane, and dried under vacuum.

Example 41: Preparation of 3-[4-chloro-3-(trifluoromethyl)anilino]-4-(3,4-difluoroanilino)cyclobut-3-ene-1,2-dione (Compound 0092)

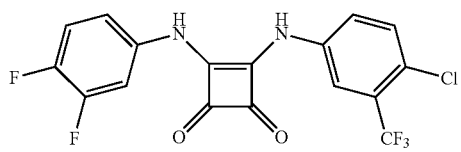 [SMILES: O=c1c(Nc2ccc(F)c(F)c2)c(Nc2ccc(Cl)c(C(F)(F)F)c2)c1=O]

Step 1: Preparation of 3-[4-chloro-3-(trifluoromethyl)anilino]-4-ethoxy-cyclobut-3-ene-1,2-dione: To a solution of 4-chloro-3-(trifluoromethyl)aniline (0.22 g, 1.12 mmol, 1 eq) in EtOH (4 mL) was added 3,4-diethoxycyclobut-3-ene-1,2-dione (191.42 mg, 1.12 mmol, 165.02 uL, 1 eq). The mixture was stirred at 70° C. for 12 hours. The mixture was concentrated directly under reduced pressure to afford a residue. The residue was triturated with MTBE (5 mL) and filtered to afford the crude product 3-[4-chloro-3-(trifluoromethyl)anilino]-4-ethoxy-cyclobut-3-ene-1,2-dione (0.15 g, crude) as a yellow solid which was used into the next step without further purification.

Step 2: Preparation of 3-[4-chloro-3-(trifluoromethyl)anilino]-4-(3,4-difluoroanilino)cyclobut-3-ene-1,2-dione: To a solution of 3,4-difluoroaniline (66.64 mg, 516.17 µmol, 1.1 eq) in THF (2 mL) was added 3-[4-chloro-3-(trifluoromethyl)anilino]-4-ethoxy-cyclobut-3-ene-1,2-dione (0.15 g, 469.24 µmol, 1 eq) and AlMe$_3$ (1 M, 1.41 mL, 3 eq) at 25° C. After addition, the mixture was heated to 70° C. and stirred at 70° C. for 12 hours. The mixture was quenched by addition of H$_2$O (5 mL) at 0° C., extracted with EtOAc (10 mL*2). The combined organic layers were washed with H$_2$O (5 mL), dried over Na$_2$SO$_4$ and filtered. The filtrate was concentrated under reduced pressure to afford a residue. The residue was purified by prep-HPLC (FA condition, column: Luna C18 100*30 5 u; mobile phase: [water(0.225% FA)-ACN]; B %: 40%-80%, 15 min to afford the compound 3-[4-chloro-3-(trifluoromethyl)anilino]-4-(3,4-difluoroanilino)cyclobut-3-ene-1,2-dione (0.025 g, 54.94 µmol, 11.71% yield, 98.61% purity, FA) as a light-yellow solid. $^1$H NMR: (DMSO-d6, 400 MHz) δ 10.12-10.18 (brs, 3H), 7.95 (s, 1H), 7.66-7.69 (m, 1H), 7.58-7.60 (m, 2H), 7.38-7.43 (m, 1H), 7.11-7.13 (m, 1H).

Example 42: Preparation of 1-(4-chloro-3-nitrophenyl)-3-[4-fluoro-3-[3-(trifluoromethyl)diazirin-3-yl]phenyl]urea (Compound 0094)

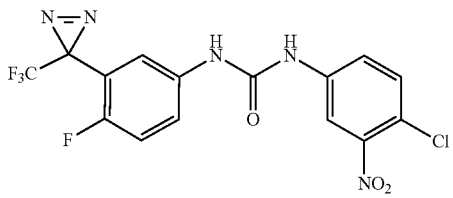 [SMILES: O=C(Nc1ccc(Cl)c([N+](=O)[O-])c1)Nc1ccc(F)c(C2(C(F)(F)F)N=N2)c1]

Step 1: Preparation of 1-(5-bromo-2-fluoro-phenyl)-2,2,2-trifluoro-ethanone: To a solution of LDA (2 M, 21.43 mL, 1.50 eq) in THF (5 mL) was added 1-bromo-4-fluorobenzene (5 g, 28.57 mmol, 3.14 mL, 1 eq) in THF (5 mL) at −70° C. The mixture was stirred at −70° C. for 0.5 hr and then ethyl 2,2,2-trifluoroacetate (8.12 g, 57.14 mmol, 7.88 mL, 2 eq) in THF (5 mL) was added drop-wise. The mixture was stirred at −70° C. for 0.5 hr and warmed to 0° C. and stirred for 2 hours. The mixture was quenched by addition of saturated aqueous NH$_4$Cl (50 mL) at 0° C., extracted with EtOAc (40 mL*2). The combined organic layers were washed with H$_2$O (50 mL), brine (50 mL), dried over Na$_2$SO$_4$ and filtered. The filtrate was concentrated under reduced pressure to afford a residue. The residue was purified by flash silica gel chromatography (ISCO®; 80 g SepaFlash® Silica Flash Column, Eluent of 0~100% Ethyl acetate/Petroleum ether gradient@100 mL/min) to afford the product 1-(5-bromo-2-fluoro-phenyl)-2,2,2-trifluoro-ethanone (3 g, 6.03 mmol, 21.10% yield, 54.45% purity) as yellow oil which has no mass response on LCMS.

Step 2: Preparation of 1-(5-bromo-2-fluoro-phenyl)-2,2,2-trifluoro-ethanone oxime: To a solution of 1-(5-bromo-2-fluoro-phenyl)-2,2,2-trifluoro-ethanone (3 g, 11.07 mmol, 1 eq) in Pyridine (20 mL) was added NH$_2$OH·HCl (1.54 g, 22.14 mmol, 2 eq). The mixture was stirred at 100° C. for 5 hours. The mixture was concentrated directly under reduced pressure to afford a residue. The residue was diluted with EtOAc (100 mL), washed with aqueous HCl (1 N, 50 mL*2), washed with H$_2$O (60 mL), dried over Na$_2$SO$_4$ and filtered. The filtrate was concentrated under reduced pressure to afford the crude product 1-(5-bromo-2-fluoro-phenyl)-2,2,2-trifluoro-ethanone oxime (3.1 g, crude) as yellow oil which was used into the next step without further purification.

Step 3: Preparation of [(Z)-[1-(5-bromo-2-fluoro-phenyl)-2,2,2-trifluoro-ethylidene]amino] 4-methylbenzenesulfonate: To a solution of 1-(5-bromo-2-fluoro-phenyl)-2,2,2-trifluoro-ethanone oxime (3 g, 10.49 mmol, 1 eq) in Acetone (25 mL) was added TEA (3.18 g, 31.47 mmol, 4.38 mL, 3 eq) and TosCl (2.40 g, 12.59 mmol, 1.2 eq). The mixture was stirred at 25° C. for 2 hours. The reaction mixture was concentrated under reduced pressure to give a residue. The residue was purified by flash silica gel chromatography (ISCO®; 80 g SepaFlash® Silica Flash Column, Eluent of 0~50% Ethyl acetate/Petroleum ether gradient@100 mL/min) to afford the compound [(Z)-[1-(5-bromo-2-fluoro-phenyl)-2,2,2-trifluoro-ethylidene]amino] 4-methylbenzenesulfonate (3.6 g, 8.18 mmol, 77.97% yield) as a light-yellow solid. $^1$H NMR: (CDCl$_3$, 400 MHz) δ 7.79-7.82 (m, 2H), 7.60 (m, 1H), 7.27-7.33 (m, 3H), 6.97-7.05 (m, 1H), 2.41 (s, 3H).

Step 4: Preparation of 3-(5-bromo-2-fluoro-phenyl)-3-(trifluoromethyl)diazirine: To a solution of [(Z)-[1-(5-bromo-2-fluoro-phenyl)-2,2,2-trifluoro-ethylidene]amino] 4-methylbenzenesulfonate (2.6 g, 5.91 mmol, 1 eq) in Et$_2$O (20 mL) was added bubble NH$_3$ (80 mL) at −40° C. for 1 h. The reaction mixture was charged into an autoclave and heated to 50° C. and stirred at 1.2 Mpa for 12 hours. The mixture was cooled to −40° C. and diluted with Et$_2$O (80 mL). The combined organic layers were washed with H$_2$O (60 mL), brine (60 mL), dried over Na$_2$SO$_4$ and filtered. The filtrate was concentrated under reduced pressure at 0° C. to afford the crude product 3-(5-bromo-2-fluoro-phenyl)-3-(trifluoromethyl)diazirine (1.8 g, crude) as yellow oil which was used into the next step without further purification.

Step 5: Preparation of tert-butyl N-[4-fluoro-3-[3-(trifluoromethyl)diazirin-3-yl]phenyl]carbamate: A mixture of 3-(5-bromo-2-fluoro-phenyl)-3-(trifluoromethyl)diazirine (0.75 g, 2.65 mmol, 1 eq), NH$_2$Boc (620.87 mg, 5.30 mmol, 2 eq), Pd(OAc)$_2$ (118.99 mg, 530.00 µmol, 0.2 eq), dicyclohexyl-[2-(2,4,6-triisopropylphenyl)phenyl]phosphane (378.99 mg, 795.00 µmol, 0.3 eq) and NaOBu-t (636.68 mg, 6.62 mmol, 2.5 eq) in toluene (10 mL) was degassed and purged with N$_2$ for 3 times, and then the mixture was heated at 70° C. for 6 hours under N$_2$ protection. The mixture was diluted with EtOAc (20 mL) at 20° C., and filtered. The filtrate was washed with H$_2$O (15 mL), brine (15 mL), dried over Na$_2$SO$_4$ and filtered. The filtrate was concentrated under reduced pressure to afford a residue. The residue was purified by flash silica gel chromatography (ISCO®; 20 g SepaFlash® Silica Flash Column, Eluent of 0~50% Ethyl acetate/Petroleum ether gradient@50 mL/min) and then further purified by prep-TLC (SiO$_2$, Petroleum ether: Ethyl acetate=5:1) to afford the compound tert-butyl N-[4-fluoro-3-[3-(trifluoromethyl)diazirin-3-yl]phenyl]carbamate (0.27 g, 624.65 µmol, 11.79% yield, 73.86% purity) as a yellow solid.

Step 6: Preparation of 4-fluoro-3-[3-(trifluoromethyl)diazirin-3-yl]aniline: To a solution of tert-butyl N-[4-fluoro-3-[3-(trifluoromethyl)diazirin-3-yl]phenyl]carbamate (0.27 g, 845.72 µmol, 1 eq) in EtOAc (1 mL) was added HCl/EtOAc (4 M, 5 mL, 23.65 eq) drop-wise slowly. The mixture was stirred at 20° C. for 2 hours. The mixture was concentrated directly under reduced pressure to afford the crude product 4-fluoro-3-[3-(trifluoromethyl)diazirin-3-yl]aniline (0.21 g, crude, HCl) as a yellow solid which was used into the next step without further purification.

Step 7: Preparation of 1-(4-chloro-3-nitro-phenyl)-3-[4-fluoro-3-[3-(trifluoromethyl)diazirin-3-yl]phenyl]urea: To a solution of 4-fluoro-3-[3-(trifluoromethyl)diazirin-3-yl]aniline (0.055 g, 215.18 μmol, 1 eq, HCl) in THF (3 mL) was added triphosgene (22.35 mg, 75.31 μmol, 0.35 eq) and TEA (87.10 mg, 860.72 μmol, 119.80 uL, 4 eq) at 0° C. The mixture was stirred at 0° C. for 1 hour and then 4-chloro-3-nitro-aniline (33.42 mg, 193.66 μmol, 0.9 eq) was added. The mixture was warned to 20° C. and stirred for another 2 hours. The mixture was diluted with THF (5 ml) and filtered. The filtrate was concentrated under reduce pressure to afford a residue. The residue was purified by prep-HPLC (neutral condition; column: Xtimate C18 150*40 mm*10 um; mobile phase: [water(10 mM NH$_4$HCO$_3$)-ACN]; B %: 65%-85%, 10 min) to afford the compound 1-(4-chloro-3-nitro-phenyl)-3-[4-fluoro-3-[3-(trifluoromethyl)diazirin-3-yl]phenyl]urea (0.0092 g, 21.10 μmol, 9.80% yield, 95.78% purity) as a light-yellow solid. $^1$H NMR: (DMSO-d6, 400 MHz) δ 9.36 (s, 1H), 9.18 (s, 1H), 8.27 (s, 1H), 7.82-7.85 (m, 1H), 7.64 (s, 2H), 7.52 (m, 1H), 7.32-7.37 (m, 1H).

Example 43: Preparation of N-[2-chloro-5-[(4-fluorophenyl) carbamoylamino] phenyl]acetamide (Compound 0095)

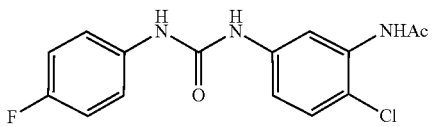 [SMILES: CC(=O)Nc1cc(NC(=O)Nc2ccc(F)cc2)ccc1Cl]

Step 1: Preparation of N-(2-chloro-5-nitro-phenyl)acetamide: To a mixture of 2-chloro-5-nitro-aniline (1 g, 5.79 mmol, 1 eq) in DCM (10 mL) was added TEA (2.93 g, 28.97 mmol, 4.03 mL, 5 eq) at 0° C. Then acetyl chloride (1.36 g, 17.38 mmol, 1.24 mL, 3 eq) was added to the mixture. The mixture was stirred at 25° C. for 12 hours. The mixture was poured to water (10 mL) and extracted with DCM (10 mL*2). The combined organic layers were washed with brine (10 mL*2), dried over Na$_2$SO$_4$, filtered and concentrated under reduced pressure to give a residue. The residue was purified by flash silica gel chromatography (ISCO®; 20 g SepaFlash® Silica Flash Column, Eluent of 0~39% Ethyl acetate/Petroleum ether gradient@75 mL/min) to afford compound N-(2-chloro-5-nitro-phenyl)acetamide (0.54 g, 2.04 mmol, 35.17% yield, 81% purity) as a yellow solid.

Step 2: Preparation of N-(5-amino-2-chloro-phenyl)acetamide: To a mixture of N-(2-chloro-5-nitro-phenyl)acetamide (0.54 g, 2.52 mmol, 1 eq) in EtOH (10 mL) and FLO (3 mL) was added Fe (1.41 g, 25.16 mmol, 10 eq) and NH$_4$Cl (672.97 mg, 12.58 mmol, 5 eq). The mixture was stirred at 60° C. for 2 hours. The reaction mixture filtered and concentrated under reduced pressure to give a residue. The crude product was purified by reversed-phase HPLC (0.1% TFA condition) to afford the compound N-(5-amino-2-chloro-phenyl)acetamide (0.2 g, 669.69 μmol, 26.61% yield, TFA) as a white solid. $^1$H NMR: (400 MHz, DMSO) δ 9.26 (br s, 1H), 7.19 (br d, J=8.6 Hz, 2H), 6.55 (br s, 1H), 2.07 (s, 3H).

Step 3: Preparation of N-[2-chloro-5-[(4-fluorophenyl) carbamoylamino] phenyl]acetamide: To a mixture of 4-fluoroaniline (18.60 mg, 167.42 μmol, 16.04 uL, 1 eq) in THF (2 mL) was added TEA (50.82 mg, 502.27 μmol, 69.91 uL, 3 eq) and triphosgene (17.39 mg, 58.60 μmol, 0.35 eq) at 0° C. Then the mixture was stirred at 0° C. for 30 min, then N-(5-amino-2-chloro-phenyl)acetamide (0.05, 167.42 μmol, 1 eq, TFA) was added to the mixture. The mixture was stirred at 25° C. for 2 hours. The mixture was poured to water (10 mL) and extracted with EtOAc (10 mL*2). The combined organic layers were washed with brine (10 mL*2), dried over Na$_2$SO$_4$, filtered and concentrated under reduced pressure to give a residue. The residue was purified by prep-HPLC (neutral condition) to afford compound N-[2-chloro-5-[(4-fluorophenyl) carbamoylamino] phenyl] acetamide (16.2 mg, 49.85 μmol, 29.77% yield, 99.00% purity) as a white solid. $^1$H NMR: (400 MHz, DMSO-d6) δ 9.42 (s, 1H), 8.86 (s, 1H), 8.66 (s, 1H), 7.85 (s, 1H), 7.49-7.41 (m, 2H), 7.37-7.32 (m, 2H), 7.15-7.08 (m, 2H), 2.13-2.05 (m, 3H).

Example 44: Preparation of 1-(4-chlorophenyl)-3-(4-fluorophenyl)urea (Compound 0096)

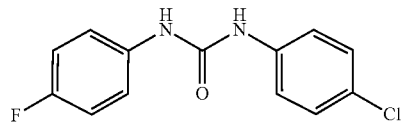 [SMILES: O=C(Nc1ccc(F)cc1)Nc1ccc(Cl)cc1]

1-fluoro-4-isocyanatobenzene (1.0 equiv) and 4-chloroaniline (1.0 equiv) were dissolved in dichloromethane (each 0.5 M) and stirred gently at 25° C. for 48 hours. 1-(4-chlorophenyl)-3-(4-fluorophenyl)urea was collected by filtration, washed with dichloromethane, and dried under vacuum.

Example 45: Preparation of 1-(4-chloro-3-(trifluoromethyl)phenyl)-3-(3,4-difluorophenyl)urea (Compound 0101)

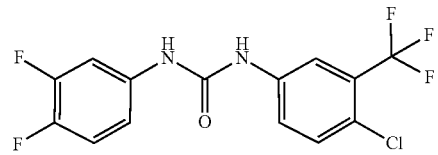 [SMILES: O=C(Nc1ccc(F)c(F)c1)Nc1ccc(Cl)c(C(F)(F)F)c1]

1,2-difluoro-4-isocyanatobenzene (1.0 equiv) and 4-chloro-3-(trifluoromethyl)aniline (1.0 equiv) were dissolved in dichloromethane (each 0.5 M) and stirred gently at 25° C. for 48 hours. 1-(4-chloro-3-(trifluoromethyl)phenyl)-3-(3,4-difluorophenyl)urea was collected by filtration, washed with dichloromethane, and dried under vacuum.

Example 46: Preparation of 1-(4-chloro-3-hydroxyphenyl)-3-(4-fluorophenyl)urea (Compound 0103)

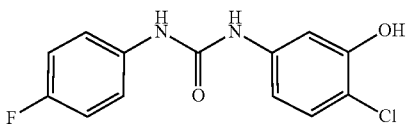 [SMILES: O=C(Nc1ccc(F)cc1)Nc1ccc(Cl)c(O)c1]

1-fluoro-4-isocyanatobenzene (1.0 equiv) and 5-amino-2-chlorophenol (1.0 equiv) were dissolved in dichloromethane (each 0.5 M) and stirred gently at 25° C. for 48 hours. 1-(4-chloro-3-hydroxyphenyl)-3-(4-fluorophenyl)urea was collected by filtration, washed with dichloromethane, and dried under vacuum.

Example 47: Preparation of 1-(4-(tert-butyl)phenyl)-3-(4-chloro-3-nitrophenyl)urea (Compound 0105)

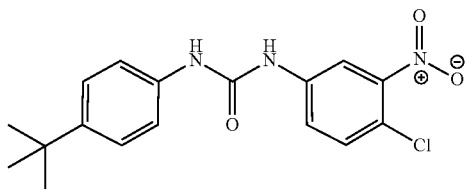 [SMILES: CC(C)(C)c1ccc(NC(=O)Nc2ccc(Cl)c([N+](=O)[O-])c2)cc1]

1-(tert-butyl)-4-isocyanatobenzene (1.0 equiv) and 4-chloro-3-nitroaniline (1.0 equiv) were dissolved in dichloromethane (each 0.5 M) and stirred gently at 25° C. for 48 hours. 1-(4-(tert-butyl)phenyl)-3-(4-chloro-3-nitrophenyl)urea was collected by filtration, washed with dichloromethane, and dried under vacuum.

Example 48: Preparation of 5-fluoro-2-(3-(3-nitrophenyl)ureido)benzoic acid (Compound 0106)

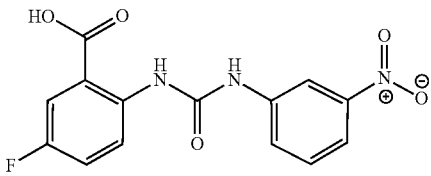 [SMILES: O=C(Nc1cccc([N+](=O)[O-])c1)Nc1ccc(F)cc1C(=O)O]

1-isocyanato-3-nitrobenzene (1.0 equiv) and 2-amino-5-fluorobenzoic acid (1.0 equiv) were dissolved in dichloromethane (each 0.5 M) and stirred gently at 25° C. for 48 hours. 5-fluoro-2-(3-(3-nitrophenyl)ureido)benzoic acid was collected by filtration, washed with dichloromethane, and dried under vacuum.

Example 49: Preparation of 1-(3-nitrophenyl)-3-(p-tolyl)urea (Compound 0110)

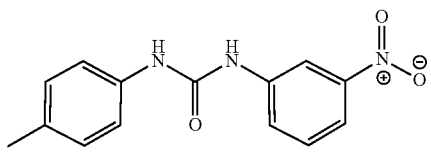 [SMILES: Cc1ccc(NC(=O)Nc2cccc([N+](=O)[O-])c2)cc1]

1-isocyanato-4-methylbenzene (1.0 equiv) and 3-nitroaniline (1.0 equiv) were dissolved in dichloromethane (each 0.5 M) and stirred gently at 25° C. for 48 hours. 1-(3-nitrophenyl)-3-(p-tolyl)urea was collected by filtration, washed with dichloromethane, and dried under vacuum.

Example 50: Preparation of 3-[4-chloro-3-(trifluoromethylsulfonyl)anilino]-4-(4-fluoroanilino)cyclobut-3-ene-1,2-dione (Compound 0112)

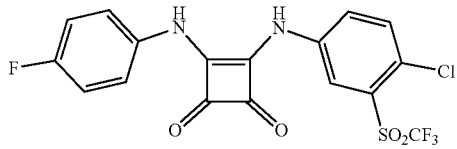

Step 1: Preparation of 2-chloro-5-nitrobenzenediazonium tetrafluoroborate: To a solution of 2-chloro-5-nitro-aniline (10.35 g, 0.06 mol, 1 eq) in EtOH (18 mL) was added $HBF_4$ (26.34 g, 120.00 mmol, 12.3 mL, 40% purity, 2 eq) and t-BuONO (12.37 g, 120.00 mmol, 14.27 mL, 2 eq) at 0° C. After addition, the mixture was stirred at 25° C. for 2 hours. The yellow precipitate was formed in the reaction mixture. The mixture was quenched by addition of diisopropylether (100 mL) at 20° C., filtered. The filtered cake was washed with diisopropylether (50 mL*3), dried in vacuum afford the crude product 2-chloro-5-nitrobenzenediazonium tetrafluoroborate (11.85 g, crude) as a yellow solid which was used into the next step without further purification.

Step 2: Preparation of 1-chloro-4-nitro-2-(trifluoromethylsulfonyl)benzene: To a solution of 2-chloro-5-nitrobenzenediazonium tetrafluoroborate (10.35 g, 38.14 mmol, 1 eq) in DMSO (200 mL) was added $Cu_2O$ (545.76 mg, 3.81 mmol, 389.83 uL, 0.1 eq) and sodium trifluoromethanesulfinate (17.86 g, 114.42 mmol, 17.86 mL, 3 eq). The mixture was stirred at 25° C. for 12 hours. The mixture was quenched by addition of $H_2O$ (250 mL) at 0° C., extracted with EtOAc (200 mL*2). The combined organic layers were washed with $H_2O$ (300 mL*3), brine (300 mL), dried over $Na_2SO_4$ and filtered. The filtrate was concentrated under reduced pressure to afford a residue. The residue was purified by flash silica gel chromatography (ISCO®; 120 g SepaFlash® Silica Flash Column, Eluent of 0~30% Ethyl acetate/Petroleum ether gradient@100 mL/min) to afford the compound 1-chloro-4-nitro-2-(trifluoromethylsulfonyl)benzene (0.6 g, 2.07 mmol, 5.43% yield) as light-yellow oil. $^1$H NMR: (DMSO-d6, 400 MHz) δ 8.80-8.83 (m, 2H), 8.29-8.32 (m, 1H).

Step 3: Preparation of 4-chloro-3-(trifluoromethylsulfonyl)aniline: To a solution of 1-chloro-4-nitro-2-(trifluoromethylsulfonyl)benzene (0.6 g, 2.07 mmol, 1 eq) in EtOH (10 mL)\$H_2O$ (2 mL) was added Fe (1.16 g, 20.72 mmol, 10 eq) and $NH_4Cl$ (554.09 mg, 10.36 mmol, 5 eq). The mixture was stirred at 65° C. for 3 hours. The mixture was filtered and the filter cake was washed with MeOH (10 mL*2). The filtrated was concentrated under reduced pressure to afford a residue. The residue was purified by flash silica gel chromatography (ISCO®; 12 g SepaFlash® Silica Flash Column, Eluent of 0~100% Ethyl acetate/Petroleum ether gradient@36 mL/min) to afford the compound 4-chloro-3-(trifluoromethylsulfonyl)aniline (0.36 g, 1.39 mmol, 66.93% yield) as yellow oil.

Step 4: Preparation of 3-[4-chloro-3-(trifluoromethylsulfonyl)anilino]-4-ethoxy-cyclobut-3-ene-1,2-dione: To a solution of 4-chloro-3-(trifluoromethylsulfonyl)aniline (0.2 g, 770.32 μmol, 1 eq) in EtOH (3 mL) was added 3,4-diethoxycyclobut-3-ene-1,2-dione (157.29 mg, 924.38 μmol, 135.60 uL, 1.2 eq). The mixture was stirred at 70° C. for 12 hours. The mixture was concentrated directly under reduced pressure to afford a residue. The residue was purified by flash silica gel chromatography (ISCO®; 4 g Sepa-Flash® Silica Flash Column, Eluent of 0~100% Ethyl acetate/Petroleum ether gradient@25 mL/min) to afford the compound 3-[4-chloro-3-(trifluoromethylsulfonyl)anilino]-4-ethoxy-cyclobut-3-ene-1,2-dione (0.2 g, 521.20 μmol, 67.66% yield) as a yellow solid.

Step 5: Preparation of 3-[4-chloro-3-(trifluoromethylsulfonyl)anilino]-4-(4-fluoroanilino)cyclobut-3-ene-1,2-dione: To a solution of 3-[4-chloro-3-(trifluoromethylsulfonyl)anilino]-4-ethoxy-cyclobut-3-ene-1,2-dione (0.06 g, 156.36 μmol, 1 eq) in THF (2 mL) was added 4-fluoroaniline (17.37 mg, 156.36 μmol, 14.98 uL, 1 eq) and AlMe$_3$ (2 M, 156.36 uL, 2 eq). The mixture was heated to 50° C. and stirred for 12 hours. The mixture was quenched by addition of saturated aqueous NH$_4$Cl (5 mL) at 0° C., extracted with EtOAc (10 mL*2). The combined organic layers were washed with H$_2$O (10 mL), brine (10 mL), dried over Na$_2$SO$_4$ and filtered. The filtrate was concentrated under reduced pressure to afford a residue. The residue was purified by prep-HPLC (FA condition, column: Luna C18 100*30 5 u; mobile phase: [water (0.225% FA)-ACN]; B %: 40%-70%, 12 min) to afford the compound 3-[4-chloro-3-(trifluoromethylsulfonyl)anilino]-4-(4-fluoroanilino)cyclobut-3-ene-1,2-dione (8.20 mg, 17.71 μmol, 11.33% yield, 96.92% purity) as a white solid. $^1$H NMR: (DMSO-d6, 400 MHz) δ 8.22 (s, 1H), 7.86-7.92 (m, 2H), 7.41-7.45 (m, 2H), 7.19-7.23 (m, 2H).

Example 51: Preparation of 1-(4-chlorophenyl)-3-(p-tolyl)urea (Compound 0113)

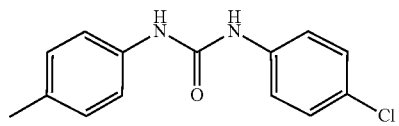 [SMILES: Cc1ccc(NC(=O)Nc2ccc(Cl)cc2)cc1]

1-isocyanato-4-methylbenzene (1.0 equiv) and 4-chloroaniline (1.0 equiv) were dissolved in dichloromethane (each 0.5 M) and stirred gently at 25° C. for 48 hours. 1-(4-chlorophenyl)-3-(p-tolyl)urea was collected by filtration, washed with dichloromethane, and dried under vacuum.

Example 52: Preparation of 1-(3,4-dichlorophenyl)-3-(4-methoxyphenyl)urea (Compound 0117)

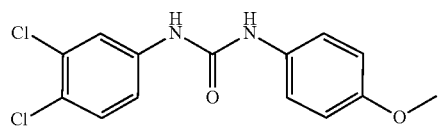 [SMILES: COc1ccc(NC(=O)Nc2ccc(Cl)c(Cl)c2)cc1]

1,2-dichloro-4-isocyanatobenzene (1.0 equiv) and 4-methoxyaniline (1.0 equiv) were dissolved in dichloromethane (each 0.5 M) and stirred gently at 25° C. for 48 hours. 1-(3,4-dichlorophenyl)-3-(4-methoxyphenyl)urea was collected by filtration, washed with dichloromethane, and dried under vacuum.

Example 53: Compounds 0118-0235

The following compounds are prepared according to the procedures known to those of skill in the art in view of Scheme 1 and Examples 3-52.

TABLE 2

| No. | Structure |
|---|---|
| 0118 | 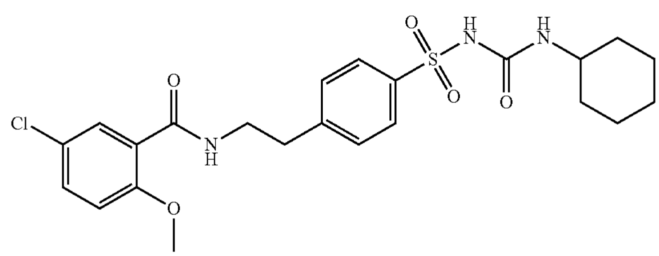 [SMILES: COc1ccc(Cl)cc1C(=O)NCCc1ccc(S(=O)(=O)NC(=O)NC2CCCCC2)cc1] |
| 0119 | 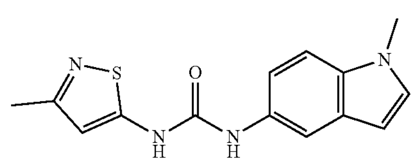 [SMILES: Cc1cc(NC(=O)Nc2ccc3c(ccn3C)c2)sn1] |
| 0120 | 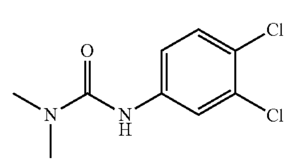 |

TABLE 2-continued

| No. | Structure |
|---|---|
| 0121 | 2-methylphenoxy-CH2-C(O)-NH-NH-C(O)-NH-phenyl |
| 0122 | 4-methoxyphenyl-NH-C(O)-NH-benzo[1,3]dioxol-5-yl |
| 0123 | (phenyl)2C(OH)-C(O)-NH-NH-C(O)-NH-(3-chlorophenyl) |
| 0124 | pyridin-2-yl-CH2-NH-C(O)-NH-(4-isopropylphenyl) |
| 0125 | pyridin-2-yl-CH2-NH-C(O)-NH-benzo[1,3]dioxol-5-yl |
| 0126 | pyridin-2-yl-CH2-NH-C(O)-NH-(2-trifluoromethylphenyl) |
| 0127 | pyridin-2-yl-CH2-NH-C(O)-NH-(4-nitrophenyl) |
| 0128 | pyridin-2-yl-CH2-NH-C(O)-NH-(2-chlorophenyl) |

TABLE 2-continued

| No. | Structure |
|---|---|
| 0129 | 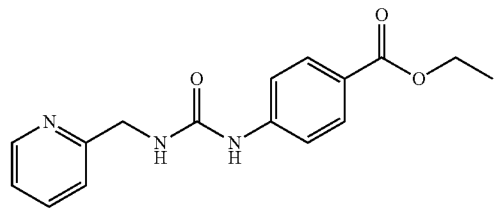 [SMILES: CCOC(=O)c1ccc(NC(=O)NCc2ccccn2)cc1] |
| 0130 | 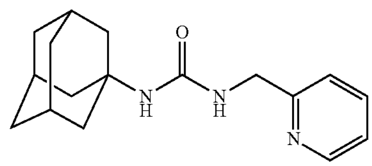 [SMILES: O=C(NCc1ccccn1)NC12CC3CC(CC(C3)C1)C2] |
| 0131 | 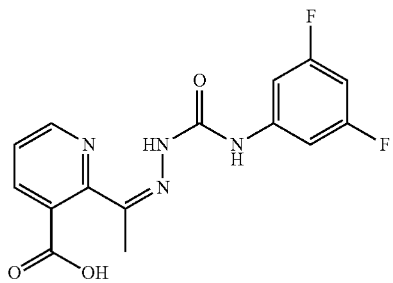 [SMILES: C/C(=N/NC(=O)Nc1cc(F)cc(F)c1)c1ncccc1C(=O)O] |
| 0132 | 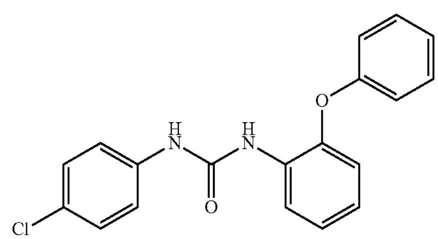 [SMILES: O=C(Nc1ccc(Cl)cc1)Nc1ccccc1Oc1ccccc1] |
| 0133 | 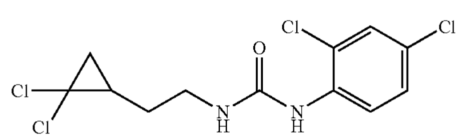 [SMILES: O=C(NCCC1CC1(Cl)Cl)Nc1ccc(Cl)cc1Cl] |
| 0134 | 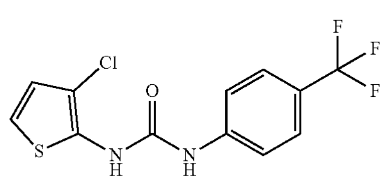 [SMILES: O=C(Nc1ccc(C(F)(F)F)cc1)Nc1sccc1Cl] |
| 0135 | 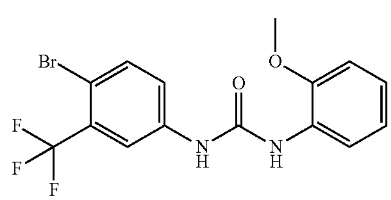 [SMILES: COc1ccccc1NC(=O)Nc1ccc(Br)c(C(F)(F)F)c1] |

TABLE 2-continued
| No. | Structure |
|---|---|
| 0136 | 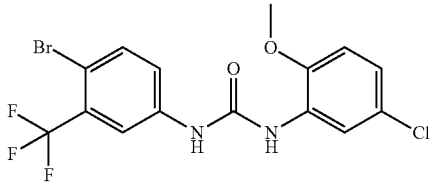 [SMILES: COc1ccc(Cl)cc1NC(=O)Nc1ccc(Br)c(C(F)(F)F)c1] |
| 0137 | 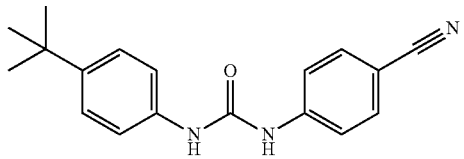 [SMILES: CC(C)(C)c1ccc(NC(=O)Nc2ccc(C#N)cc2)cc1] |
| 0138 | 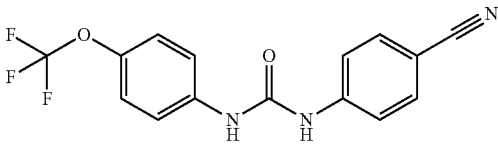 [SMILES: N#Cc1ccc(NC(=O)Nc2ccc(OC(F)(F)F)cc2)cc1] |
| 0139 | 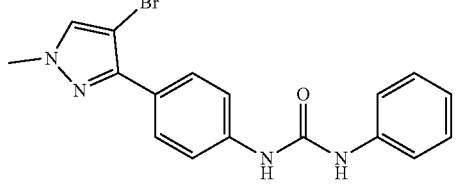 |
| 0140 | 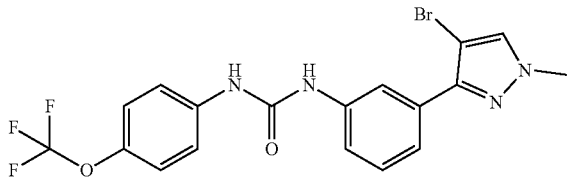 [SMILES: Cn1cc(Br)c(-c2cccc(NC(=O)Nc3ccc(OC(F)(F)F)cc3)c2)n1] |
| 0141 | 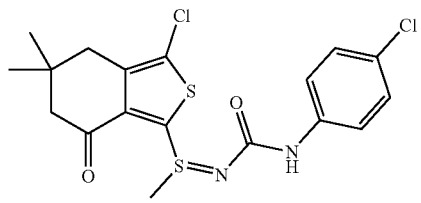 [SMILES: C/S(=N/C(=O)Nc1ccc(Cl)cc1)c1sc(Cl)c2c1C(=O)CC(C)(C)C2] |
| 0142 | 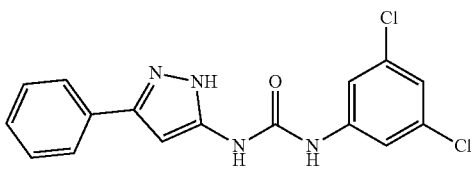 [SMILES: O=C(Nc1cc(Cl)cc(Cl)c1)Nc1cc(-c2ccccc2)n[nH]1] |
| 0143 | 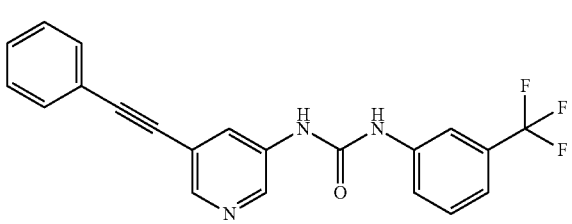 [SMILES: O=C(Nc1cncc(C#Cc2ccccc2)c1)Nc1cccc(C(F)(F)F)c1] |

TABLE 2-continued

| No. | Structure |
|-----|-----------|
| 0144 | 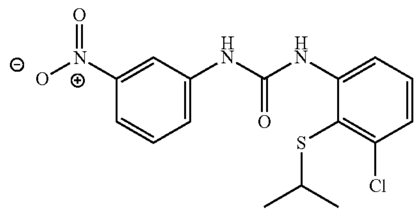 [SMILES: CC(C)Sc1c(Cl)cccc1NC(=O)Nc1cccc([N+](=O)[O-])c1] |
| 0145 | 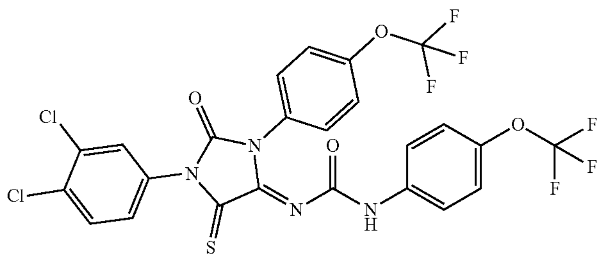 [SMILES: O=C(/N=C1/C(=S)N(c2ccc(Cl)c(Cl)c2)C(=O)N1c1ccc(OC(F)(F)F)cc1)Nc1ccc(OC(F)(F)F)cc1] |
| 0146 | 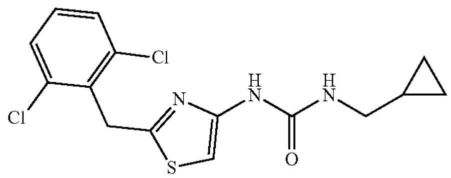 [SMILES: O=C(NCC1CC1)Nc1csc(Cc2c(Cl)cccc2Cl)n1] |
| 0147 | 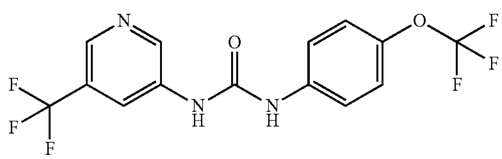 [SMILES: O=C(Nc1ccc(OC(F)(F)F)cc1)Nc1cncc(C(F)(F)F)c1] |
| 0148 | 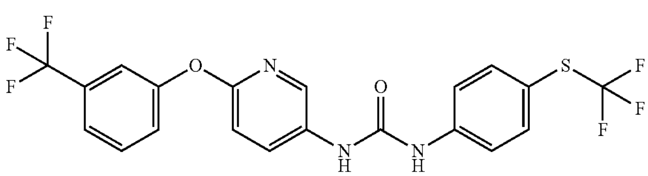 [SMILES: O=C(Nc1ccc(SC(F)(F)F)cc1)Nc1ccc(Oc2cccc(C(F)(F)F)c2)nc1] |
| 0149 | 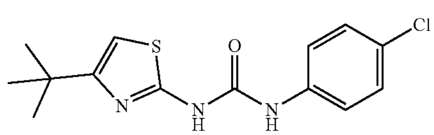 [SMILES: CC(C)(C)c1csc(NC(=O)Nc2ccc(Cl)cc2)n1] |
| 0150 | 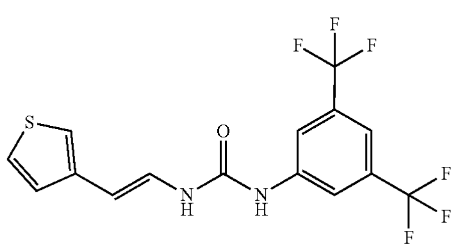 [SMILES: O=C(N/C=C/c1ccsc1)Nc1cc(C(F)(F)F)cc(C(F)(F)F)c1] |
| 0151 | 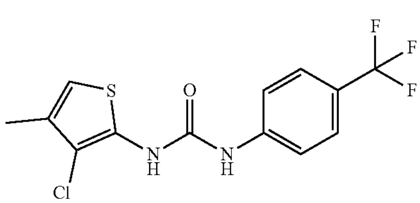 [SMILES: Cc1csc(NC(=O)Nc2ccc(C(F)(F)F)cc2)c1Cl] |

TABLE 2-continued

| No. | Structure |
|---|---|
| 0152 | 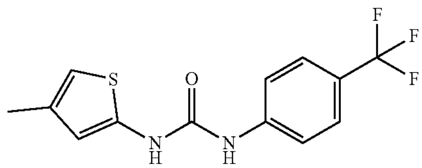 [SMILES: Cc1csc(NC(=O)Nc2ccc(C(F)(F)F)cc2)c1] |
| 0153 | 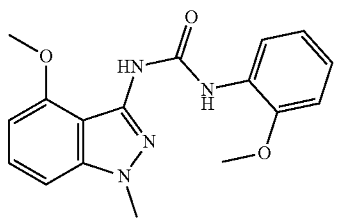 [SMILES: COc1ccccc1NC(=O)Nc1nn(C)c2cccc(OC)c12] |
| 0154 | 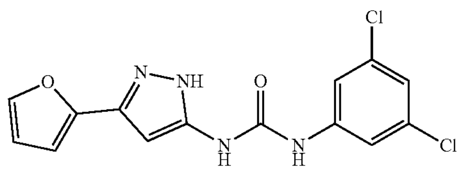 [SMILES: O=C(Nc1cc(Cl)cc(Cl)c1)Nc1cc(-c2ccco2)n[nH]1] |
| 0155 | 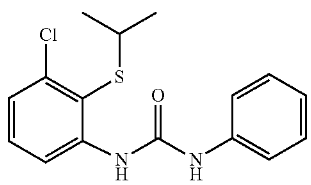 [SMILES: CC(C)Sc1c(Cl)cccc1NC(=O)Nc1ccccc1] |
| 0156 | 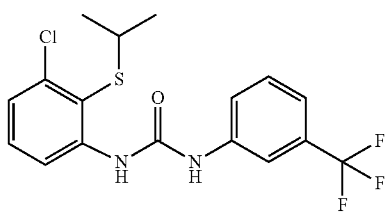 [SMILES: CC(C)Sc1c(Cl)cccc1NC(=O)Nc1cccc(C(F)(F)F)c1] |
| 0157 | 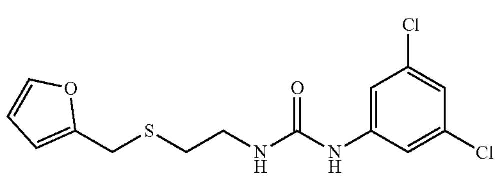 [SMILES: O=C(NCCSCc1ccco1)Nc1cc(Cl)cc(Cl)c1] |
| 0158 | 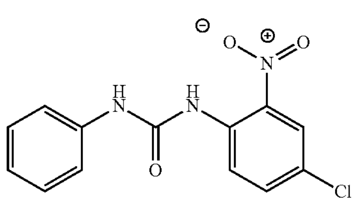 |
| 0159 | 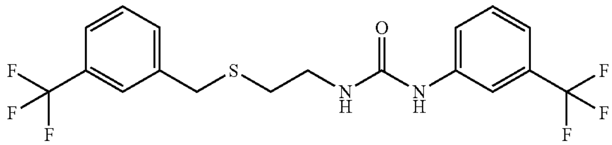 [SMILES: O=C(NCCSCc1cccc(C(F)(F)F)c1)Nc1cccc(C(F)(F)F)c1] |

TABLE 2-continued
| No. | Structure |
|---|---|
| 0160 | 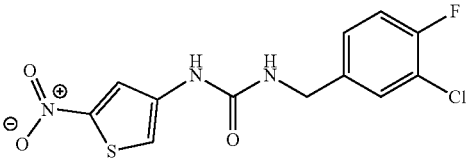 [SMILES: O=C(NCc1ccc(F)c(Cl)c1)Nc1csc([N+](=O)[O-])c1] |
| 0161 | 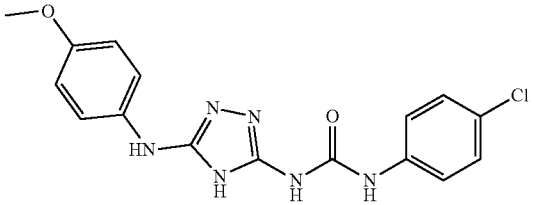 [SMILES: COc1ccc(Nc2nnc(NC(=O)Nc3ccc(Cl)cc3)[nH]2)cc1] |
| 0162 | 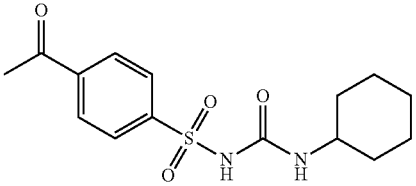 [SMILES: CC(=O)c1ccc(S(=O)(=O)NC(=O)NC2CCCCC2)cc1] |
| 0163 | 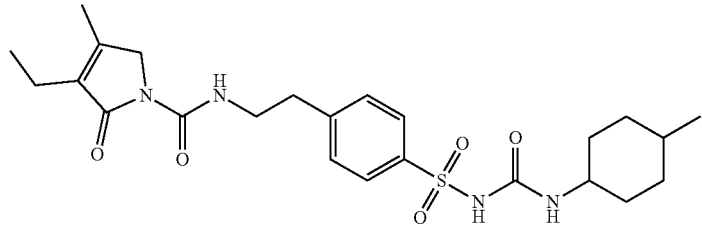 [SMILES: CCC1=C(C)CN(C(=O)NCCc2ccc(S(=O)(=O)NC(=O)NC3CCC(C)CC3)cc2)C1=O] |
| 0164 | 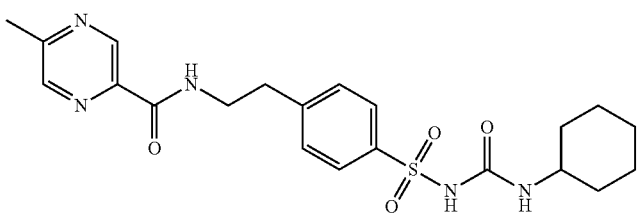 [SMILES: Cc1cnc(C(=O)NCCc2ccc(S(=O)(=O)NC(=O)NC3CCCCC3)cc2)cn1] |
| 0165 | 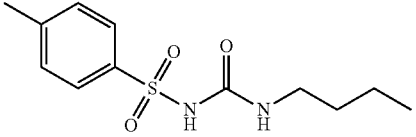 [SMILES: CCCCNC(=O)NS(=O)(=O)c1ccc(C)cc1] |
| 0166 | 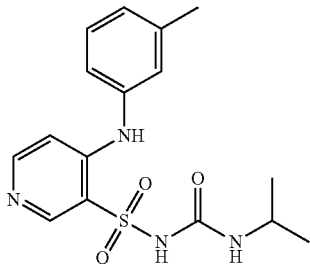 [SMILES: Cc1cccc(Nc2ccncc2S(=O)(=O)NC(=O)NC(C)C)c1] |

TABLE 2-continued

| No. | Structure |
|---|---|
| 0167 | (4-ureidophenyl)arsonic acid structure |
| 0168 | 4-chlorophenylsulfonyl propylurea structure |
| 0169 | 1-(4-chlorophenyl)-3-(3,4-dichlorophenyl)urea structure |
| 0170 | tolylsulfonyl azepanyl urea structure |
| 0171 | (2,5-dioxoimidazolidin-4-yl)urea structure |
| 0172 | glimepiride structure |
| 0173 | 1,3-diphenylurea structure |
| 0174 | 1-phenyl-3-(3-chlorophenyl)urea structure |
| 0175 | 1-phenyl-3-(4-chlorophenyl)urea structure |
| 0176 | 1-phenyl-3-(3-methylphenyl)urea structure |

TABLE 2-continued

| No. | Structure |
|---|---|
| 0177 | 1-phenyl-3-[3-(trifluoromethyl)phenyl]urea |
| 0178 | 1-phenyl-3-[4-(trifluoromethyl)phenyl]urea |
| 0179 | 1-phenyl-3-[4-bromo-3-(trifluoromethyl)phenyl]urea |
| 0180 | 1-(3-methoxyphenyl)-3-phenylurea |
| 0181 | 1-(4-methoxyphenyl)-3-phenylurea |
| 0182 | 1-(3-nitrophenyl)-3-phenylurea |
| 0183 | 1-(4-nitrophenyl)-3-phenylurea |
| 0184 | 1-(4-chloro-3-nitrophenyl)-3-phenylurea |
| 0185 | 1-(4-chlorophenyl)-3-phenylurea |
| 0186 | 1-(4-chlorophenyl)-3-(3-methylphenyl)urea |

TABLE 2-continued
| No. | Structure |
|---|---|
| 0187 | 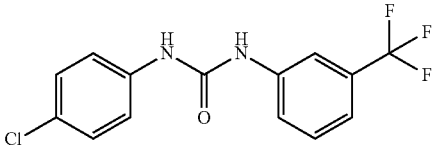 [SMILES: O=C(Nc1ccc(Cl)cc1)Nc1cccc(C(F)(F)F)c1] |
| 0188 | 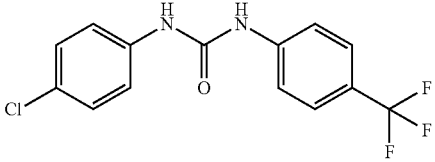 [SMILES: O=C(Nc1ccc(Cl)cc1)Nc1ccc(C(F)(F)F)cc1] |
| 0189 | 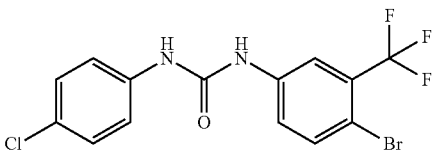 [SMILES: O=C(Nc1ccc(Cl)cc1)Nc1ccc(Br)c(C(F)(F)F)c1] |
| 0190 | 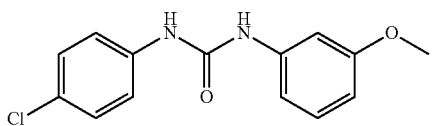 [SMILES: COc1cccc(NC(=O)Nc2ccc(Cl)cc2)c1] |
| 0191 | 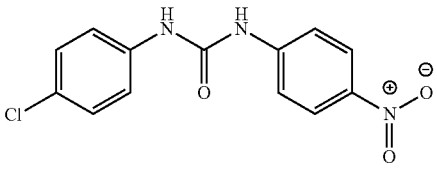 [SMILES: O=C(Nc1ccc(Cl)cc1)Nc1ccc([N+](=O)[O-])cc1] |
| 0192 | 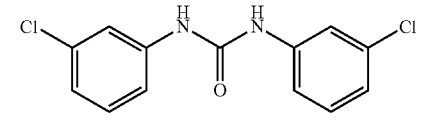 [SMILES: O=C(Nc1cccc(Cl)c1)Nc1cccc(Cl)c1] |
| 0193 | 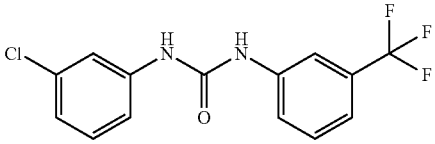 [SMILES: O=C(Nc1cccc(Cl)c1)Nc1cccc(C(F)(F)F)c1] |
| 0194 | 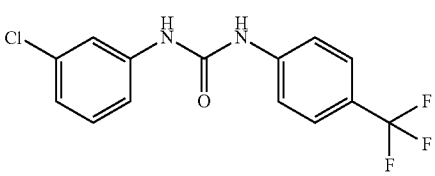 [SMILES: O=C(Nc1ccc(C(F)(F)F)cc1)Nc1cccc(Cl)c1] |
| 0195 | 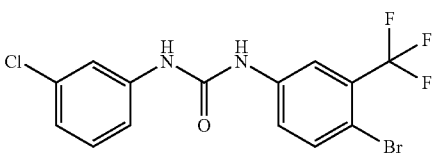 [SMILES: O=C(Nc1cccc(Cl)c1)Nc1ccc(Br)c(C(F)(F)F)c1] |
| 0196 | 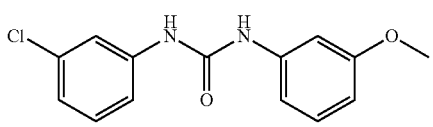 [SMILES: COc1cccc(NC(=O)Nc2cccc(Cl)c2)c1] |

TABLE 2-continued

| No. | Structure |
|---|---|
| 0197 | 3-chlorophenyl-N'-(4-methoxyphenyl)urea |
| 0198 | 3-chlorophenyl-N'-(4-nitrophenyl)urea |
| 0199 | N-(3,4-dichlorophenyl)-N'-(3-chlorophenyl)urea |
| 0200 | N-(3,4-dichlorophenyl)-N'-(3-methylphenyl)urea |
| 0201 | N-(3,4-dichlorophenyl)-N'-(3-trifluoromethylphenyl)urea |
| 0202 | N-(3,4-dichlorophenyl)-N'-(4-trifluoromethylphenyl)urea |
| 0203 | N-(3,4-dichlorophenyl)-N'-(4-bromo-3-trifluoromethylphenyl)urea |
| 0204 | N-(3,4-dichlorophenyl)-N'-(3-methoxyphenyl)urea |
| 0205 | N-(3,4-dichlorophenyl)-N'-(3-nitrophenyl)urea |
| 0206 | N-(3,4-dichlorophenyl)-N'-(4-nitrophenyl)urea |

TABLE 2-continued

| No. | Structure |
|---|---|
| 0207 | 1-(4-fluorophenyl)-3-phenylurea |
| 0208 | 1-(4-fluorophenyl)-3-(3-methylphenyl)urea |
| 0209 | 1-(4-fluorophenyl)-3-(4-(trifluoromethyl)phenyl)urea |
| 0210 | 1-(4-fluorophenyl)-3-(3-methoxyphenyl)urea |
| 0211 | 1-(4-fluorophenyl)-3-(4-methoxyphenyl)urea |
| 0212 | 1-(4-fluorophenyl)-3-(4-nitrophenyl)urea |
| 0213 | 1-(3-methylphenyl)-3-phenylurea |
| 0214 | 1-(3-methylphenyl)-3-(4-chlorophenyl)urea |
| 0215 | 1,3-bis(3-methylphenyl)urea |
| 0216 | 1-(3-methylphenyl)-3-(3-(trifluoromethyl)phenyl)urea |

TABLE 2-continued
| No. | Structure |
|---|---|
| 0217 | 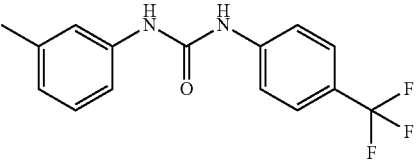 [SMILES: Cc1cccc(NC(=O)Nc2ccc(C(F)(F)F)cc2)c1] |
| 0218 | 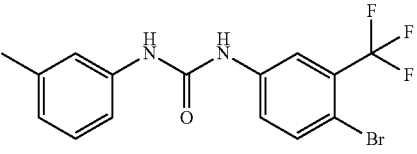 [SMILES: Cc1cccc(NC(=O)Nc2ccc(Br)c(C(F)(F)F)c2)c1] |
| 0219 | 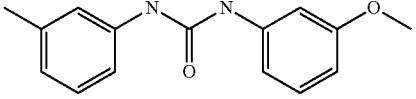 |
| 0220 | 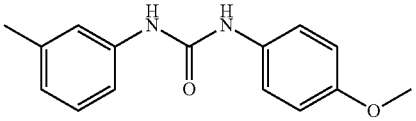 |
| 0221 | 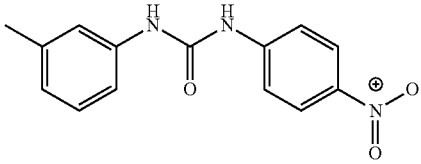 |
| 0222 | 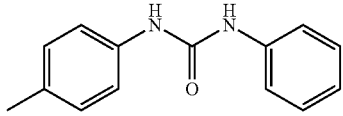 [SMILES: Cc1ccc(NC(=O)Nc2ccccc2)cc1] |
| 0223 | 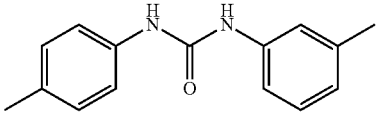 |
| 0224 | 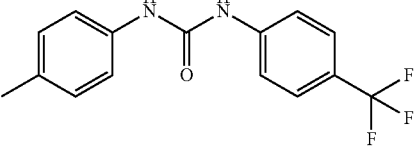 |
| 0225 | 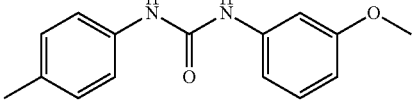 |
| 0226 | 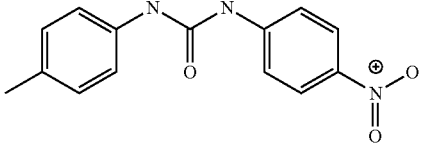 |

TABLE 2-continued
| No. | Structure |
|---|---|
| 0227 | 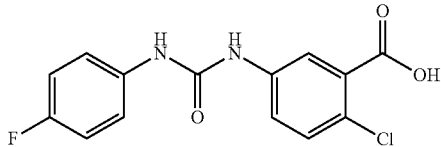 [SMILES: O=C(Nc1ccc(F)cc1)Nc1ccc(Cl)c(C(=O)O)c1] |
| 0228 | 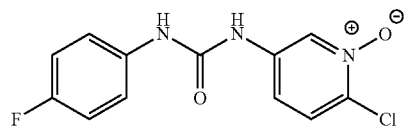 [SMILES: O=C(Nc1ccc(F)cc1)Nc1ccc(Cl)[n+]([O-])c1] |
| 0229 | 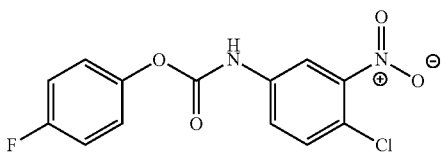 [SMILES: O=C(Nc1ccc(Cl)c([N+](=O)[O-])c1)Oc1ccc(F)cc1] |
| 0230 | 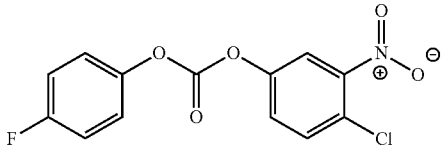 [SMILES: O=C(Oc1ccc(F)cc1)Oc1ccc(Cl)c([N+](=O)[O-])c1] |
| 0231 | 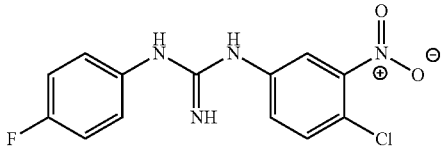 [SMILES: N=C(Nc1ccc(F)cc1)Nc1ccc(Cl)c([N+](=O)[O-])c1] |
| 0232 | 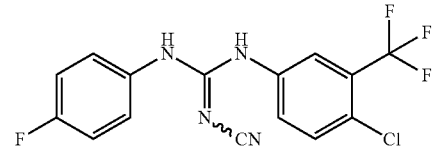 [SMILES: N#CN=C(Nc1ccc(F)cc1)Nc1ccc(Cl)c(C(F)(F)F)c1] |
| 0233 | 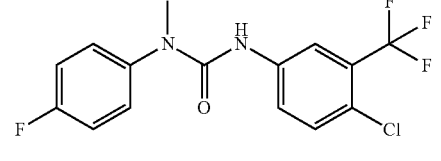 |
| 0234 | 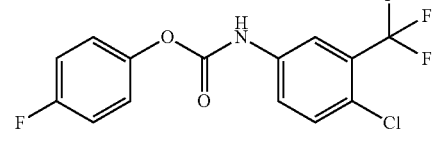 |
| 0235 | 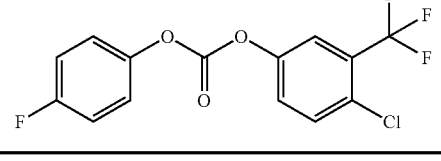 |

Example 54

HSF1 binding compounds were tested for its activity in suppressing the growth of a broad range of cancer types. For example, Compound 0017 was incubated for two days with a diverse series of cancer cell lines in the NCI60 collection and cell growth and viability were measured, and the results are shown in Table 4.

TABLE 4

HSF binding compound suppressing growth of various cancer cells

|  | $\log_{10}$ [GI$_{50}$ (M)] | $\log_{10}$ [TGI (M)] | $\log_{10}$ [LC$_{50}$ (M)] |
|---|---|---|---|
| Leukemia | | | |
| CCRF-CEM | −5.48 | −4.00 | −4.00 |
| HL-60(TB) | −5.60 | −5.07 | −4.00 |
| K-562 | −5.49 | −4.00 | −4.00 |
| MOLT-4 | −5.50 | −4.03 | −4.00 |
| RPMI-8226 | −5.72 | −5.07 | −4.00 |
| SR | −5.47 | −4.00 | −4.00 |
| Non-Small Cell Lung Cancer | | | |
| A549/ATCC | −5.51 | −4.79 | −4.00 |
| EKVX | −5.55 | −4.96 | −4.21 |
| HOP-62 | −5.42 | −4.80 | −4.25 |
| HOP-92 | −5.69 | −5.21 | −4.57 |
| NCI-H226 | −5.64 | −5.03 | −4.44 |
| NCI-H23 | −5.58 | −4.97 | −4.34 |
| NCI-H322M | −5.48 | −4.92 | −4.28 |
| NCI-H460 | −5.57 | −4.94 | −4.34 |
| NCI-H522 | −5.61 | −4.97 | −4.33 |
| Colon Cancer | | | |
| COLO 205 | −5.61 | −5.20 | −4.46 |
| HCC-2998 | −5.43 | −4.84 | −4.37 |
| HCT-116 | −5.51 | −4.93 | −4.46 |
| HCT-15 | −5.53 | −4.92 | −4.43 |
| HT29 | −5.49 | −4.91 | −4.27 |
| KM12 | −5.48 | −4.86 | −4.04 |
| SW-620 | −5.46 | −4.86 | −4.32 |
| CNS Cancer | | | |
| SF-268 | −5.35 | −4.76 | −4.24 |
| SF-295 | −5.64 | −5.10 | −4.51 |
| SF-539 | −5.41 | −4.84 | −4.39 |
| SNB-19 | −5.45 | −4.84 | −4.33 |
| SNB-75 | −5.23 | −4.00 | −4.00 |
| U251 | −5.50 | −4.90 | −4.36 |
| Melanoma | | | |
| LOX IMVI | −5.45 | −4.91 | −4.39 |
| MALME-3M | −5.63 | −5.14 | −4.53 |
| M14 | −5.50 | −4.91 | −4.42 |
| MDA-MB-435 | −5.51 | −4.94 | −4.36 |
| SK-MEL-2 | −5.63 | −5.23 | −4.60 |
| SK-MEL-28 | −5.42 | −4.85 | −4.42 |
| SK-MEL-5 | −5.75 | −5.49 | −5.23 |
| UACC-257 | −5.56 | −5.05 | −4.51 |
| UACC-62 | −5.52 | −4.88 | −4.44 |
| Ovarian Cancer | | | |
| IGROV1 | −5.32 | −4.73 | −4.13 |
| OVCAR-3 | −5.42 | −4.72 | −4.02 |
| OVCAR-4 | −5.56 | −4.85 | −4.06 |
| OVCAR-5 | −5.45 | −4.83 | −4.19 |
| OVCAR-8 | −5.53 | −4.82 | −4.00 |
| NCI/ADR-RES | −5.59 | −4.99 | −4.00 |
| SK-OV-3 | −5.58 | −5.12 | −4.37 |
| Renal Cancer | | | |
| 786-0 | −5.47 | −4.88 | −4.42 |
| A498 | −5.74 | −5.24 | −4.63 |
| ACHN | −5.53 | −4.96 | −4.22 |
| RXF 393 | −5.76 | −5.17 | −4.55 |
| SN12C | −5.53 | −4.93 | −4.37 |

TABLE 4-continued

HSF binding compound suppressing growth of various cancer cells

|  | $\log_{10}$ [GI$_{50}$ (M)] | $\log_{10}$ [TGI (M)] | $\log_{10}$ [LC$_{50}$ (M)] |
|---|---|---|---|
| TK-10 | −5.39 | −4.70 | −4.16 |
| UO-31 | −5.57 | −4.97 | −4.46 |
| Prostate Cancer | | | |
| PC-3 | −5.80 | −4.95 | −4.36 |
| DU-145 | −5.35 | −4.67 | −4.00 |
| Breast Cancer | | | |
| MCF7 | −5.58 | −4.92 | −4.15 |
| MDA-MB-231 | −5.60 | −5.19 | −4.47 |
| HS 578T | −5.40 | −4.62 | −4.00 |
| BT-549 | −5.54 | −4.97 | −4.48 |
| T-47D | −5.66 | −5.01 | −4.29 |
| MDA-MB-468 | −5.67 | −5.12 | −4.45 |

One skilled in the art will readily appreciate that the present disclosure is well adapted to carry out the objects and obtain the ends and advantages mentioned, as well as those inherent therein. The embodiments described herein, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

What is claimed is:

1. A method of treating cancer associated with an elevated HSF1 activity in a subject in need thereof, the method comprising administering to the subject an effective amount of an HSF1 inhibiting compound selected from the group consisting of:

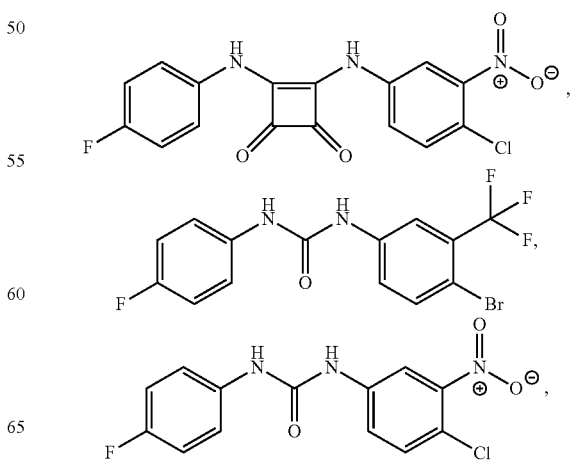

-continued

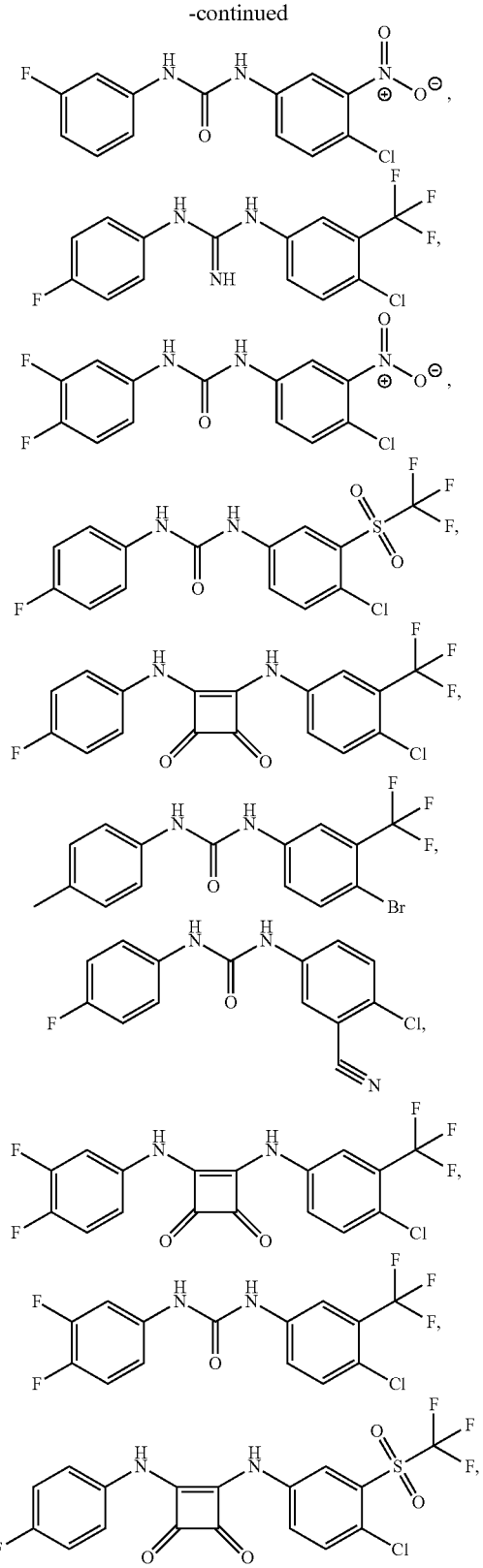

and combinations thereof,
wherein the cancer is selected from the group consisting of breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, head and neck cancer, leukemia (including but not limited to acute lymphoblastic leukemia and acute myeloid leukemia), sarcoma, carcinoma, stromal cancer, testicular cancer, neurofibroma, hepatocellular carcinoma, lymphoma, Ewing sarcoma and peripheral neuroepithelioma.

2. The method of claim 1, wherein the compound binds directly to an HSF1 protein to inhibit HSF1 activity in the subject.

3. The method of claim 2, wherein inhibiting HSF1 activity comprises inhibition of HSF1 homo-trimerization, inhibition of HSF1 target gene expression, inhibition of HSF1 target protein expression, inhibition of HSF1-mediated genome-wide transcriptional regulation, inhibition of protein chaperone activity, or a combination thereof.

4. The method of claim 2, wherein the binding of the compound increases the melting temperature of the HSF1 protein by at least 1° C. when compared with the melting temperature of the HSF1 protein prior to binding.

5. The method of claim 2, wherein the binding of the compound decreases the melting temperature of the HSF1 protein by at least 1° C. when compared with the melting temperature of the HSF1 protein prior to binding.

6. The method of claim 1, wherein the cancer is prostate cancer.

7. A compound having the structure of

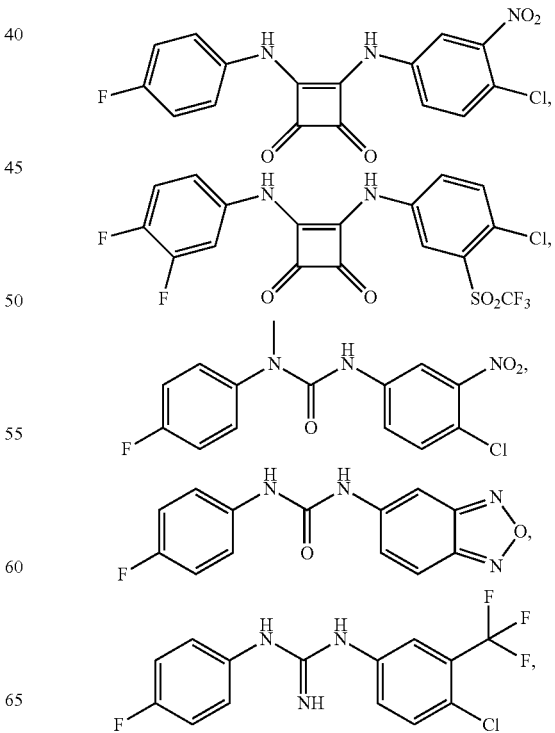

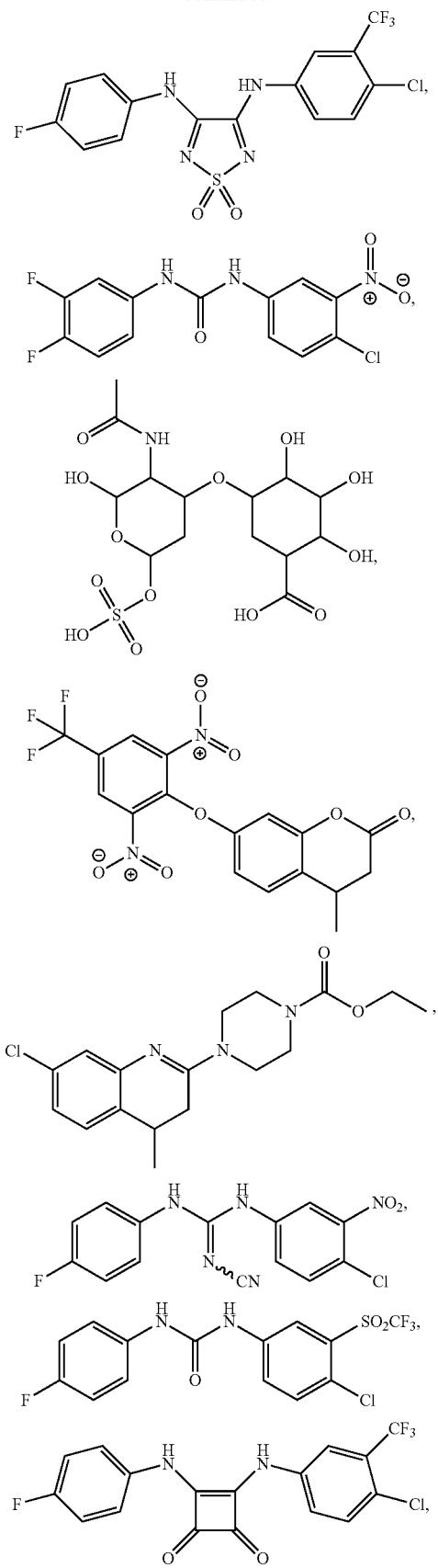
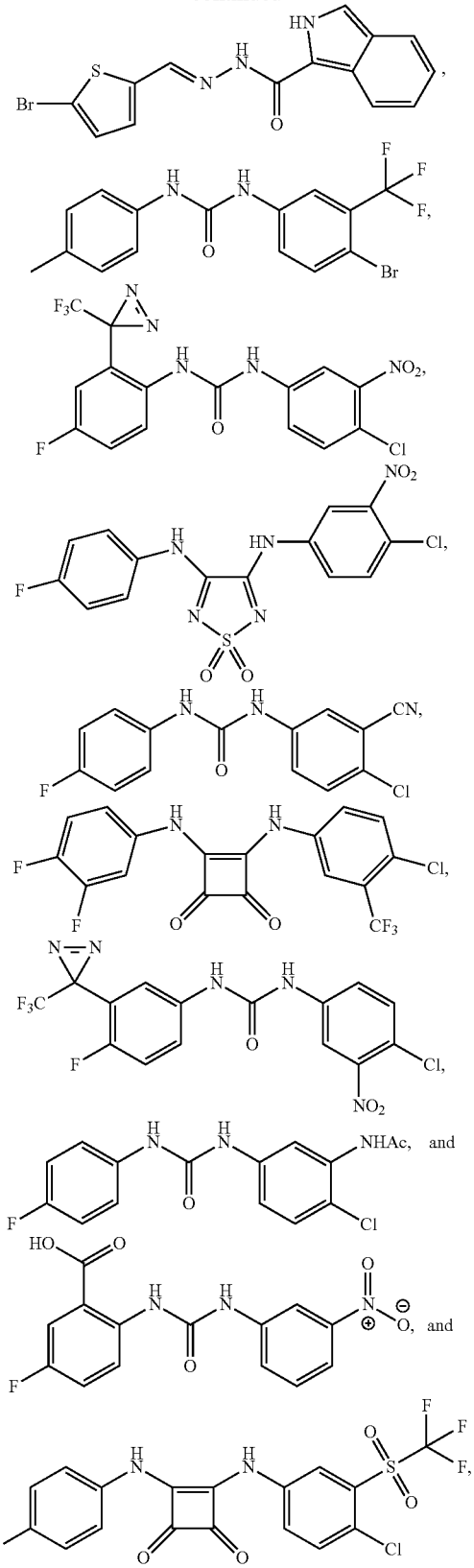
or a pharmaceutically acceptable salt thereof.
* * * * *